(12) United States Patent
Curley et al.

(10) Patent No.: US 11,083,871 B2
(45) Date of Patent: Aug. 10, 2021

(54) SELECTIVELY DEPLOYABLE CATHETER ABLATION DEVICES

(71) Applicant: Thermedical, Inc., Waltham, MA (US)

(72) Inventors: Michael G. Curley, Weston, MA (US); Fredrick J. Kim, Cambridge, MA (US); Michael T. Howard, Dracut, MA (US); Erik Delly, Cambridge, MA (US); Gregory R. Eberl, Acton, MA (US); Jeffrey J. Lesica, Holliston, MA (US)

(73) Assignee: Thermedical, Inc., Waltham, MA (US)

( * ) Notice: Subject to any disclaimer, the term of this patent is extended or adjusted under 35 U.S.C. 154(b) by 0 days.

(21) Appl. No.: 15/970,543

(22) Filed: May 3, 2018

(65) Prior Publication Data

US 2019/0336729 A1    Nov. 7, 2019

(51) Int. Cl.
*A61M 25/00* (2006.01)
*A61B 18/14* (2006.01)
(Continued)

(52) U.S. Cl.
CPC ..... *A61M 25/0084* (2013.01); *A61B 18/1477* (2013.01); *A61M 25/0074* (2013.01);
(Continued)

(58) Field of Classification Search
CPC .......... A61M 25/0084; A61M 25/0074; A61M 25/0147; A61M 2025/0089;
(Continued)

(56) References Cited

U.S. PATENT DOCUMENTS 4,160,455 A    7/1979 Law
4,424,190 A    1/1984 Mather, III et al.
(Continued)

FOREIGN PATENT DOCUMENTS

CN    1159154 A    9/1997
CN    1323233 A    11/2001
(Continued)

OTHER PUBLICATIONS

European Invitation to Attend Oral Proceedings for Application No. 12771601.7 dated Feb. 19, 2020 (7 Pages).
(Continued)

*Primary Examiner* — Amber R Stiles
(74) *Attorney, Agent, or Firm* — Barnes & Thornburg LLP

(57) ABSTRACT

Catheters with deployable instruments (e.g., needles) can damage tissue if the instrument unintentionally deploys during use. Described herein are devices and methods for controlling the position of a deployable catheter instrument. In one embodiment, a catheter can include an instrument slidably disposed within an inner lumen of the catheter and coupled to at least one protrusion, as well as a retraction stop coupled to the catheter. The catheter can further include a biasing element coupled to the instrument that can urge the instrument proximally such that the at least one protrusion abuts against the retraction stop, as well as an advancing mechanism to selectively engage the instrument and urge it distally. In some embodiments, the biasing element can be omitted and a deployment stop can be included distal to the retraction stop. These configurations can prevent unintentional instrument deployment and provide greater positioning precision during instrument deployment.

12 Claims, 36 Drawing Sheets

(51) Int. Cl.
*A61M 25/01* (2006.01)
*A61B 18/00* (2006.01)

(52) U.S. Cl.
CPC .............. *A61M 25/0147* (2013.01); *A61B 2018/00029* (2013.01); *A61B 2018/00041* (2013.01); *A61B 2018/00577* (2013.01); *A61M 2025/0089* (2013.01); *A61M 2202/0468* (2013.01); *A61M 2205/054* (2013.01); *A61M 2205/3653* (2013.01)

(58) Field of Classification Search
CPC .. A61M 2205/3653; A61M 2202/0468; A61M 2205/054; A61B 18/1477; A61B 2018/00029; A61B 2018/00041; A61B 2018/00577; A61B 2018/046; A61B 2018/1475; A61B 2018/1425; A61B 2218/002; A61B 2090/034; A61B 18/1492
See application file for complete search history.

(56) References Cited

U.S. PATENT DOCUMENTS

| | | |
|---|---|---|
| 5,190,538 A | 3/1993 | Hussein et al. |
| 5,271,413 A | 12/1993 | Dalamagas et al. |
| 5,336,222 A | 8/1994 | Durgin, Jr. et al. |
| 5,403,311 A | 4/1995 | Abele et al. |
| 5,409,487 A | 4/1995 | Jalbert et al. |
| 5,431,648 A | 7/1995 | Lev |
| 5,431,649 A | 7/1995 | Mulier et al. |
| 5,437,629 A | 8/1995 | Goldrath |
| 5,437,673 A | 8/1995 | Baust et al. |
| 5,449,380 A | 9/1995 | Chin |
| 5,456,682 A | 10/1995 | Edwards et al. |
| 5,458,597 A | 10/1995 | Edwards et al. |
| 5,462,521 A | 10/1995 | Brucker et al. |
| 5,472,441 A | 12/1995 | Edwards et al. |
| 5,496,271 A | 3/1996 | Burton et al. |
| 5,522,815 A | 6/1996 | Durgin, Jr. et al. |
| 5,545,195 A | 8/1996 | Lennox et al. |
| 5,549,559 A | 8/1996 | Eshel |
| 5,573,510 A | 11/1996 | Isaacson |
| 5,609,151 A | 3/1997 | Mulier et al. |
| 5,653,692 A | 8/1997 | Masterson et al. |
| 5,728,143 A | 3/1998 | Gough et al. |
| 5,735,846 A | 4/1998 | Panescu et al. |
| 5,800,482 A | 9/1998 | Pomeranz et al. |
| 5,827,269 A | 10/1998 | Saadat |
| 5,891,094 A | 4/1999 | Masterson et al. |
| 5,891,134 A | 4/1999 | Goble et al. |
| 5,944,713 A | 8/1999 | Schuman |
| 5,954,719 A | 9/1999 | Chen et al. |
| 5,964,791 A | 10/1999 | Bolmsjo |
| 6,024,743 A | 2/2000 | Edwards |
| 6,030,379 A | 2/2000 | Panescu et al. |
| 6,032,077 A | 2/2000 | Pomeranz |
| 6,033,383 A | 3/2000 | Ginsburg |
| 6,045,549 A | 4/2000 | Smethers et al. |
| 6,056,746 A | 5/2000 | Goble et al. |
| 6,071,280 A | 6/2000 | Edwards et al. |
| 6,080,151 A | 6/2000 | Swartz et al. |
| 6,090,106 A | 7/2000 | Goble et al. |
| 6,112,123 A | 8/2000 | Kelleher et al. |
| 6,119,041 A | 9/2000 | Pomeranz et al. |
| 6,139,570 A | 10/2000 | Saadat et al. |
| 6,139,571 A | 10/2000 | Fuller et al. |
| 6,179,803 B1 | 1/2001 | Edwards et al. |
| 6,208,881 B1 | 3/2001 | Champeau |
| 6,233,490 B1 | 5/2001 | Kasevich |
| 6,235,023 B1 | 5/2001 | Lee et al. |
| 6,238,393 B1 | 5/2001 | Mulier et al. |
| 6,272,370 B1 | 8/2001 | Gillies et al. |
| 6,302,904 B1 | 10/2001 | Wallsten et al. |
| 6,315,777 B1 | 11/2001 | Comben |
| 6,328,735 B1 | 12/2001 | Curley et al. |
| 6,337,994 B1 | 1/2002 | Stoianovici et al. |
| 6,358,273 B1 | 3/2002 | Strul et al. |
| 6,405,067 B1 | 6/2002 | Mest et al. |
| 6,409,722 B1 | 6/2002 | Hoey et al. |
| 6,411,852 B1 | 6/2002 | Danek et al. |
| 6,443,947 B1 | 9/2002 | Marko et al. |
| 6,463,332 B1 | 10/2002 | Aldrich |
| 6,464,694 B1 | 10/2002 | Massengill |
| 6,468,274 B1 | 10/2002 | Alleyne et al. |
| 6,475,213 B1 | 11/2002 | Whayne et al. |
| 6,477,396 B1 | 11/2002 | Mest et al. |
| 6,494,902 B2 | 12/2002 | Hoey et al. |
| 6,514,251 B1 | 2/2003 | Ni et al. |
| 6,529,756 B1 | 3/2003 | Phan et al. |
| 6,564,096 B2 | 5/2003 | Mest |
| 6,565,561 B1 | 5/2003 | Goble et al. |
| 6,603,997 B2 | 8/2003 | Doody |
| 6,620,155 B2 | 9/2003 | Underwood et al. |
| 6,641,580 B1 | 11/2003 | Edwards et al. |
| 6,669,685 B1 | 12/2003 | Rizoiu et al. |
| 6,678,552 B2 | 1/2004 | Pearlman |
| 6,702,810 B2 | 3/2004 | McClurken et al. |
| 6,752,802 B1 | 6/2004 | Isenberg et al. |
| 6,772,012 B2 | 8/2004 | Ricart et al. |
| 6,814,730 B2 | 11/2004 | Li |
| 6,904,303 B2 | 6/2005 | Phan et al. |
| 6,972,014 B2 | 12/2005 | Eum et al. |
| 7,001,378 B2 | 2/2006 | Yon et al. |
| 7,070,597 B2 | 7/2006 | Truckai et al. |
| 7,101,369 B2 | 9/2006 | van der Welde |
| 7,160,259 B2 | 1/2007 | Tardy et al. |
| 7,179,256 B2 | 2/2007 | Mest |
| 7,207,989 B2 | 4/2007 | Pike, Jr. et al. |
| 7,244,254 B2 | 7/2007 | Brace et al. |
| 7,270,659 B2 | 9/2007 | Ricart et al. |
| 7,311,703 B2 | 12/2007 | Turovskiy et al. |
| 7,387,625 B2 | 6/2008 | Hovda et al. |
| 7,387,630 B2 | 6/2008 | Mest |
| 7,412,273 B2 | 8/2008 | Jais et al. |
| 7,416,552 B2 | 8/2008 | Paul et al. |
| 7,468,057 B2 | 12/2008 | Ponzi |
| 7,507,222 B2 | 3/2009 | Cindrich et al. |
| 7,559,905 B2 | 7/2009 | Kagosaki et al. |
| 7,604,634 B2 | 10/2009 | Hooven |
| 7,666,166 B1 | 2/2010 | Emmert et al. |
| 7,879,030 B2 | 2/2011 | Paul et al. |
| 7,938,822 B1 | 5/2011 | Berzak et al. |
| 7,951,143 B2 | 5/2011 | Wang et al. |
| 7,993,335 B2 | 8/2011 | Rioux et al. |
| 8,128,620 B2 | 3/2012 | Wang et al. |
| 8,128,621 B2 | 3/2012 | Wang et al. |
| 8,273,082 B2 | 9/2012 | Wang et al. |
| 8,287,531 B2 | 10/2012 | Mest |
| 8,333,762 B2 | 12/2012 | Mest et al. |
| 8,369,922 B2 | 2/2013 | Paul et al. |
| 8,439,907 B2 | 5/2013 | Auth et al. |
| 8,444,638 B2 | 5/2013 | Woloszko et al. |
| 8,449,535 B2 | 5/2013 | Deno et al. |
| 8,515,560 B2 | 8/2013 | Debruyne et al. |
| 8,591,507 B2 | 11/2013 | Kramer et al. |
| 8,663,226 B2 | 3/2014 | Germain |
| 8,700,133 B2 | 4/2014 | Hann |
| 8,702,697 B2 | 4/2014 | Curley |
| 8,755,860 B2 | 6/2014 | Paul et al. |
| 8,758,349 B2 | 6/2014 | Germain et al. |
| 8,864,760 B2 | 10/2014 | Kramer et al. |
| 8,945,121 B2 | 2/2015 | Curley |
| 9,033,972 B2 | 5/2015 | Curley |
| 9,061,120 B2 | 6/2015 | Osypka et al. |
| 9,125,671 B2 | 9/2015 | Germain et al. |
| 9,138,287 B2 | 9/2015 | Curley et al. |
| 9,138,288 B2 | 9/2015 | Curley |
| 9,445,861 B2 | 9/2016 | Curley |
| 9,610,396 B2 | 4/2017 | Curley et al. |
| 9,730,748 B2 | 8/2017 | Curley |
| 9,743,984 B1 | 8/2017 | Curley et al. |
| 9,877,768 B2 | 1/2018 | Curley et al. |
| 9,937,000 B2 | 4/2018 | Curley |

(56) References Cited

U.S. PATENT DOCUMENTS

| | | |
|---|---|---|
| 10,022,176 B2 | 7/2018 | Curley |
| 10,058,385 B2 | 8/2018 | Curley |
| 10,307,201 B2 | 6/2019 | Curley |
| 10,448,987 B2 | 10/2019 | Curley |
| 10,548,654 B2 | 2/2020 | Curley |
| 2001/0031946 A1 | 10/2001 | Walker et al. |
| 2002/0120259 A1 | 8/2002 | Lettice et al. |
| 2002/0123749 A1 | 9/2002 | Jain |
| 2002/0153046 A1 | 10/2002 | Dantsker et al. |
| 2002/0183735 A1 | 12/2002 | Edwards et al. |
| 2003/0109871 A1 | 6/2003 | Johnson et al. |
| 2003/0120271 A1 | 6/2003 | Burnside et al. |
| 2004/0006336 A1 | 1/2004 | Swanson |
| 2004/0116922 A1 | 6/2004 | Hovda et al. |
| 2004/0133154 A1 | 7/2004 | Flaherty et al. |
| 2004/0220559 A1 | 11/2004 | Kramer et al. |
| 2004/0230190 A1 | 11/2004 | Dahla et al. |
| 2004/0260282 A1 | 12/2004 | Gough et al. |
| 2005/0015081 A1 | 1/2005 | Turovskiy et al. |
| 2005/0055019 A1 | 3/2005 | Skarda |
| 2005/0059963 A1 | 3/2005 | Phan et al. |
| 2005/0080410 A1 | 4/2005 | Rioux et al. |
| 2005/0165391 A1 | 7/2005 | Maguire et al. |
| 2005/0187599 A1 | 8/2005 | Sharkey et al. |
| 2005/0192652 A1 | 9/2005 | Cioanta et al. |
| 2005/0245923 A1 | 11/2005 | Christopherson et al. |
| 2005/0267552 A1 | 12/2005 | Conquergood et al. |
| 2006/0085054 A1 | 4/2006 | Zikorus et al. |
| 2006/0118127 A1 | 6/2006 | Chinn |
| 2006/0129091 A1 | 6/2006 | Bonnette et al. |
| 2006/0216275 A1 | 9/2006 | Mon |
| 2006/0241366 A1 | 10/2006 | Falwell et al. |
| 2006/0253183 A1* | 11/2006 | Thagalingam ..... A61B 18/1492 607/120 |
| 2006/0259024 A1 | 11/2006 | Turovskiy et al. |
| 2006/0276780 A1 | 12/2006 | Brace et al. |
| 2006/0287650 A1 | 12/2006 | Cao et al. |
| 2007/0027448 A1 | 2/2007 | Paul et al. |
| 2007/0032786 A1 | 2/2007 | Francischelli |
| 2007/0167775 A1 | 7/2007 | Kochavi et al. |
| 2007/0185483 A1 | 8/2007 | Butty et al. |
| 2007/0219434 A1 | 9/2007 | Abreu |
| 2007/0250056 A1 | 10/2007 | Vanney |
| 2007/0287998 A1 | 12/2007 | Sharareh et al. |
| 2007/0288075 A1 | 12/2007 | Dowlatshahi |
| 2008/0086073 A1 | 4/2008 | McDaniel |
| 2008/0154258 A1 | 6/2008 | Chang et al. |
| 2008/0161788 A1 | 7/2008 | Dando et al. |
| 2008/0161797 A1 | 7/2008 | Wang et al. |
| 2008/0167650 A1 | 7/2008 | Joshi et al. |
| 2008/0249463 A1 | 10/2008 | Pappone et al. |
| 2008/0275438 A1 | 11/2008 | Gadsby et al. |
| 2008/0275440 A1 | 11/2008 | Kratoska et al. |
| 2008/0281200 A1 | 11/2008 | Voic et al. |
| 2008/0288038 A1 | 11/2008 | Paul et al. |
| 2009/0069808 A1 | 3/2009 | Pike, Jr. et al. |
| 2009/0082837 A1 | 3/2009 | Gellman et al. |
| 2009/0093811 A1 | 4/2009 | Koblish et al. |
| 2009/0118725 A1 | 5/2009 | Auth et al. |
| 2009/0118727 A1 | 5/2009 | Pearson et al. |
| 2009/0163836 A1 | 6/2009 | Sliwa |
| 2009/0192507 A1 | 7/2009 | Luttich |
| 2009/0254083 A1 | 10/2009 | Wallace et al. |
| 2010/0030098 A1 | 2/2010 | Fojtik |
| 2010/0094272 A1 | 4/2010 | Rossetto et al. |
| 2010/0198056 A1 | 8/2010 | Fabro et al. |
| 2010/0292766 A1 | 11/2010 | Duong et al. |
| 2010/0324471 A1 | 12/2010 | Flaherty et al. |
| 2011/0060349 A1 | 3/2011 | Cheng et al. |
| 2011/0137150 A1 | 6/2011 | Connor et al. |
| 2011/0160726 A1 | 6/2011 | Ingle |
| 2011/0184403 A1 | 7/2011 | Brannan |
| 2011/0190756 A1 | 8/2011 | Venkatachalam et al. |
| 2011/0230799 A1 | 9/2011 | Christian et al. |
| 2011/0251615 A1 | 10/2011 | Truckai et al. |
| 2011/0270246 A1 | 11/2011 | Clark et al. |
| 2011/0282342 A1 | 11/2011 | Leo et al. |
| 2012/0108938 A1 | 5/2012 | Kauphusman et al. |
| 2012/0130381 A1 | 5/2012 | Germain |
| 2012/0165812 A1 | 6/2012 | Christian |
| 2012/0253188 A1 | 10/2012 | Holland |
| 2012/0265190 A1* | 10/2012 | Curley ................. F04B 41/02 606/28 |
| 2012/0265199 A1 | 10/2012 | Curley |
| 2012/0265200 A1 | 10/2012 | Curley |
| 2012/0265276 A1 | 10/2012 | Curley |
| 2012/0277737 A1 | 11/2012 | Curley |
| 2012/0310230 A1 | 12/2012 | Willis |
| 2014/0052117 A1 | 2/2014 | Curley |
| 2014/0058386 A1 | 2/2014 | Clark et al. |
| 2014/0188106 A1 | 7/2014 | Curley |
| 2014/0275977 A1 | 9/2014 | Curley et al. |
| 2014/0276743 A1 | 9/2014 | Curley |
| 2014/0276758 A1 | 9/2014 | Lawrence et al. |
| 2014/0350542 A1 | 11/2014 | Kramer et al. |
| 2015/0066025 A1 | 3/2015 | Curley |
| 2015/0223882 A1 | 8/2015 | Curley |
| 2015/0265344 A1* | 9/2015 | Aktas ................ A61B 18/1492 606/41 |
| 2015/0351823 A1 | 12/2015 | Curley |
| 2015/0359582 A1 | 12/2015 | Curley et al. |
| 2016/0278856 A1 | 9/2016 | Panescu et al. |
| 2016/0354138 A1 | 12/2016 | Curley |
| 2017/0238993 A1 | 8/2017 | Curley |
| 2017/0296739 A1 | 10/2017 | Curley et al. |
| 2017/0333107 A1 | 11/2017 | Curley |
| 2018/0042669 A1 | 2/2018 | Curley et al. |
| 2018/0140345 A1 | 5/2018 | Curley et al. |
| 2018/0185083 A1 | 7/2018 | Curley |
| 2019/0290349 A1 | 9/2019 | Curley |
| 2020/0015880 A1 | 1/2020 | Curley |
| 2020/0113614 A1 | 4/2020 | Curley |
| 2020/0138502 A1 | 5/2020 | Curley |

FOREIGN PATENT DOCUMENTS

| | | |
|---|---|---|
| CN | 1341462 A | 3/2002 |
| CN | 1119127 C | 8/2003 |
| CN | 1525839 A | 9/2004 |
| CN | 1897885 A | 1/2007 |
| CN | 2885157 Y | 4/2007 |
| CN | 101209217 A | 7/2008 |
| CN | 101578073 A | 11/2009 |
| CN | 101773699 A | 7/2010 |
| CN | 201642316 U | 11/2010 |
| CN | 101999931 A | 4/2011 |
| EP | 0 823 843 A1 | 2/1998 |
| EP | 0 895 756 A1 | 2/1999 |
| EP | 1 033 107 A1 | 9/2000 |
| EP | 1 159 036 A1 | 12/2001 |
| EP | 0 908 156 B1 | 11/2003 |
| EP | 2 042 112 A2 | 4/2009 |
| EP | 2 430 996 A2 | 3/2012 |
| JP | 62-211057 A | 9/1987 |
| JP | 01-146539 A | 6/1989 |
| JP | 05-212048 A | 8/1993 |
| JP | 10-505268 A | 5/1998 |
| JP | 11-178787 A | 7/1999 |
| JP | 2003-528684 A | 9/2003 |
| JP | 2008-534081 A | 8/2008 |
| JP | 62-097971 B2 | 3/2018 |
| WO | 96/07360 A1 | 3/1996 |
| WO | 96/34569 A1 | 11/1996 |
| WO | 96/36288 A1 | 11/1996 |
| WO | 97/29702 A1 | 8/1997 |
| WO | 98/29068 A1 | 7/1998 |
| WO | 99/20191 A1 | 4/1999 |
| WO | 99/32186 A1 | 7/1999 |
| WO | 02/089686 A1 | 11/2002 |
| WO | 03/028524 A3 | 10/2003 |
| WO | 03/096871 A2 | 11/2003 |
| WO | 2005/048858 A1 | 6/2005 |
| WO | 2005/089663 A1 | 9/2005 |
| WO | 2006/031541 A1 | 3/2006 |

(56) References Cited

FOREIGN PATENT DOCUMENTS

| WO | 2006/055658 | A1 | 5/2006 |
|---|---|---|---|
| WO | 2006/071058 | A1 | 7/2006 |
| WO | 2006/095171 | A1 | 9/2006 |
| WO | 2006/102471 | A2 | 9/2006 |
| WO | 2006/103951 | A1 | 10/2006 |
| WO | 2007/080578 | A2 | 7/2007 |
| WO | 2010/002733 | A1 | 1/2010 |
| WO | 2010/151619 | A2 | 12/2010 |
| WO | 2012/071058 | A1 | 5/2012 |

OTHER PUBLICATIONS

U.S. Appl. No. 16/660,212, filed Oct. 22, 2019, Methods and Devices for Controlling Ablation Therapy.
U.S. Appl. No. 16/673,305, filed Nov. 4, 2019, Systems and Methods for Visualizing Fluid Enhanced Ablation Therapy.
U.S. Appl. No. 16/720,581, filed Dec. 19, 2019, Devices and Methods for Remote Temperature Monitoring in Fluid Enhanced Ablation Therapy.
Brace CL. Microwave tissue ablation: biophysics, technology, and applications.; Crit Rev Biomed Eng. 2010;38 (1):65-78.
Chinese Office Action for Application No. 201280028609.9, dated May 27, 2015 (22 pages).
Chinese Office Action for Application No. 201280028611.6, dated Jul. 29, 2015 (23 pages).
Chinese Office Action for Application No. 201280028612.0, dated Nov. 2, 2016 (8 pages).
Chinese Office Action for Application No. 201710537279.0, dated Apr. 3, 2019 (8 pages).
Chinese Office Action for Application No. 201280028621.X, dated Jul. 31, 2015 (18 pages).
Chinese Office Action for Application No. 201380053690.0, dated Sep. 30, 2016 (17 pages).
Chinese Office Action for Application No. 201380053690.0, dated Jul. 20, 2017 (18 pages).
Chinese Office Action for Application No. 2016112115279.0, dated Nov. 30, 2018 (25 pages).
Extended Search Report and Written Opinion for EP 12770537.4 dated Oct. 10, 2014 (6 pages).
Extended Search Report and Written Opinion for EP 12770631.5 dated Oct. 1, 2014.
Extended Search Report and Written Opinion for EP 12771331.1 dated Sep. 25, 2014.
Extended European Search Report and Written Opinion for Application No. 12771601.7 dated Oct. 27, 2014 (7 pages).
European Office Action for Application No. 12771601.7, dated Jun. 13, 2018 (5 pages).
Extended Search Report and Written Opinion for EP 12771876.5 dated Oct. 13, 2014 (6 pages).
European Office Action for Application No. EP 12771876.5, dated May 31, 2018 (6 pages).
Extended European Search Report and Search Opinion for Application No. 13829821.1 dated Mar. 17, 2016 (7 pages).
Extended European Search Report and Search Opinion for Application No. 19151775.4 dated May 21, 2019 (8 pages).
International Search Report and Written Opinion for Application No. PCT/US2012/033203, dated Sep. 21, 2012. (23 pages).
International Search Report and Written Opinion for Application No. PCT/US2012/033213, dated Sep. 21, 2012. (17 pages).
International Search Report and Written Opinion for Application No. PCT/US2012/033216, dated Sep. 21, 2012. (17 pages).
International Search Report and Written Opinion for Application No. PCT/US2012/033327, dated Sep. 21, 2012. (14 pages).
International Search Report and Written Opinion for Application No. PCT/US2012/033332, dated Sep. 21, 2012. (20 pages).
International Search Report and Written Opinion for Application No. PCT/US2013/053977, dated Nov. 14, 2013. (20 pages).
International Search Report and Written Opinion for Application No. PCT/US2014/024731, dated Jul. 21, 2014 (39 pages).
International Invitation to Pay Additional Fees for Application No. PCT/US2017/044706, dated Oct. 5, 2017 (2 Pages).
International Search Report and Written Opinion for Application No. PCT/US2017/044706, dated Nov. 29, 2017 (25 pages).
Japanese Office Action for Application No. 2014-505263, dated Jan. 26, 2016 (4 pages).
Japanese Office Action for Application No. 2014-505266, dated Feb. 23, 2016 (7 pages).
Japanese Office Action for Application No. 2017-151156, dated Aug. 7, 2018 (11 pages).
Japanese Office Action for Application No. 2017-151156, dated Apr. 16, 2019 (23 pages).
Japanese Office Action for Application No. 2017-207454, dated Oct. 2, 2018 (6 pages).
Japanese Office Action for Application No. 2018-029767, dated Sep. 4, 2018 (5 pages).
David R. Lide (ed)., CRC Handbook of Chemistry and Physics, 87th Edition. 2006. p. 8-81. CRC Press, Florida.
Nath et al., Prog. Card. Dis. 37(4):185-204 (1995).
Rolf Sander, Compilation of Henry's Law Constants for Inorganic and Organic Species of Potential Importance in Environmental Chemistry. Max-Planck Institute of Chemistry. 1999, Mainz Germany. Www.henrys-law.org.
Sapareto et al., Int. J Rad. One. Biol. Phys. 10(6):787-800 (1984).
Young, S.T., et al., An instrument using variation of resistance to aid in needle tip insertion in epidural block in monkeys. Med Instrum. Oct. 1987;21(5):266-8. Abstract Only.
Chinese Office Action for Application No. 201280028620.5, dated May 27, 2015. (26 pages).
Chinese Office Action for Application No. 201611215279.0, dated Aug. 12, 2019. (21 pages).
International Search Report and Written Opinion for Application No. PCT/US19/30645, dated Jul. 22, 2019 (14 pages).
Extended European Search Report for Application No. 20184347.1 dated Feb. 1, 2021 (8 pages).

\* cited by examiner

SELECTIVELY DEPLOYABLE CATHETER ABLATION DEVICES

FIELD

This disclosure relates generally to surgical instruments and, more particularly, to catheters having deployable instruments for use in surgical procedures.

BACKGROUND

Catheters are widely utilized in surgical procedures for delivering instruments and medicines to a particular position within a patient's body. For example, catheters can be introduced into a patient's circulatory system and navigated to various regions of the body (e.g., the heart) through the patient's blood vessels. The use of a catheter can provide for a more minimally invasive procedure than would otherwise be necessary to access the interior of the patient's body.

In order to allow navigation of the often tortuous pathways of, e.g., a patient's circulatory system, catheters can include components to allow them to be steered from outside the patient's body as they are advanced toward a surgical site. There are a variety of known mechanisms for steering a catheter, but most include the use of one or more steering cables that pass longitudinally through a sidewall of the catheter from a distal portion thereof to a handle or other control assembly outside the patient's body. Pushing or pulling on the one or more steering cables can cause the catheter to bend in one direction or another.

Catheters can be utilized to deliver any of a variety of surgical instruments during an operation. One common example is a deployable elongate body, such as a needle, that can be configured to penetrate into tissue at a treatment site and deliver therapeutic fluid, energy, etc. The deployable needle can be slidably disposed within an inner lumen of the catheter and can be retracted into a distal portion of the catheter during delivery to the surgical site. It can then be selectively deployed after the catheter is positioned at the surgical site.

The selective retraction and deployment of the needle, other elongate body, or other surgical instrument is typically enabled by connecting the needle (e.g., via a connecting member, such as a flexible and a substantially incompressible tube) to the handle or other control assembly that is outside the patient's body. A user can control the position of the needle at the distal end of the catheter by manipulating the portion of the needle (or connecting member) that is accessible at the handle or control assembly. As a result, the position of the needle relative to the catheter is set at a proximal end of the device.

One problem encountered in these devices is inadvertent deployment of the needle, other elongate body, or other surgical instrument due to shortening of the catheter during steering. As noted above, steering of the catheter is accomplished by pushing or pulling on one or more wires extending through a sidewall of the catheter. This operation causes a portion of the catheter to retract or compress to change direction, thereby shortening its overall length. This shortening occurs along a distal portion of the catheter but, as mentioned above, the position of the needle or other elongate body relative to the catheter is set at the proximal end of the device. As a result, the floating distal tip of the needle within the inner lumen of the catheter can become exposed as the distal portion of the catheter compresses and bends.

Inadvertent exposure of a needle, other elongate body, or other instrument configured to penetrate tissue can cause complications during a surgical procedure. For example, an exposed needle can unintentionally damage tissue as the catheter is steered into position at a surgical site.

Relative movement between the catheter and needle during steering also makes it difficult for users to know precisely how far the needle or other elongate body has been extended from a distal end of the catheter once it is positioned at a surgical site. This is because, again, the position of the needle relative to the catheter is set at a proximal end of the device outside the patient's body. The position can initially be set such that the needle is recessed into the catheter inner lumen by a specific amount before any steering takes place, but a user cannot know how the needle has moved relative to the distal end of the catheter while advancing the needle when the catheter is in a steered state. The user therefore cannot precisely control the advancement of the needle at the surgical site (e.g., to extend the needle from the distal end of the catheter by a specific distance, etc.).

Prior attempts to address these issues have focused on recessing a needle or other elongate body further within a catheter inner lumen in order to prevent inadvertent exposure of the needle tip during steering. This is problematic, however, because it creates a longer distal portion of the catheter that is distal of any steering mechanism and houses the elongate body or other instrument, making the catheter less maneuverable. In addition, it does nothing to address the problem of precisely deploying the needle after it is positioned at a surgical site. Other attempts to address these issues have involved adding stiff support wires into the catheter to make it less compressible, but this also compromises the catheter's steering performance.

Accordingly, there is a need for improved devices and methods for selectively deploying catheter needles or other surgical instruments. In particular, there is a need for improved devices and methods that guard against inadvertent exposure of such instruments during catheter steering and allow for more precise extension of such instruments once a catheter is positioned at a surgical site.

SUMMARY

The present disclosure generally provides devices and methods for selectively deploying catheter needles or other surgical instruments that address, among other things, the above-described needs in the art. The devices and methods described herein generally include proximally biasing a deployable needle or other surgical instrument such that a portion of the needle or other instrument is held against a retraction stop coupled to the catheter. The retraction stop can be formed at a position near the distal end of the catheter such that a precise position of the needle or other instrument relative to the distal end of the catheter can be maintained, despite even severe steering of the catheter. The devices and methods described herein can further include an advancing mechanism that can selectively urge the needle or other instrument distally against the biasing force to deploy the instrument from the distal end of the catheter. As a result, the devices and methods described herein can prevent inadvertent deployment of an instrument carried within a catheter during steering operations and can allow for precise deployment of the instrument once a catheter is positioned at a surgical site.

In one aspect, a catheter is provided that includes an instrument slidably disposed within an inner lumen of the catheter, the instrument being coupled to at least one protrusion. The catheter can further include a retraction stop coupled to the catheter proximal to the at least one protrusion. There can also be a biasing element coupled to the instrument and configured to urge the instrument proximally such that the at least one protrusion abuts against the retraction stop. The catheter can further include an advancing mechanism configured to selectively engage the instrument and urge the instrument distally relative to the catheter.

The catheter described above can have a variety of modifications and/or additional features that are within the scope of the present disclosure. For example, in some embodiments, the catheter can be steerable using one or more control cables extending through the catheter. The one or more control cables can, in some embodiments, terminate at a position proximal to the retraction stop. This can prevent a distal portion of the catheter beyond the retraction stop from deforming during steering, such that no shortening of the distal portion occurs during steering of the catheter.

In some embodiments, the advancing mechanism can include a tab or other user-actuated handle coupled to a proximal portion of the instrument. The tab or handle can be rigidly coupled to the instrument in some embodiments. In other embodiments, the advancing mechanism can include a clutch to selectively engage the instrument. For example, in the case of a needle the clutch can engage the needle—or an intermediate component coupled to the needle—when a user desires to deploy the needle from the catheter inner lumen. When deployment is not desired, the clutch can disengage from the needle or intermediate component, thereby allowing the needle to be drawn proximally against the retraction stop by the biasing element. In certain embodiments, the clutch can be positioned in a proximal portion of the catheter within a handle assembly. Still further, in some embodiments the advancing mechanism can include one or more predetermined distance increments that can be selected to urge the instrument distally by the predetermined distance.

In certain embodiments, the catheter can include at least one indicator light configured to activate when the advancing mechanism engages the instrument, thereby warning a user that the instrument may be extending from a distal end of the catheter or may be capable of inadvertent deployment since the instrument's position within the catheter is no longer controlled by the biasing element. The indicator light can be employed upon activation of a clutch, movement of a tab or handle, or actuation of any other kind of advancing mechanism.

The biasing element can, in some embodiments, also be positioned in a proximal portion of the catheter within the handle assembly. In other embodiments, however, it can be positioned at a distal end of the catheter. The biasing element can have a variety of forms and can be configured to either push or pull the instrument—or an intermediate component coupled to the instrument—toward a proximal end of the catheter.

In certain embodiments, the retraction stop can be positioned such that a distal tip of the instrument is proximal to a distal tip of the catheter when the at least one protrusion is abutting against the retraction stop. In other embodiments, the retraction stop can be positioned such that the distal tip of the instrument is even with the distal tip of the catheter when the at least one protrusion is abutting against the retraction stop. Such positioning can ensure that the distal end of the instrument cannot damage tissue as the catheter is steered or otherwise moved through the body. In addition, the advancing mechanism can be configured to advance the instrument distally such that the distal tip of the instrument is distal to the distal tip of the catheter. In other words, the biasing element can ensure the instrument is recessed within the catheter inner lumen until the advancing mechanism is utilized to extend the instrument from the catheter.

In some embodiments, the at least one protrusion can include one or more fluid channels formed therein to allow fluid flow there-through. This can allow the inner lumen of the catheter to be flushed clean of bodily fluid or other contaminants during use. The fluid passages can have a variety of shapes and sizes, ranging from a single channel to a plurality of channels extending over the at least one protrusion.

In another aspect, an ablation device is provided that includes a catheter having an inner lumen extending therethrough, the inner lumen including a retraction stop formed on a distal portion thereof. The ablation device can further include a needle slidably disposed within the inner lumen of the catheter, the needle including an inner lumen, at least one outlet port formed on a distal portion thereof, and at least one protrusion formed on an outer surface thereof proximal to the at least one outlet port and distal to the retraction stop on the catheter inner lumen. The ablation device can also include an ablation element disposed on the distal portion of the needle and configured to ablate tissue, as well as a biasing element coupled to the needle and configured to urge the needle proximally such that the at least one protrusion on the needle abuts against the retraction stop on the catheter inner lumen. Still further, the ablation device can include an advancing mechanism configured to selectively urge the needle distally relative to the catheter.

Similar to the catheter described above, the ablation device can have a variety of modifications and/or additional features, all of which are considered within the scope of the present disclosure. For example, in certain embodiments the catheter of the ablation device can be steerable using one or more cables extending through the catheter. In other embodiments, the biasing element can be positioned in a proximal portion of the catheter within a handle assembly.

In other embodiments, the advancing mechanism can include a clutch to selectively couple to the needle, or to an intermediate component coupled to the needle. In certain embodiments, the clutch can be positioned in a proximal portion of the catheter within a handle assembly.

In still other embodiments, the retraction stop can be positioned such that a distal tip of the needle is proximal to a distal tip of the catheter when the at least one protrusion is abutting against the retraction stop. In other embodiments, the retraction stop can be positioned such that the distal tip of the needle is even with the distal tip of the catheter when the at least one protrusion is abutting against the retraction stop. Further, in some embodiments the advancing mechanism can be configured to advance the needle such that the distal tip of the needle is distal to the distal tip of the catheter. Still further, in some embodiments the at least one protrusion on the needle can include one or more fluid channels formed therein to allow fluid flow there-through.

In certain embodiments, the ablation device can further include at least one heating element disposed within the inner lumen of the needle and positioned within the distal portion thereof proximal to the at least one outlet port. The at least one heating element can be configured to heat fluid flowing through the inner lumen of the needle.

In another aspect, a method for selectively deploying an instrument from a catheter is provided that includes urging an instrument slidably disposed within an inner lumen of a catheter toward a proximal end of the catheter such that at least one protrusion coupled to the instrument abuts against a retraction stop coupled to a distal portion of the catheter. The method further includes coupling an advancing mechanism to the instrument to control movement of the instrument within the catheter, and actuating the advancing mechanism to urge the instrument distally relative to the catheter.

In some embodiments, urging the instrument distally relative to the catheter can include advancing the instrument from a first position wherein a distal tip of the instrument is proximal to a distal tip of the catheter to a second position wherein the distal tip of the instrument is distal to the distal tip of the catheter. In other embodiments urging the instrument distally relative to the catheter can include advancing the instrument from a first position wherein a distal tip of the instrument is even with a distal tip of the catheter to a second position wherein the distal tip of the instrument is distal to the distal tip of the catheter. Note that any number of additional positions can be included as well to provide varying distances by which the instrument extends distally of the catheter.

In certain embodiments, the method can further include steering the catheter into position within a patient's body. This can be done, for example, using the one or more control cables described above.

In still other embodiments, the instrument can be a needle and the method can further include delivering fluid into tissue through an inner lumen of the needle and at least one outlet port formed in a distal portion of the needle. In still other embodiments, the method can further include heating the fluid delivered into tissue using a heating element positioned within the inner lumen of the needle proximal to the at least one outlet port. The method can also include delivering ablative energy into tissue from an ablation element disposed on the distal portion of the needle.

In certain embodiments, the method can further include activating at least one indicator light upon coupling the advancing mechanism to the instrument. Such an indicator light can provide feedback to a user that the instrument may be extending from the distal end of the catheter or may be capable of inadvertent deployment during, for example, catheter steering, etc.

In another aspect, a catheter is provided that can include an instrument slidably disposed within an inner lumen of the catheter, the instrument being coupled to at least one protrusion. The catheter can further include a retraction stop coupled to the catheter, as well as a deployment stop coupled to the catheter and disposed distal to the retraction stop. The catheter can further include an advancing mechanism configured to move the instrument relative to the catheter between a first position, wherein the at least one protrusion contacts the retraction stop, and a second position, wherein the at least one protrusion contacts the deployment stop.

As with the above-described aspects and embodiments, a number of variations and/or substitutions are possible. In some embodiments, for example, the deployment stop can be a distal end of a groove formed in a sidewall of the catheter that is configured to receive the at least one protrusion. In certain embodiments, the catheter can further include a second deployment stop at a distal end of a second groove formed in the sidewall of the catheter. In such embodiments, rotation of the instrument about a longitudinal axis thereof can select which groove receives the at least one protrusion. In some embodiments, the groove can be tortuous and can include a plurality of longitudinally-extending portions connected by at least one transition. In such embodiments, any of proximal and distal translation of the instrument can move the at least one protrusion through one of the plurality of longitudinally-extending portions and rotation of the instrument can move the at least one protrusion through the at least one transition.

In some embodiments, the deployment stop can be a bulkhead having a through-hole formed therein to receive the at least one protrusion. Further, the at least one protrusion and the through-hole can have complementary shapes to permit passage of the at least one protrusion through the through-hole in a first orientation and prevent passage of the at least one protrusion through the through-hole in a second orientation.

In certain embodiments, a position of the deployment stop relative to the retraction stop can be adjusted. For example, in some embodiments the deployment stop can be coupled to an intermediate shaft disposed within the inner lumen of the catheter about the instrument. Movement of the intermediate shaft relative to the catheter, e.g., by threaded coupling, etc., can adjust a position of the deployment stop relative to the retraction stop.

In still further embodiments, the deployment stop can be a detent formed in a sidewall of the catheter and the at least one protrusion can be biased to extend into the detent when aligned therewith. In some embodiments, the catheter can include additional deployment stops to permit different distances of instrument advancement or retraction relative to the catheter.

In some embodiments, the catheter can further include a biasing element coupled to the instrument. Such an element is not required where, for example, both retraction and deployment stops are utilized to control movement of the instrument relative to the catheter, but can optionally be employed.

Any of the features or variations described above can be applied to any particular aspect or embodiment of the present disclosure in a number of different combinations. The absence of explicit recitation of any particular combination is due solely to the avoidance of repetition in this summary.

BRIEF DESCRIPTION OF THE DRAWINGS

The aspects and embodiments of the present disclosure described above will be more fully understood from the following detailed description taken in conjunction with the accompanying drawings, in which.

DETAILED DESCRIPTION

Figure 1:
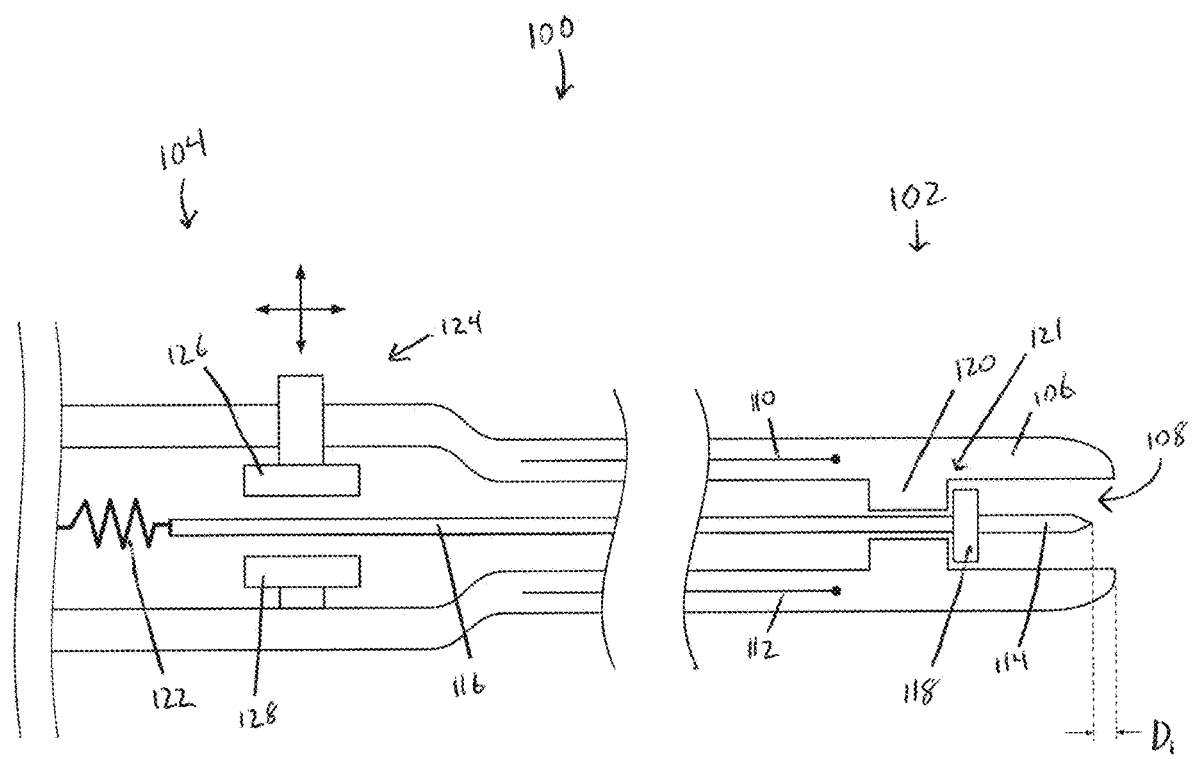
FIG. 1 is an illustration of one embodiment of a catheter device having a selectively deployable instrument.

Certain exemplary embodiments will now be described to provide an overall understanding of the principles of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present disclosure.

As mentioned above, catheters having selectively deployable surgical instruments (e.g., elongate bodies like needles, etc.) are commonly used in medicine today. Further, the catheters carrying these instruments are often steerable using one or more wires extending through a sidewall of the catheter that can be pushed or pulled to change the direction of the catheter. The steering action, however, shortens the length of the catheter and can result in inadvertent protrusion of a needle or other instrument from the distal end of the catheter. This is due to the fact that the needle or other instrument is referenced to the catheter body only at a proximal end of the device, typically outside the patient's body. Along a distal portion of the catheter, where the shortening is occurring due to bending and compression, the needle floats freely and often does not experience the same shortening as the catheter sidewall. Inadvertent protrusion of the needle or other instrument tip from the catheter distal end can damage surrounding tissue.

Furthermore, it can be difficult to determine with precision the position of a needle or other instrument relative to the distal end of the catheter once it is in position. This is, again, because the relative positions of the instrument and catheter are set only at a proximal end of the device outside a patient's body. This setting can indicate a precise position of the needle or other instrument relative to the catheter distal end when in an un-steered configuration, but the movement of the distal portion of the catheter and needle during steering can change their relative positions. As a result, a surgeon or other user cannot tell with certainty that extending a needle or other instrument by a particular distance (e.g., 5 mm) at a proximal end of the device will result in the instrument actually extending from the distal end of the catheter by that distance. Lack of precision and accuracy in extending a needle or other instrument from the distal end of a catheter can also result in complications, as the tissue at the surgical site may be extremely thin, etc.

The devices and methods described herein address these and other shortcomings of prior designs by providing a reference datum for the needle or other surgical instrument that is positioned along a distal portion of the catheter. The needle or other instrument can include a feature configured to interface with a retraction stop formed along a distal portion of the catheter, thereby creating a datum position where the relation of the distal tips of the needle or other instrument and catheter are known. This datum position can be located distal to any steering mechanism, such that any flexibility (i.e., possible shortening due to steering) in the catheter body occurs proximally to the datum position. Accordingly, whenever the needle or other instrument is drawn against the retraction stop of the catheter at the datum position, the relative positions of the needle or other instrument and catheter along a distal-most portion of the catheter are known with certainty.

In order to ensure that the relative positions of the needle or other surgical instrument and catheter do not change during steering operations, the needle or other surgical instrument can be proximally biased. Once the catheter is in position at a surgical site, the needle or other surgical instrument can be selectively advanced distally against the biasing force using an advancing mechanism that can selectively engage the needle, e.g., using a clutch mechanism.

FIG. 1 illustrates one embodiment of a catheter device 100 having a selectively deployable instrument (a needle in this embodiment) according to the teachings of the present disclosure. The device 100 can be generally divided into a distal portion 102 that is positioned within a patient's body and a proximal portion 104 that remains outside the patient's body and is manipulated by a surgeon or other user. The catheter device 100 includes a sidewall 106 and inner lumen 108. The distal portion 102 can be steerable using cables 110, 112 that extend through the sidewall 106. For example, the distal portion 102 could be directed toward the bottom of the figure by pulling proximally on the bottom cable 112.

An elongate body, e.g., a needle 114, can be positioned within the inner lumen 108 of the catheter distal portion 102. The needle 114 can extend the entire length of the catheter device 100, or can be coupled to a connecting member 116 that extends between the needle 114 and the proximal portion 104 of the device. The needle 114 can also have formed thereon (or formed on a portion of the connecting member 116) one or more protrusions 118, such as a flange, rib, ledge, shoulder, etc. The protrusion 118 can be positioned distally of a retraction stop 120, such as a corresponding flange, rib, ledge, shoulder, or other feature, that is formed on a sidewall of the catheter inner lumen 108. The protrusion 118 and the retraction stop 120 can be configured such that the protrusion cannot pass proximally through the retraction stop, but instead abuts against it. Moreover, the retraction stop 120 can be positioned distally of a distal end of the steering cables 110, 112, thereby ensuring that any flexing of the distal portion 102 during steering occurs proximally of the retraction stop 120.

Given that the protrusion 118 is formed on the needle 114 (or, e.g., formed on the connecting member 116 and therefore coupled to the needle) and the retraction stop 120 is formed on the sidewall of the inner lumen 108 (or, e.g., formed on another component and coupled to the catheter) at particular locations, the relative positions of the distal tip of the needle 114 and the distal tip of the device 100 are known whenever the protrusion 118 is drawn against the retraction stop 120 at a distally-located datum position 121. A biasing element 122 can urge the needle 114 and connecting member 116 toward a proximal end of the device 100. This can ensure that the protrusion 118 remains pressed against the retraction stop 120 at the datum position 121, even if the overall length of the catheter device 100 shrinks due to steering during use.

The catheter device 100 also includes an advancing mechanism 124 that can be used to selectively urge the needle 114 or other instrument distally relative to the catheter. The advancing mechanism 124 can have a variety of forms, but in some embodiments can include a clutch mechanism to selectively couple to the needle 114 or a connecting member 116 coupled thereto only when deployment of the needle is desired. For example, FIG. 1 shows the advancing mechanism 124 as including an upper clutch member 126 and a lower clutch member 128. During steering operations or other times when deployment of the needle 114 is undesirable, the clutch members 126, 128 can remain separated and out of contact with the needle 114 or connecting member 116 if present. As a result, the biasing element 122 can urge the needle 114 proximally such that the protrusion 118 abuts against the retraction stop 120.

When deployment of the needle 114 from the distal end of the catheter device 100 is desired, the advancing mechanism 124 can be actuated such that the clutch members 126, 128 move toward one another to contact and securely grip the needle 114 or connecting member 116 if present. The clutch members 126, 128 can then be translated distally while gripping the needle 114 or connecting member 116 to urge the needle 114 distally against the force of the biasing element 122. Because the advancing mechanism 124 engages the needle 114 or connecting member 116 while the protrusion 118 is abutting against the retraction stop 120 (i.e., at the distally-located datum position 121), the position of the needle relative to the catheter distal tip is known with precision at all times.

In some cases, it can be desirable to position the protrusion 118 along the needle 114 and/or connecting member 116 such that, when in the fully retracted position, the distal tip of the needle is even with a distal end of the distal portion 102. In other embodiments, it can be desirable to position the protrusion 118 such that the distal tip of the needle is recessed within the inner lumen 108 by a distance Di when in the fully retracted position. If a gap distance Di is utilized, a user can be informed that the advancing mechanism 124 must be moved the desired extension distance plus the gap distance. Alternatively, gradations marked on an outer surface of the proximal portion 104 of the device, or other indications of the needle deployment distance, can be calibrated to include the gap distance Di, as well as any elongation of the connecting member 116 and compression of the catheter sidewall 106.

After use of the needle 114 or other surgical instrument is complete, the advancing mechanism can be retracted proximally to draw the needle 114 back into the inner lumen 108 of the catheter. Alternatively, the clutch members 126, 128 can be disengaged (i.e., moved away from one another) and the force of the biasing element 122 can retract the needle 114 to the datum position 121 where the protrusion 118 abuts against the retraction stop 120.

A catheter device like the one shown in FIG. 1 can have a number of advantages. For example, the device solves problems associated with referencing the relative positions of the catheter and deployable needle or other instrument from a position near the proximal end of the device. Instead, a datum position near a distal end of the device is utilized (i.e., distal of any portion of the device that flexes or articulates during steering) and the deployable needle or instrument is proximally biased to ensure that it is located at the datum position. This eliminates uncertainty regarding the position of the needle and allows for precise deployment once the catheter is positioned at a surgical site.

In addition, the use of an advancing mechanism having a selectively engageable clutch ensures that there is no unintentional movement of the needle or other instrument when the clutch is disengaged. Moreover, there is no need to form special interfacing features on the connecting member or portion of the needle body that extends into the proximal portion of the device, as the clutch can be configured to securely grip any portion thereof when actuated. Such a device can safely ensure that there is no inadvertent needle or other instrument deployment during even the most severe steering maneuvers, and can also provide for precise deployment control from outside a patient's body after the catheter is navigated into position. In certain embodiments, however, interfacing features can be employed to facilitate coupling of a connecting member and an advancing mechanism, such as a selectively engageable clutch.

Of course, the catheter device depicted in FIG. 1 is just one of a variety of possible configurations considered within the scope of the present disclosure. For example, the protrusion 118 and retraction stop 120 can have any of a variety of complementary forms, including full or partial circumference flanges, shoulders, or ledges, as well as one or more bumps, ribs, or other formations that can abut against one another to halt further proximal motion of the needle 114 beyond the datum position. Similarly, the biasing element 122 used to urge the needle 114 proximally can be a coil or other type of tension spring positioned along a proximal or distal portion of the device, or a compression spring similarly positioned along a proximal or distal portion of the device. Other known forms of biasing elements can be utilized as well, including, for example, electromagnetic biasing assemblies.

The advancing mechanism can have any of a variety of different configurations as well. For example, the advancing mechanism can be a very simple mechanism such as a protruding tab or handle that is formed on the connecting member 116 (or needle body if the needle extends the entire length of the device) and simply translates proximally or distally along with the needle 114. In such a configuration, the advancing mechanism should have sufficient clearance so that it does not reach a proximal stop (e.g., a proximal end of a slot formed in a device housing through which the tab or handle extends) prior to the needle 114 reaching the datum position 121 in response to force from the biasing element 122, as this could prevent determination of the precise position of the needle relative to a distal end of the catheter.

In still other embodiments, the advancing mechanism can include any of a variety of different clutch mechanisms known in the art to facilitate selectively engaging with the connecting member 116 or needle 114. These can include mechanical clutch mechanisms that physically grip the connecting member 116 or needle 114, electromagnetic clutch mechanisms that impart a force on the connecting member or needle without physically touching it, or other mechanisms known in the art.

Still further, any of a variety of known mechanisms for urging the needle 114 distally against the force of the biasing element 122 can be utilized. These can range from the simple application of a translating distal force by a user, as described in connection with FIG. 1, to the use of various gear, belt, or rack drive systems, or the use of an electrically-actuated solenoid, etc.

Figure 2:
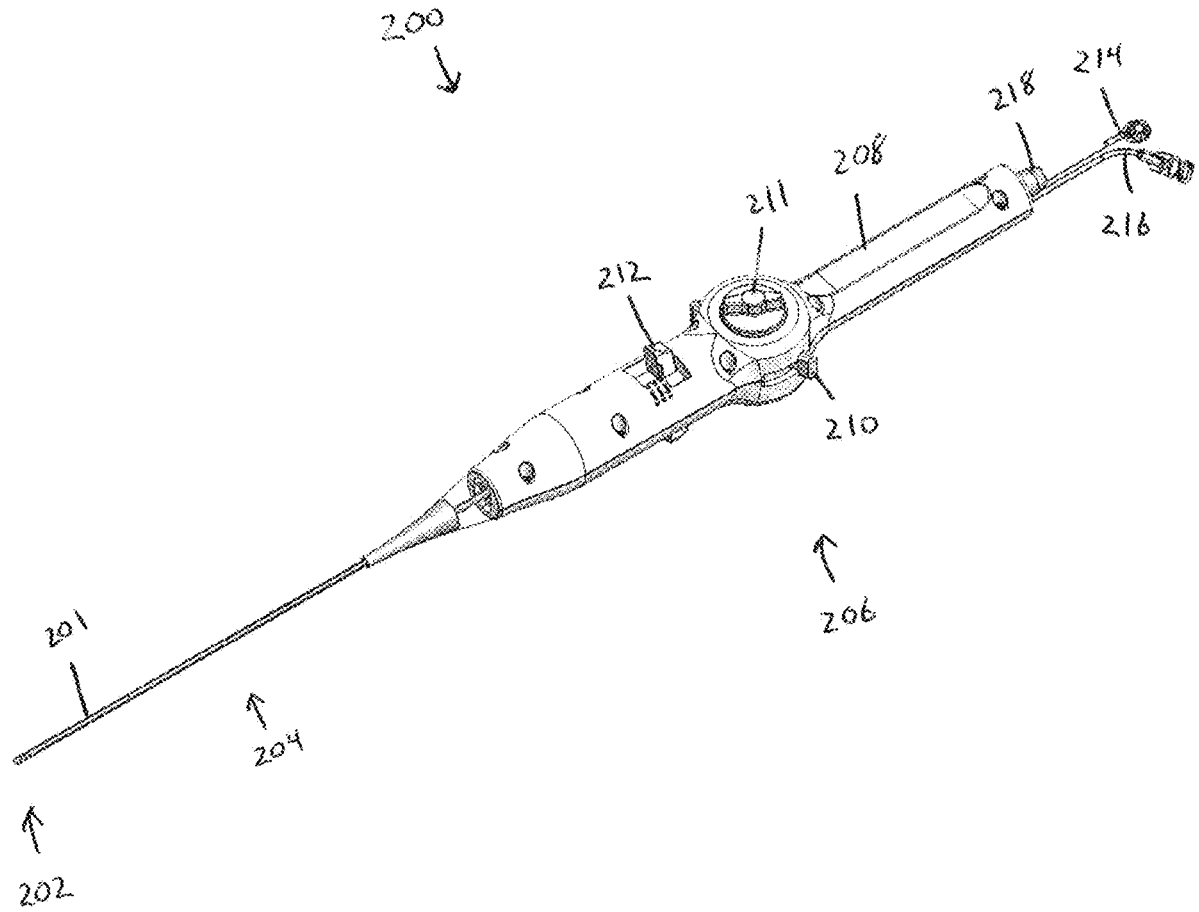
FIG. 2 is a perspective view of another embodiment of a catheter device having a selectively deployable instrument.
Figure 3:
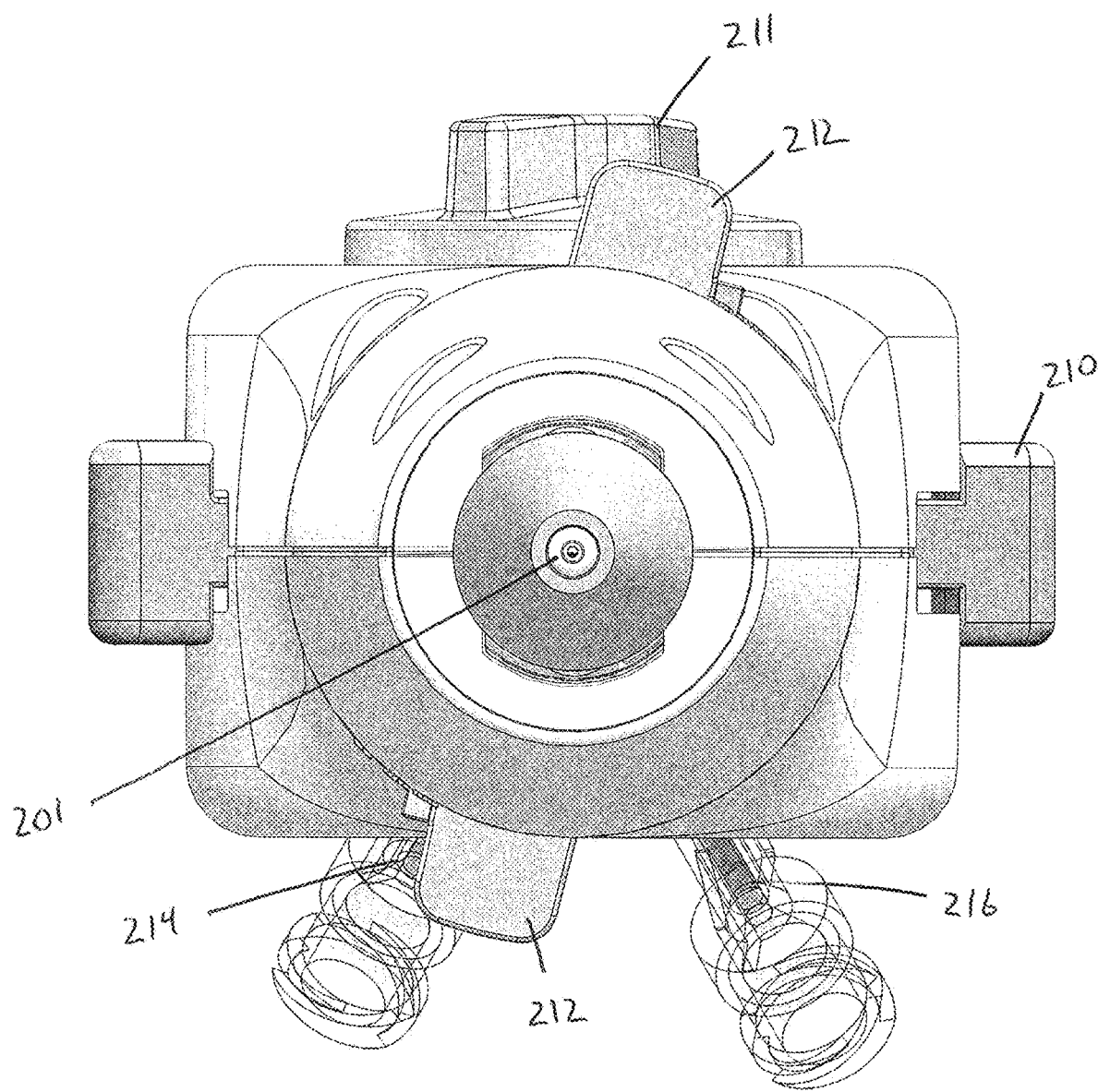
FIG. 3 is a front view of the catheter device of FIG. 2.

FIGS. 2 and 3 illustrate an alternative embodiment of a catheter device 200 having a selectively deployable instrument at its distal end. While the devices and methods described herein can be used with any of a variety of surgical catheter devices, the device 200 is configured to deliver fluid enhanced ablation therapy to, for example, a user's heart. Fluid enhanced ablation therapy involves the delivery of therapeutic energy (e.g., radio frequency electrical energy) concurrently with the delivery of therapeutically heated saline (e.g., saline above about 40° C.) or other fluid to selectively destroy tissue. The therapy can be used to treat a variety of medical conditions, including, for example, cardiac dysrhythmias, such as ventricular tachycardia. More information on fluid enhanced ablation therapy can be found in U.S. Pat. No. 6,328,735, entitled "Thermal Ablation System," U.S. Pat. No. 8,702,697, entitled "Devices and Methods for Shaping Therapy in Fluid Enhanced Ablation," and U.S. Patent Publication No. 2012/0265199, entitled "Methods and Devices for Use of Degassed Fluids with Fluid Enhanced Ablation Devices." The entire contents of these publications are hereby incorporated by reference as if they were reprinted here.

The device 200 generally includes a catheter 201 having a distal portion 202 and a flexible portion 204. A proximal portion 206 of the device includes a handle 208, steering controls 210, steering tension knob 211, and advancing mechanism 212. Extending from a proximal end of the device are tubes 214, 216 that receive fluid for delivery during therapy and instrument flushing, respectively. An additional inlet 218 at the proximal end of the device can receive any number of electrical power and control cables.

The device 200 can have a variety of different sizes depending on its intended use. For example, in some embodiments the catheter 201 can have a length of about 120 cm and a diameter of about 8 French ("French" is a unit of measure used in the catheter industry to describe the size of a catheter and is equal to three times the diameter of the catheter in millimeters). Such a catheter can be well suited to introduction into a patient's heart via the circulatory system. The catheter can be formed from any of a variety of materials known in the art, including, for example, polyurethanes, nylons, and polyether amides, such as PEBAX®. The catheter 201 can be flexible to allow for steering through tortuous pathways within the body using one or more steering cables, as described in more detail below.

The proximal portion 206 of the device 200 can also have a variety of different shapes and sizes. For example, in some embodiments, the overall length of the proximal portion 206 can be about 25 cm and both the width and height can be about 5 cm (given the various dimensions recited above, it should be clear that the figures are not necessarily to scale, especially with regard to the length of the catheter 201). The various components of the proximal portion 206 can be formed from a variety of materials known in the art, including, for example, various metals and polymers.

Figure 4:
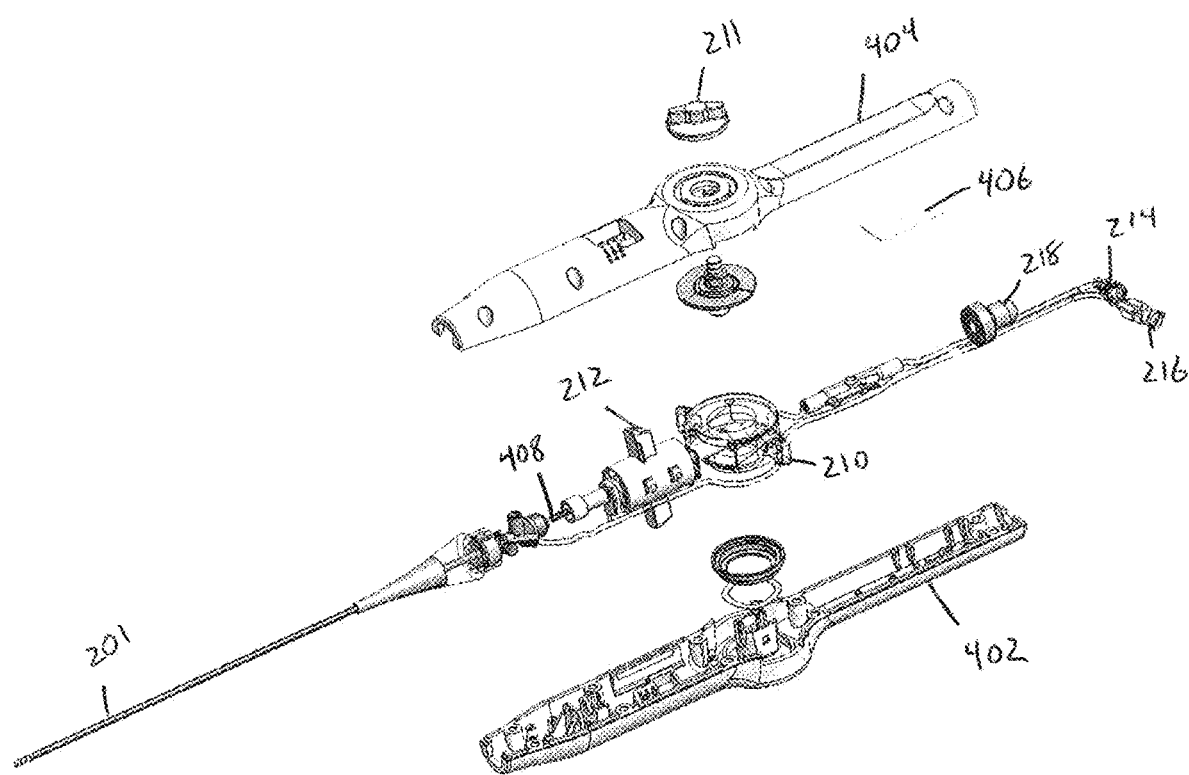
FIG. 4 is an exploded view of the catheter device of FIG. 2.

FIG. 4 illustrates an exploded view of the proximal portion 206 of the device 200. Visible in this figure is the lower housing 402 of the handle 208, upper housing 404, printed circuit board 406, catheter steering controls 210, and the advancing mechanism 212. Also shown in the figure is a connecting member 408 (which can be an embodiment of the above-described connecting member 116) that extends through the proximal portion 206 of the device and connects the deployable needle (described below) with the advancing mechanism 212. The connecting member can be formed from any of a variety of materials and, in some embodiments, can be omitted in place of a needle body that extends from the distal tip of the catheter 201 to the proximal portion 206 of the device. In some embodiments, the connecting member 408 can be formed from a polyimide tube and can include an inner lumen that can communicate with the therapy fluid line 214 and an inner lumen of the deployable needle (described below).

Figure 5A:
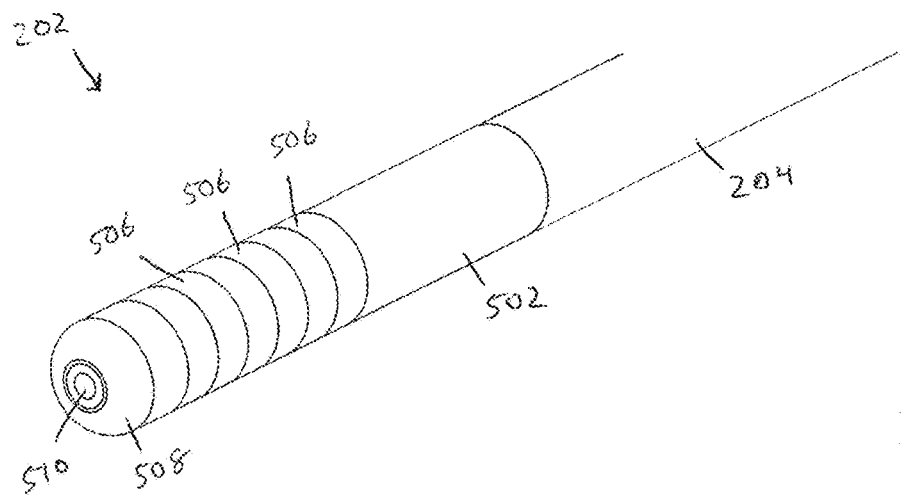
FIG. 5A is a perspective view of a distal end of the catheter device of FIG. 2 in a retracted configuration.
Figure 5B:
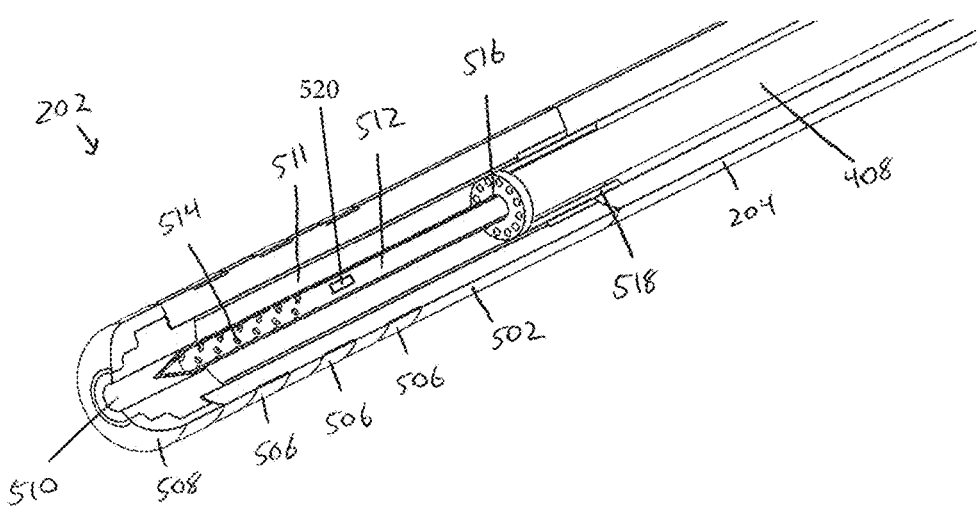
FIG. 5B is a cutaway view of the catheter distal end of FIG. 5A.
Figure 5C:
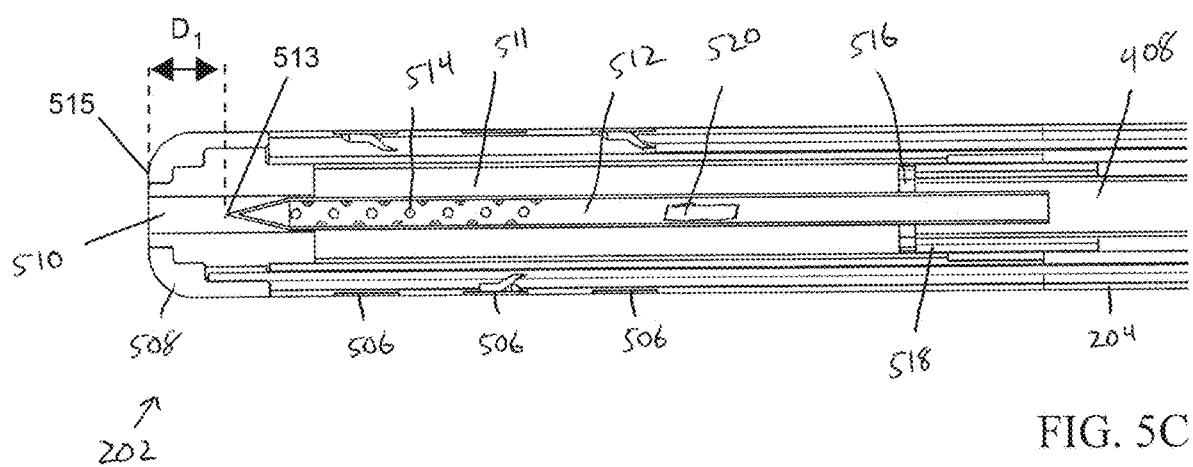
FIG. 5C is a cross sectional view of the catheter distal end of FIG. 5A.

FIGS. 5A-5C illustrate the distal portion 202 of the device 200 in a fully retracted (i.e., not deployed) configuration. The distal portion 202 of the device includes an end portion 502 that is coupled to the flexible portion 204 extending to the proximal portion 206 of the device. The end portion 502 is positioned distal to any steering components of the device 200 and therefore does not change dimensions due to tension or compression experienced during steering. The end portion 502 can have a variety of different lengths and diameters, depending on the length of any deployable instruments carried there-within. The end portion 502 can also include any of a variety of other features or devices to aid in operation of the device. For example, the illustrated end portion 502 includes mapping ring electrodes 506 disposed about an outer surface of the end portion. The ring electrodes 506 can be used to help guide the catheter into position within, e.g., a patient's heart. A distal tip 508 caps the end portion 502 and includes an opening 510 formed on a distal face of the tip that connects with an inner lumen 511 of the catheter 201.

The cutaway and cross sectional views of FIGS. 5B and 5C illustrate the position of the surgical instrument in the fully retracted configuration. In the illustrated embodiment, the surgical instrument is a needle 512 configured to penetrate into tissue and deliver fluid enhanced ablation therapy. As mentioned above, fluid enhanced ablation therapy involves the delivery of radio frequency (RF) electrical or other therapeutic energy in combination with therapeutically heated fluid, such as saline. Accordingly, the needle 512 can include one or more outlet ports 514 disposed along a distal portion thereof to allow fluid flowing through an inner lumen of the needle to be delivered into adjacent tissue. The needle 512 can be coupled to the connecting member 408 that extends through the flexible portion 204 of the catheter 201 into the proximal portion 206 of the device. The inner lumen of the needle can communicate with an inner lumen of the connecting member 408, which in turn can communicate with the therapy fluid line 214 to receive fluid from a reservoir or other external source.

The needle 512 can be formed from a variety of different materials and can have many different diameters, lengths, sidewall thicknesses, etc. In some embodiments, the needle 512 can be a 25 gauge thin-walled stainless steel needle having an inner lumen diameter of about 0.4 mm. The needle can have disposed thereon at least one ablation element configured to deliver therapeutic electrical or other energy to surrounding tissue. The ablation element can be a discrete element coupled to the needle 512 or, in some embodiments, all or part of the needle itself can be used as an ablation element. For example, the conductive needle 512 can be electrically coupled to a power source or other controlling components via, e.g., a cable extending through inlet 218, to facilitate delivery of RF energy into tissue after the needle has been deployed into, e.g., a heart wall. The needle 512 can also include a heating element 520 disposed within the inner lumen thereof to heat saline (e.g., normal or concentrated saline solutions), Ringer's solution, or any other fluid utilized in the therapy to a therapeutic level before delivering it into adjacent tissue through the one or more outlet ports 514. The heating element 520 can be, for example, one or more wires suspended within the inner lumen of the needle 512 that pass RF electrical energy through the fluid as it flows through the needle. For example, in some embodiments the heating element 520 can be a single wire suspended within the inner lumen of the needle 512 and fluid flowing through the inner lumen cab be heated by electrical energy passed between the wire and the needle body. In other embodiments, the heating element 520 can include two wires suspended within the inner lumen of the needle 512 that can pass electrical energy there between to heat fluid flowing through the inner lumen. In either such embodiment, the one or more wires can be passed through one or more spacers to prevent any inadvertent contact between the wires and the needle 512. Further information on heating assemblies for use with fluid enhanced ablation therapy can be found in U.S. Patent Publication No. 2012/0265190, entitled "Methods and Devices for Heating Fluid in Fluid Enhanced Ablation Therapy," the entire contents of which are hereby incorporated by reference as if they were reprinted here.

The needle 512 can have formed thereon one or more protrusions or other features that are configured to abut against a retraction stop formed on the inner lumen 511 of the catheter and define a proximal-most position (referred to above as a datum position) of the needle. The protrusion or other feature formed on the needle, and the retraction stop formed on the catheter inner lumen sidewall, can have any of a variety of configurations. For example, one or more ribs, shoulders, flanges, or other features can be positioned about the circumference of the needle and catheter inner lumen sidewall such that they will interfere with one another. Further, the protrusions or other features on the needle 512 and the retraction stop formed on the inner lumen 511 can be positioned such that, when the two components are in contact with one another, a distal end 513 of the needle 512 is even with, or proximal to, a distal end 515 of the catheter end portion 502 (i.e., the distal end of the catheter 201). In such a configuration, the needle 512 can be recessed within the catheter inner lumen 511. Further, in certain embodiments, the positioning of the protrusions or other features and retraction lumen can be selected such that a gap of distance Di exists between the distal end 513 of the needle and the distal end 515 of the catheter 201.

In the illustrated embodiment, the needle 512 includes a full-circumference flange 516 formed thereon that has an outer diameter that is substantially similar to the diameter of the inner lumen 511. Proximal to the flange 516 is a retraction stop 518 formed from a collar that is coupled to the inner sidewall of the catheter inner lumen 511. The flange 516 can translate within the inner lumen 511 as the needle 512 is deployed or retracted, but the retraction stop 518 does not translate relative to the end portion 502 and therefore forms a proximal stop for the needle 512. As can be seen in FIG. 5C, the proximal face of the flange 516 abuts against the distal face of the retraction stop 518 when the needle is in the fully retracted (i.e., not deployed) configuration.

Figure 6A:
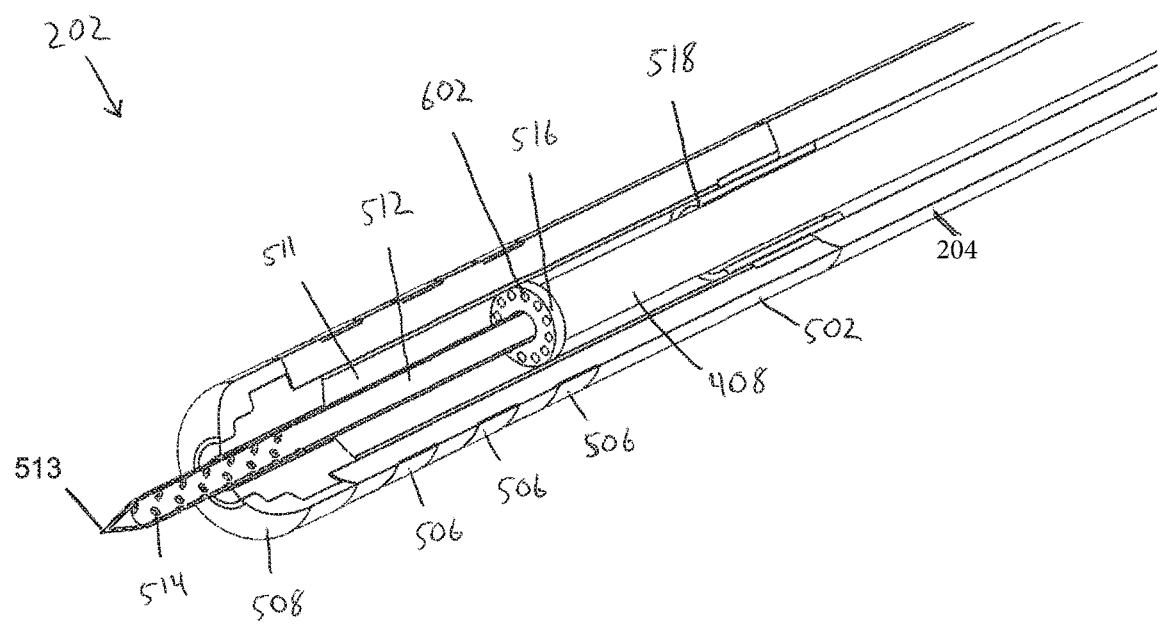
FIG. 6A is a perspective cutaway view of the distal end of the catheter device of FIG. 2 in a partially deployed configuration.
Figure 6B:
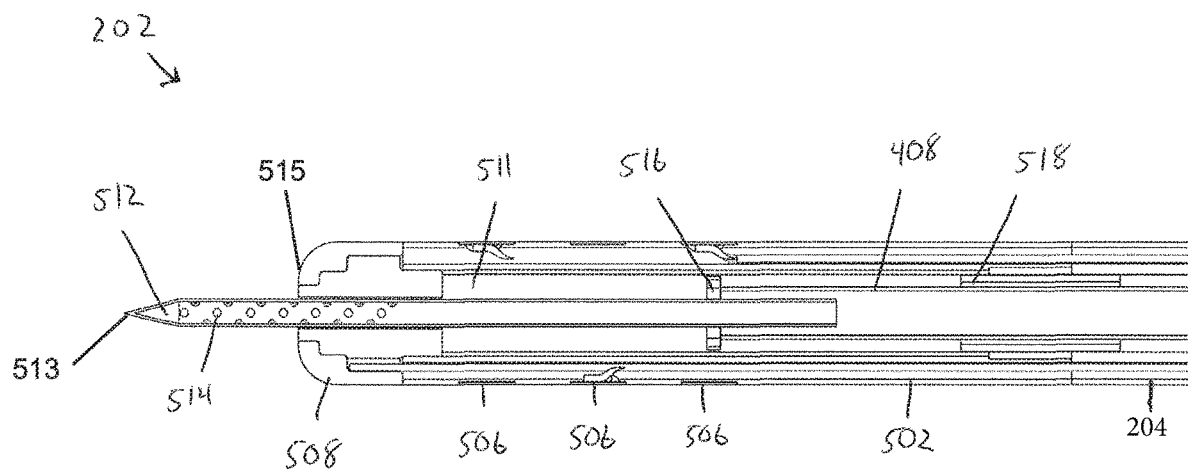
FIG. 6B is a cross sectional view of the catheter distal end of FIG. 6A.

FIGS. 6A and 6B illustrate the distal portion 202 of the device 200 when in a partially deployed configuration. In this configuration, a user has begun to advance the needle distally from the proximal portion 206 of the device using the advancing mechanism 212 (described in more detail below). Distal translation of the connecting member 408 at the proximal end of the device is transferred into distal translation of the needle 512, thereby exposing the distal tissue-puncturing tip 513 of the needle and separating the flange 516 from the retraction stop 518. In other words, the needle 512 is advanced distally such that the distal tip 513 of the needle is distal to the distal end 515 of the catheter 201.

FIG. 6A also illustrates that the collar of the retraction stop 518 surrounds the connecting member 408 with some amount of clearance to allow sliding movement of the connecting member 408 through the collar. It can also be necessary to flush the inner lumen 511 of the catheter with fluid to clear air, coagulant, or other foreign material from the device. The clearance between the retraction stop 518 inner diameter and the outer diameter of the connecting member 408 can permit such fluid flow. Because the flange 516 can be sized to extend across the diameter of the inner lumen 511, it can include one or more fluid channels 602 formed therein to allow fluid to flow through the flange 516. In the illustrated embodiment, the fluid channels include a plurality of circular passages that extend around the circumference of the flange 516. In other embodiments, the fluid passages can be formed in varying number, shape, size, etc. For example, one or more slot and/or groove-shaped passages can be formed at various positions extending around the circumference of the flange 516, etc.

The fluid channels 602 can allow fluid to be introduced from a proximal end of the device and flushed out a distal end of the device into the patient's body. Flushing the device in this manner can prevent blood from entering into the device via its distal end, thrombosing within the inner lumen, and coming back out the distal end where it could cause a stroke or other complication. Filling the inner lumen of the device with fluid also prevents any air from coming out of the device's distal end, which could cause a similar issue as a thrombus. Indeed, in some embodiments a thinning agent, such as heparin, can be included in the fluid flushed through the inner lumen to reduce the possibility of clotting further.

Figure 7A:
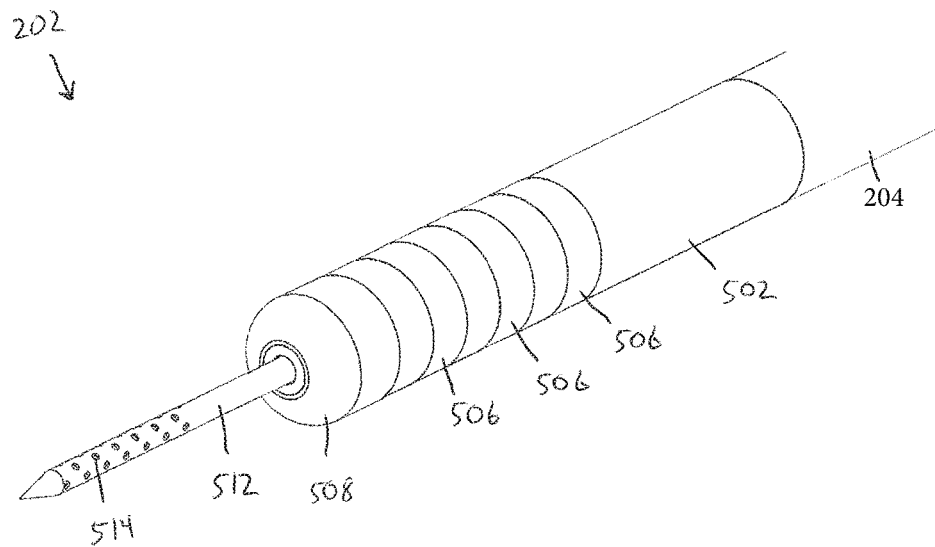
FIG. 7A is a perspective view of a distal end of the catheter device of FIG. 2 in a fully deployed configuration.
Figure 7B:
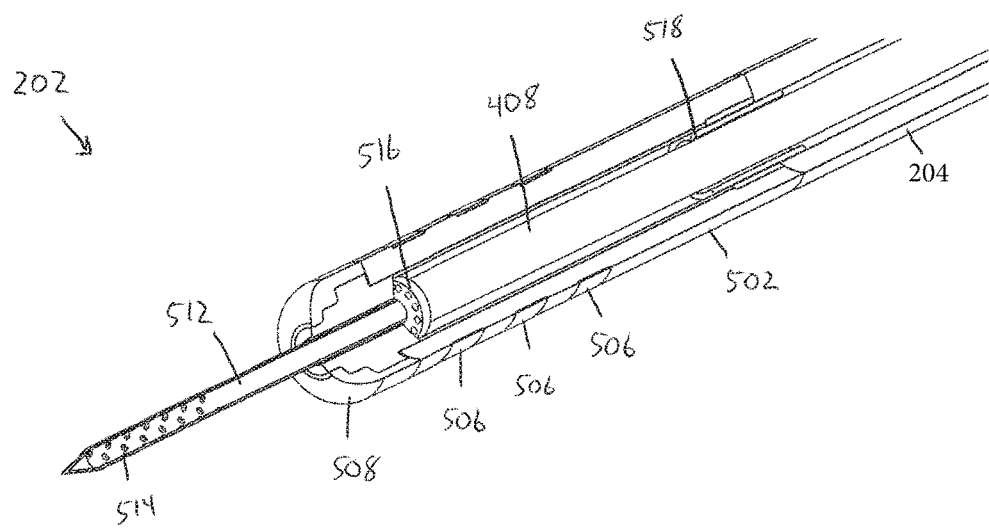
FIG. 7B is a cutaway view of the catheter distal end of FIG. 7A.
Figure 7C:
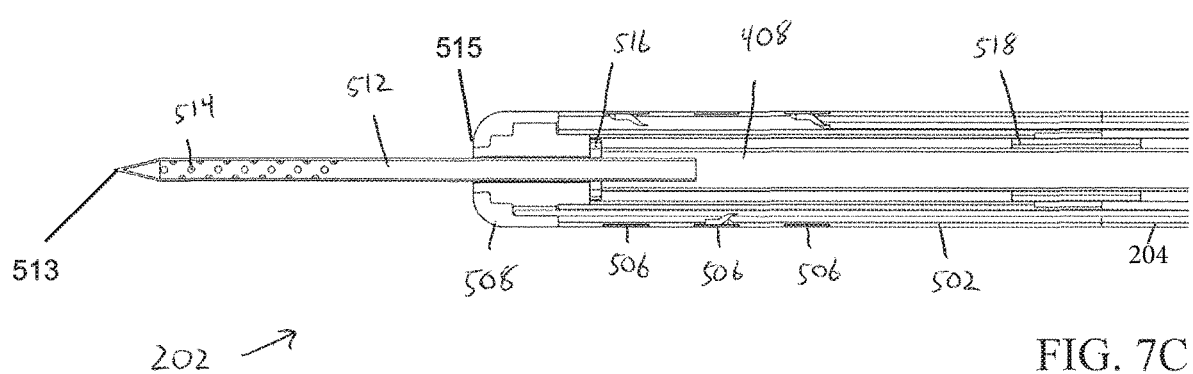
FIG. 7C is a cross sectional view of the catheter distal end of FIG. 7A.

FIGS. 7A-7C illustrate the distal portion 202 of the device 20 when in a fully deployed configuration. In such a configuration, the advancing mechanism 212 has been extended distally by a maximum amount, such that a distal face of the flange 516 abuts against a proximal face of the catheter distal tip 508. Of course, the needle 512 or other surgical instrument need not be extended to this fully deployed configuration in order to deliver therapy. Rather, the needle 512 can be deployed by whatever distance is necessary to effect the desired therapy. For example, in some embodiments the needle can have an overall length of several millimeters, but the tissue being treated can be substantially thinner than this overall length. In such an embodiment, a user can deploy the needle by only a portion of its overall length in order to ensure that the needle does not pass through the tissue entirely. By way of further example, in some embodiments, the needle 512 can have an overall length of about 13 mm and can be configured to extend from the distal end of the catheter by about 8 mm when fully extended. In other embodiments, however, a maximum extension of only about 4 mm may be desired. Or the maximum extension can be much larger, for example about 20 mm, as might be the case when treating thicker tissues. Still further, in some embodiments it can be desirable to increase the length of the needle within the catheter without increasing the maximum extension length of the needle beyond the catheter distal end, as increasing the portion of the needle within the catheter inner lumen can help reinforce the portion of the needle extending beyond the catheter distal end. Accordingly, a wide variety of needle lengths and extension lengths are possible in various embodiments.

Figure 8A:
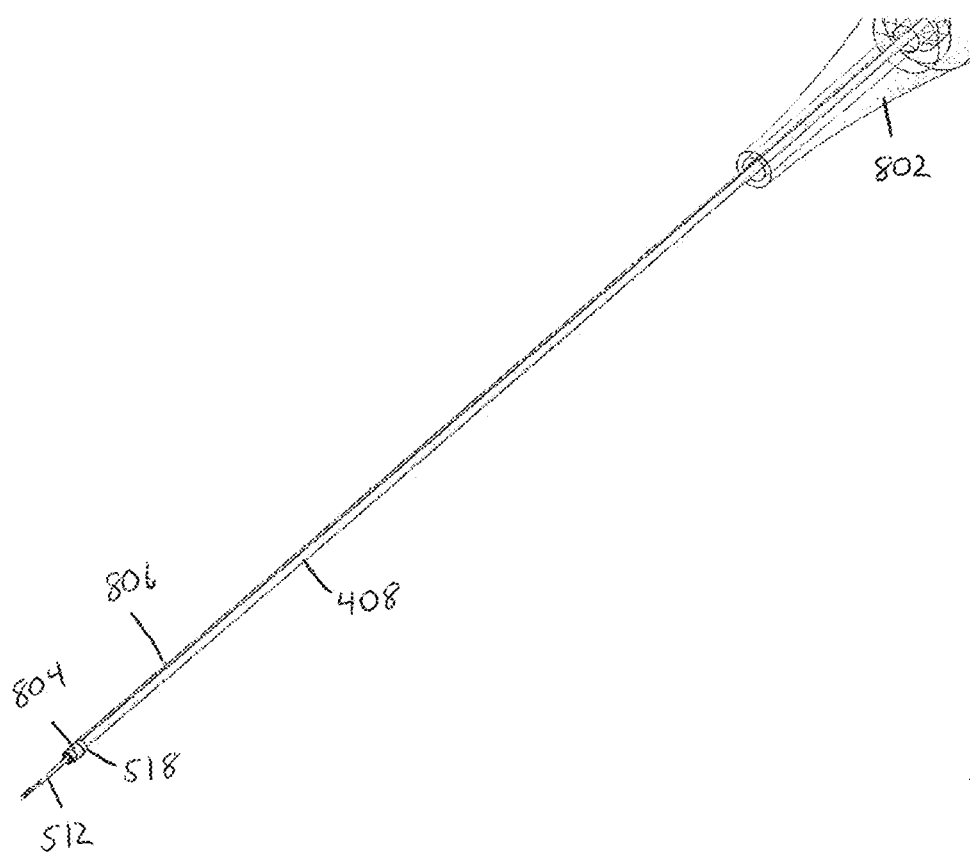
FIG. 8A is an alternative cutaway view of the distal end of the catheter device of FIG. 2 in a retracted configuration.
Figure 8B:
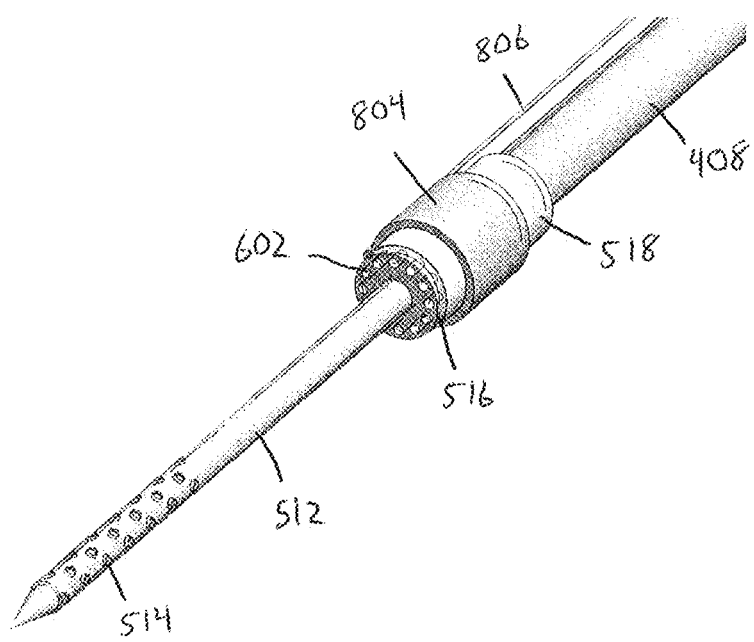
FIG. 8B is a detail cutaway view of the catheter distal end of FIG. 8A.

FIGS. 8A and 8B illustrate a cutaway view of the interaction between the needle 512, flange 516, and retraction stop 518. As shown in the figures, a proximal end of the needle 512 is coupled to a distal end of the connecting member 408, which in turn extends proximally to a distal end 802 of the proximal portion 206 of the device 200. The connecting member 408, which can be a single component or a combination of several intervening components, transfers forces applied by a user to the needle 512. The retraction stop 518, which has a fixed longitudinal position along the catheter 201, provides a proximal stop for the needle 512 and defines a datum position near the distal end of the device where the relative positions of the needle 512 and catheter 201 are known.

Also shown in the figures is a steering ring 804 and steering cable 806 that control the steering of the catheter 201. In particular, the steering ring 804 is coupled to the catheter 201 and the steering cable 806 is coupled to the steering ring 804. Pushing or pulling on the steering cable 806 from a proximal end of the device 200 (i.e., using steering controls 210) can cause the flexible portion 204 to bend and redirect the end portion 502.

The above-described bending of the flexible portion 204 can cause the length of the catheter 201 to shorten, which in prior devices can cause inadvertent exposure of the distal tip of a needle or other surgical instrument. In the illustrated embodiment, the datum position defined by the interface of the flange 516 and the retraction stop 518 is positioned distally of the steering ring 804 and the termination point of the steering cable 806. Accordingly, all deflection or flexing occurs proximal to the datum position. So long as the flange 516 remains pressed against the retraction stop 518, the relative position of the needle 512 and the end portion 502 of the catheter 201 will be known.

To maintain this positioning regardless of the contortions of the flexible portion 204, the needle 512 can be proximally biased. The biasing force can ensure that the flange 516 remains pressed against the retraction stop 518 at all times that distal advancement of the needle is undesirable. As is described in more detail below, the advancing mechanism 212 can be used to selectively overcome the biasing force and advance the needle distally once the catheter has been navigated to a surgical site.

Figure 9:
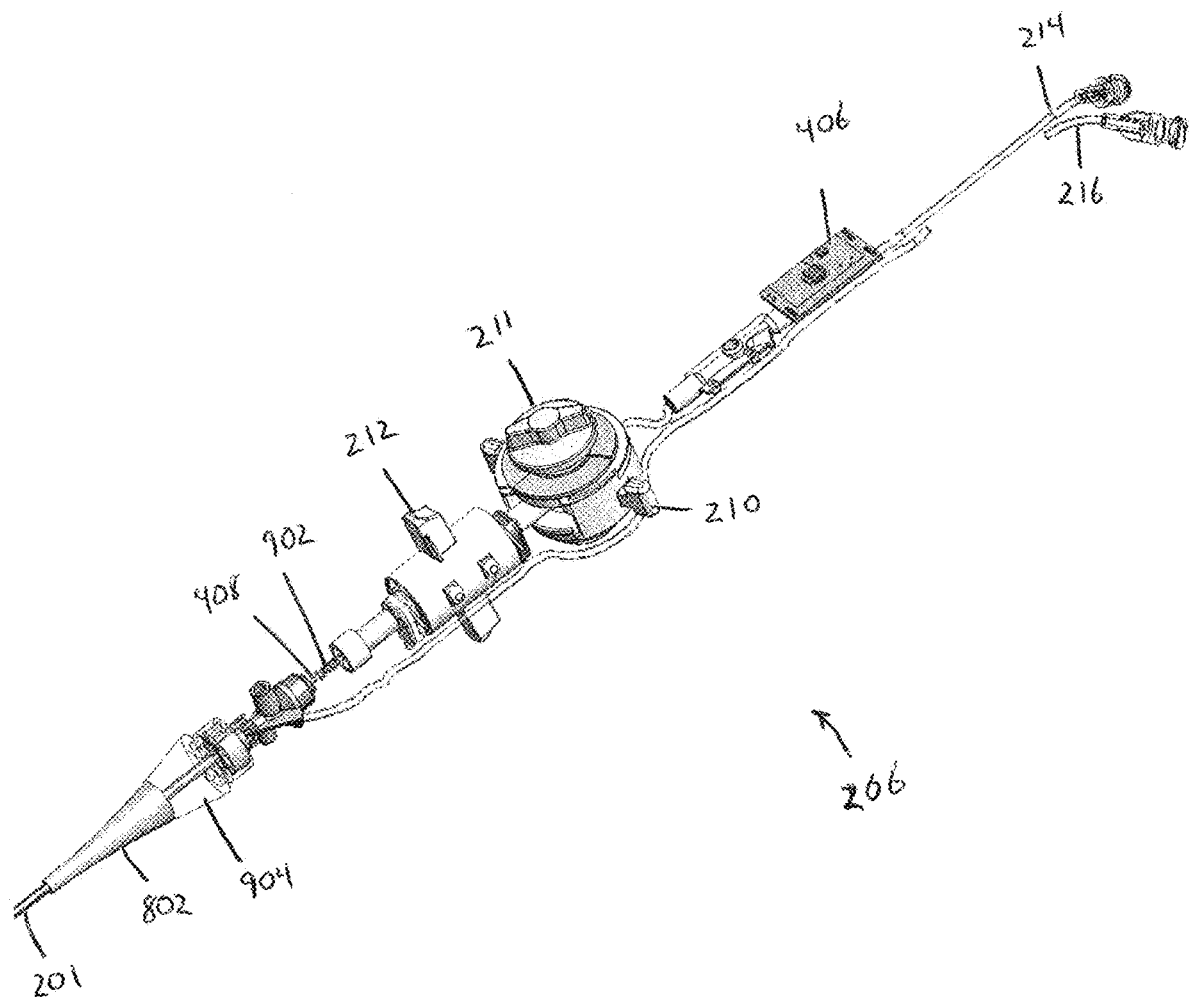
FIG. 9 is a partial view of a proximal end of the catheter device of FIG. 2.

FIG. 9 illustrates a partial view of the proximal portion 206 of the device 200. A biasing element 902 can be seen in this view distal to the advancing mechanism 212. The biasing element 902 can have a variety of different forms, but in some embodiments can be a coil or other compression spring that is compressed between a portion of the connecting member 408 and a reference structure, such as the lower housing 402 or upper housing 404. As is explained in more detail below, the biasing element 902 in the illustrated embodiment is a coil spring that is compressed between a flange 1006 (shown in FIG. 10A) rigidly coupled to the connecting member 408 and a stop 1102 (shown in FIG. 11) formed on the lower housing 402. In such an embodiment, the spring can urge the connecting member 408 proximally relative to the lower housing 402 and the advancing mechanism 212 can be configured to grasp the connecting member 408 and urge it distally, thereby further compressing the spring. In other embodiments, however, a different biasing element can be employed, including, for example, a tension spring, an electromagnetic biasing assembly, etc. Further, in certain embodiments the positioning of the biasing element can be changed, e.g., a compression spring or other biasing element could be positioned at a distal end of the device between the flange 516 on the needle 512 and the distal tip 508 of the catheter 201. Alternatively, a tension spring or other biasing element could be positioned at a proximal end of the device, similar to the configuration illustrated in FIG. 1 and described above.

Also visible in FIG. 9 is an indicator lens 904 at a distal end of the proximal portion 206. The indicator lens 904 can be formed from a transparent or translucent material and can cover one or more indicator lights 1104 (see FIG. 11) that can be utilized to provide feedback to a user. For example, in some embodiments the one or more indicator lights can be activated whenever the advancing mechanism 212 is engaged with the connecting member 408. This can serve as an indicator to a user that steering of the catheter 201 should be done cautiously, as the needle 512 or other instrument may be advanced from a distal end of the device. The one or more indicator lights 1104 can be, for example, light emitting diodes, incandescent bulbs, etc.

Figure 10:
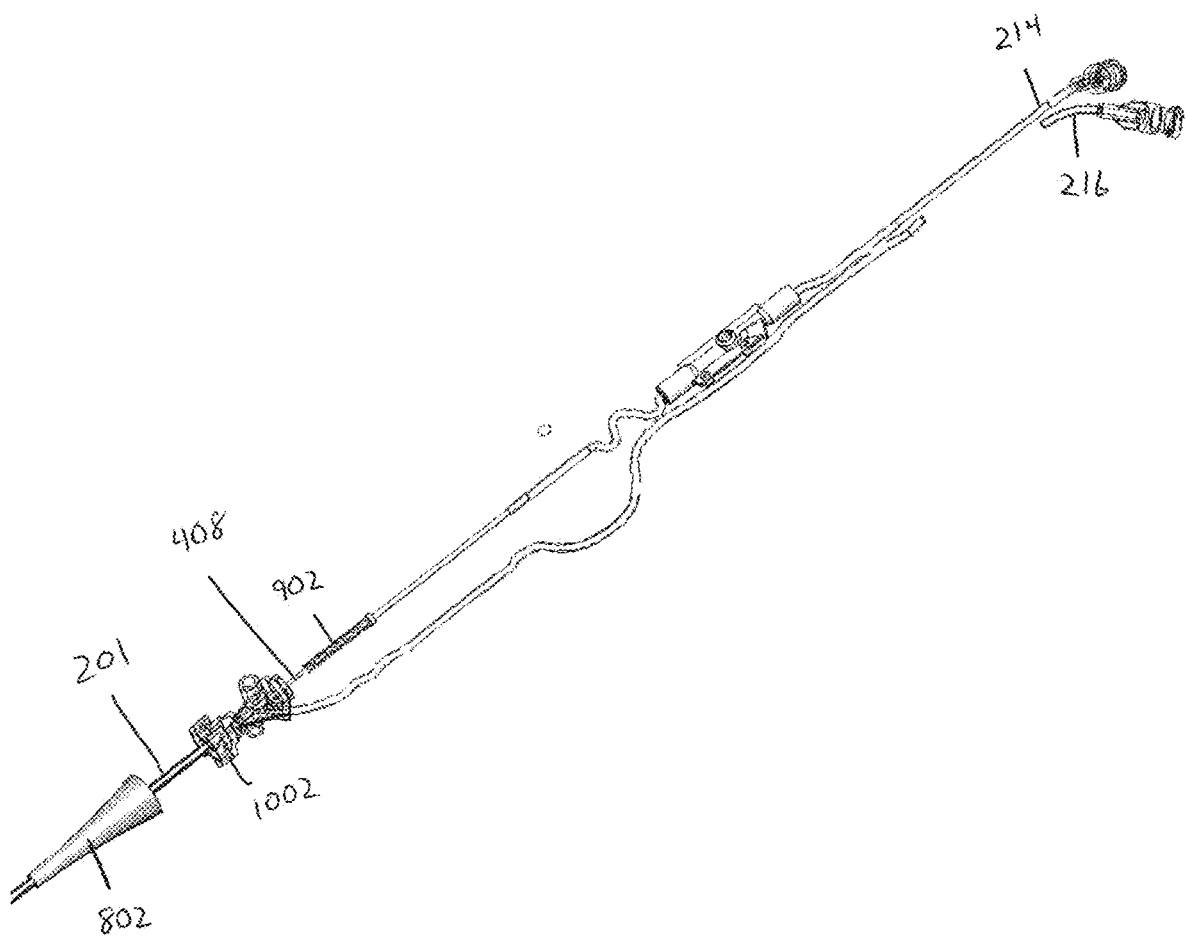
FIG. 10 is an alternative partial view of the proximal end of the catheter device of FIG. 2.

FIG. 10 shows an alternative partial view of the proximal portion 206 of the device 200. This view shows the paths of the therapy and instrument flushing fluid lines 214, 216 with greater clarity, as well as the biasing element 902. Also visible is a branch base 1002 that directs fluid flow from the instrument flushing line 216 into the annular space surrounding the connecting member 408 within the catheter inner lumen 511. The branch base 1002 can also serve as a mounting location for the one or more indicator lights 1104 (see FIG. 11).

Figure 10A:
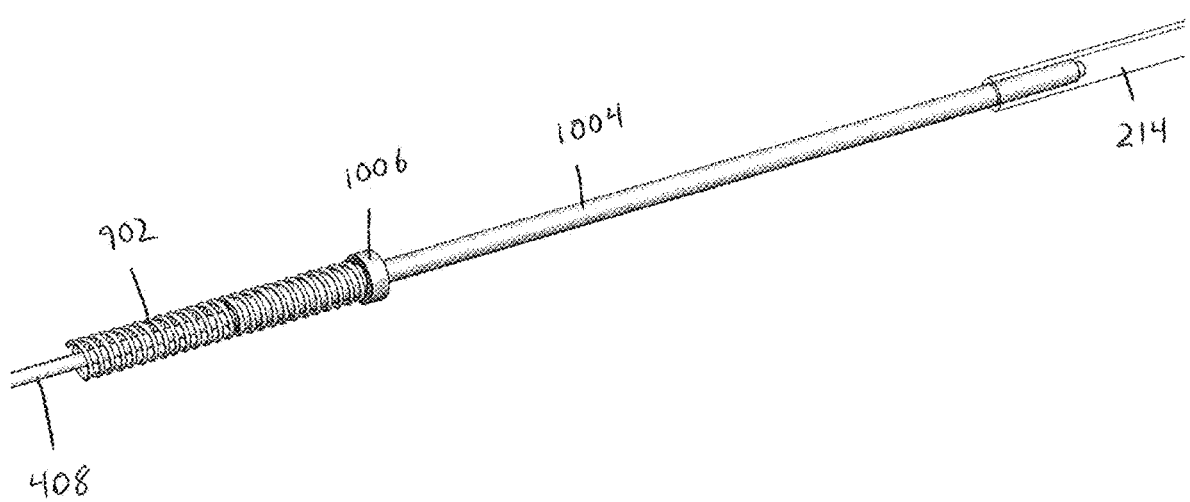
FIG. 10A is a detail view of the catheter proximal end of FIG. 10.

FIG. 10A illustrates the biasing element 902 and proximal portion of the connecting member 408 in greater detail. As can be seen in the figure, the connecting member 408 includes a sleeve 1004 coupled thereto at its distal end. The sleeve 1004 can be formed from a variety of materials but, in some embodiments, can be formed from a rigid conductive material such as stainless steel or another metal. The sleeve 1004 can be coupled to the connecting member 408 such that it cannot move relative thereto, e.g., using an epoxy or other bonding agent. The sleeve 1004 can provide greater rigidity for the advancing mechanism 212 to grip the connecting member 408 (which in some embodiments can be formed from a material that might deform when clamped by, e.g., the clutch mechanism 1301 described below). The conductive property of the material can also aid in constructing an electrical circuit to activate the one or more indicator lights 1104 (see FIG. 11), as described in more detail below.

Figure 11:
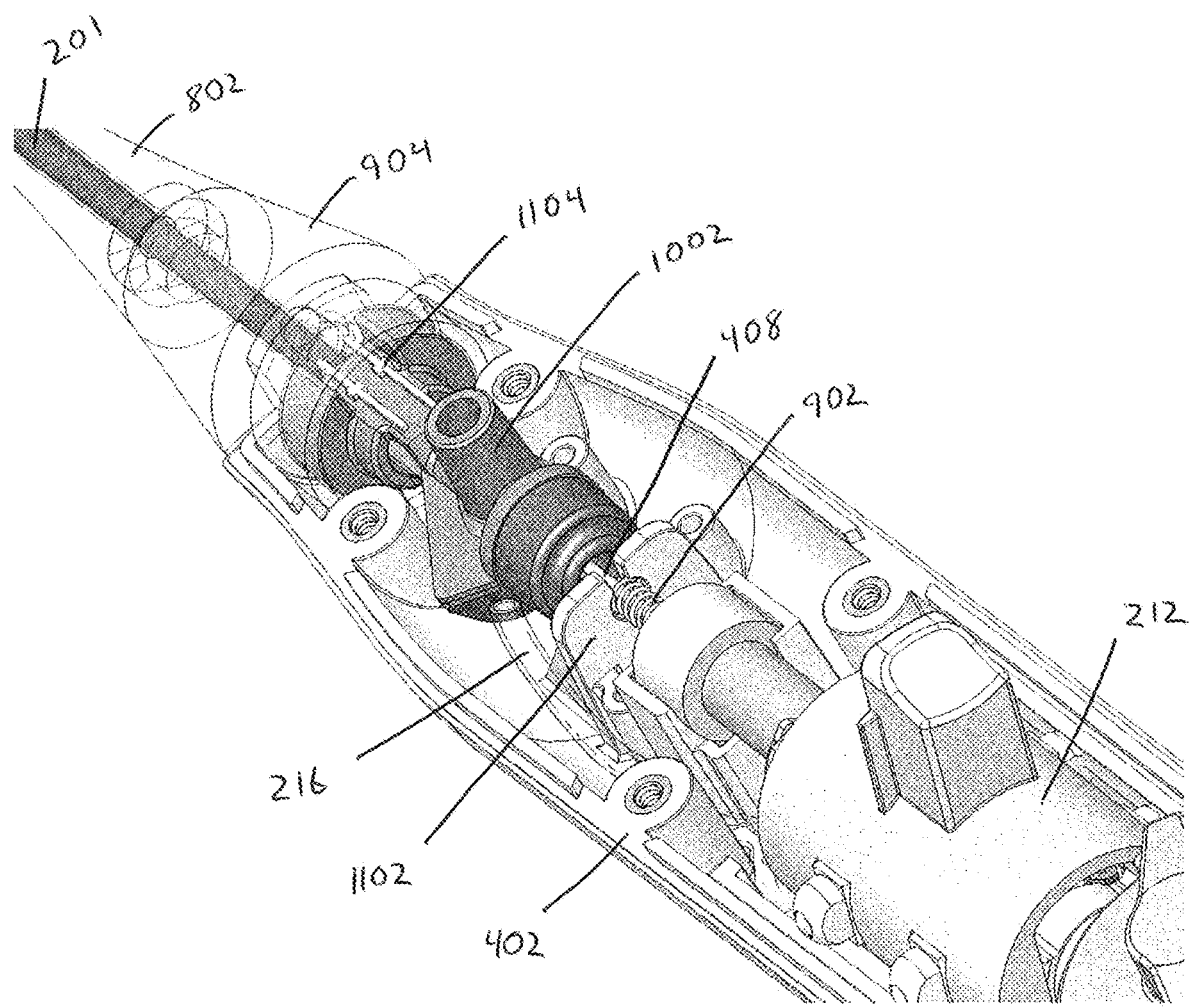
FIG. 11 is another alternative view of a proximal portion of the catheter device of FIG. 2.
Figure 12:
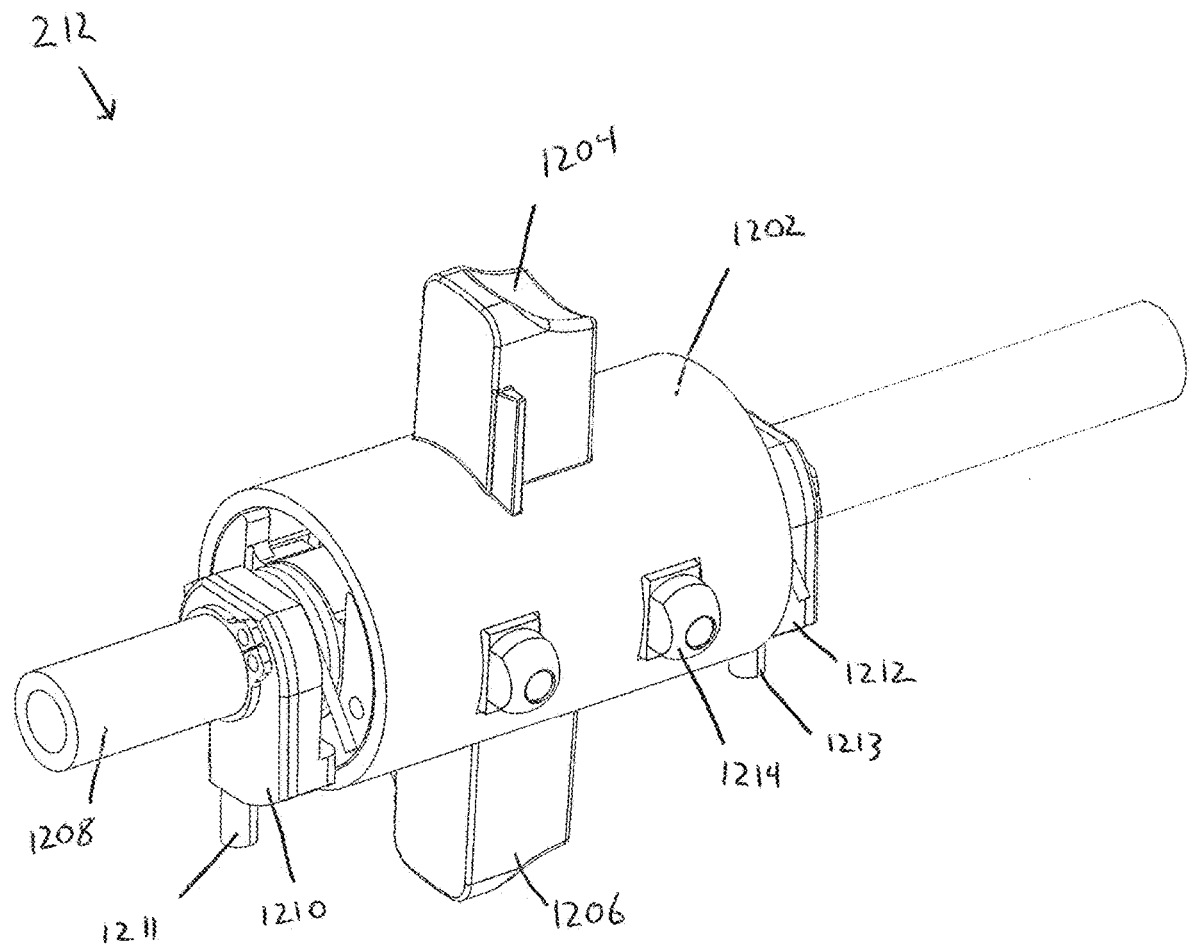
FIG. 12 is a perspective view of one embodiment of an advancing mechanism.

The sleeve 1004 can include a flange 1006 or other feature configured to abut against a proximal end of the biasing element 902. The flange 1006 can provide a surface for the biasing element 902 to act against in biasing the connecting member 408 proximally. As shown in FIG. 11, the distal end of the biasing element 902 can abut against a spring stop 1102 formed on the lower housing 402 of the device 200. As a result, the connecting member 408 can be biased proximally relative to the device housing 402, 404 and catheter 201.

FIGS. 12-19 illustrate the advancing mechanism 212 in greater detail. As mentioned above, the advancing mechanism 212 selectively engages the connecting member 408 in order to effect distal movement of the needle 512 or other surgical instrument when desired by a user. The advancing mechanism 212 can have a variety of different forms, ranging from a simple tab or other feature formed on the connecting member 408 that allows a user to exert a force on it, to a more complex assembly including a clutch mechanism that selectively couples to the connecting member 408 when actuated.

The illustrated advancing mechanism 212 includes a clutch housing 1202 having upper and lower actuating protrusions 1204, 1206 that can be manipulated by a user, as described below. A clutch cap 1208 forms a distal end of the advancing mechanism 212 that surrounds the connecting member 408. Distal and proximal anti-rotation stops 1210, 1212 are coupled to the clutch cap 1208 and clutch housing 1202, respectively, and include posts 1211, 1213 that are configured to ride within a track formed in the lower housing 402 (not shown). The track formed in the lower housing 402 extends along a longitudinal axis of the device such that the anti-rotation stops 1210, 1212 can translate proximally and distally relative to the lower housing 402, but cannot move transverse thereto. Also visible in the figure is a bearing assembly 1214 that facilitates rotational movement of the advancing mechanism 212 relative to the lower and upper housings 402, 404.

Figure 13A:
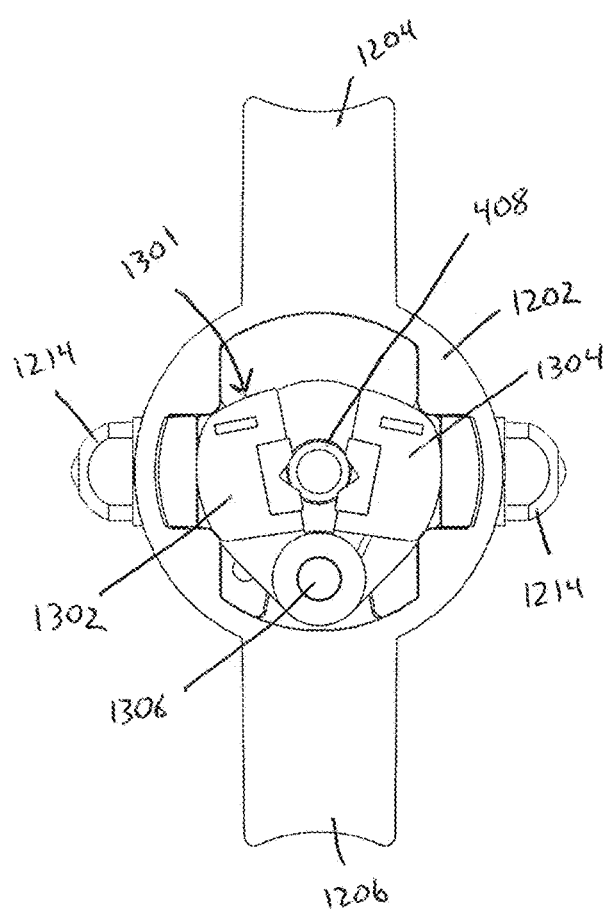
FIG. 13A is a front view of the advancing mechanism of FIG. 12 in a disengaged configuration.
Figure 13B:
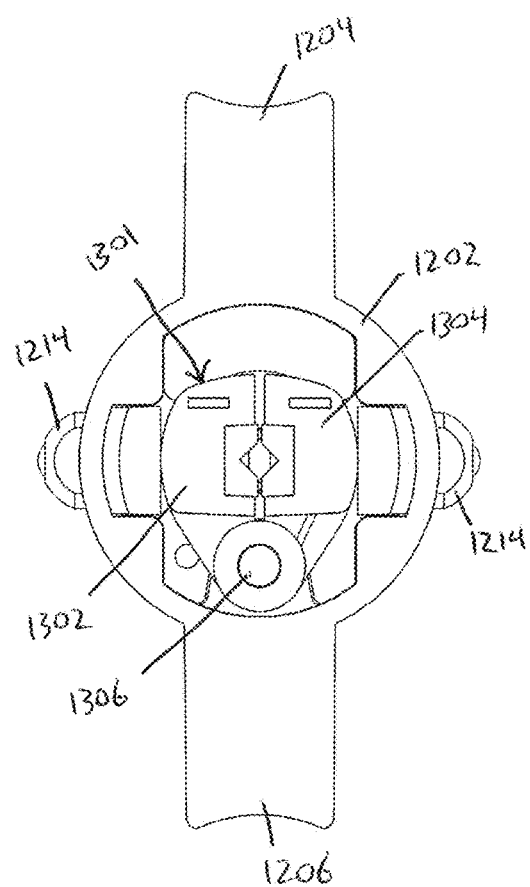
FIG. 13B is a front view of the advancing mechanism of FIG. 12 in an engaged configuration.

FIGS. 13A and 13B illustrate disengaged and engaged configurations of the advancing mechanism 212, respectively. The figures also show a clutch mechanism 1301 within the clutch housing 1202. The clutch mechanism 1301 includes a first clutch member 1302 and a second clutch member 1304 pivotally coupled to one another by a clutch shaft 1306. The first and second clutch members 1302, 1304 are biased toward an open configuration, as shown in FIG. 13A, and outer surfaces of the first and second clutch members 1302, 1304 each abut against a bearing assembly 1214. The connecting member 408 is positioned in the space between the clutch members 1302, 1304.

In the disengaged configuration of FIG. 13A, the clutch members 1302, 1304 do not contact the connecting member 408. The advancing mechanism 212 therefore does not exert any force on the connecting member 408, only the biasing element 902 acts on the connecting member. In the engaged configuration of FIG. 13B, however, the clutch members 1302, 1304 have been pivoted toward one another by a force applied by the bearing assemblies 1214. In this configuration, the clutch members 1302, 1304 contact the connecting member 408 (not shown in FIG. 13B) and pinch it to couple the advancing mechanism 212 to the connecting member 408. The advancing mechanism 212 can then be used (e.g., via force applied to the actuating protrusions 1204, 1206) to urge the connecting member 408 (and therefore the needle 512 or other instrument) distally against the force of the biasing element 902.

Figure 14A:
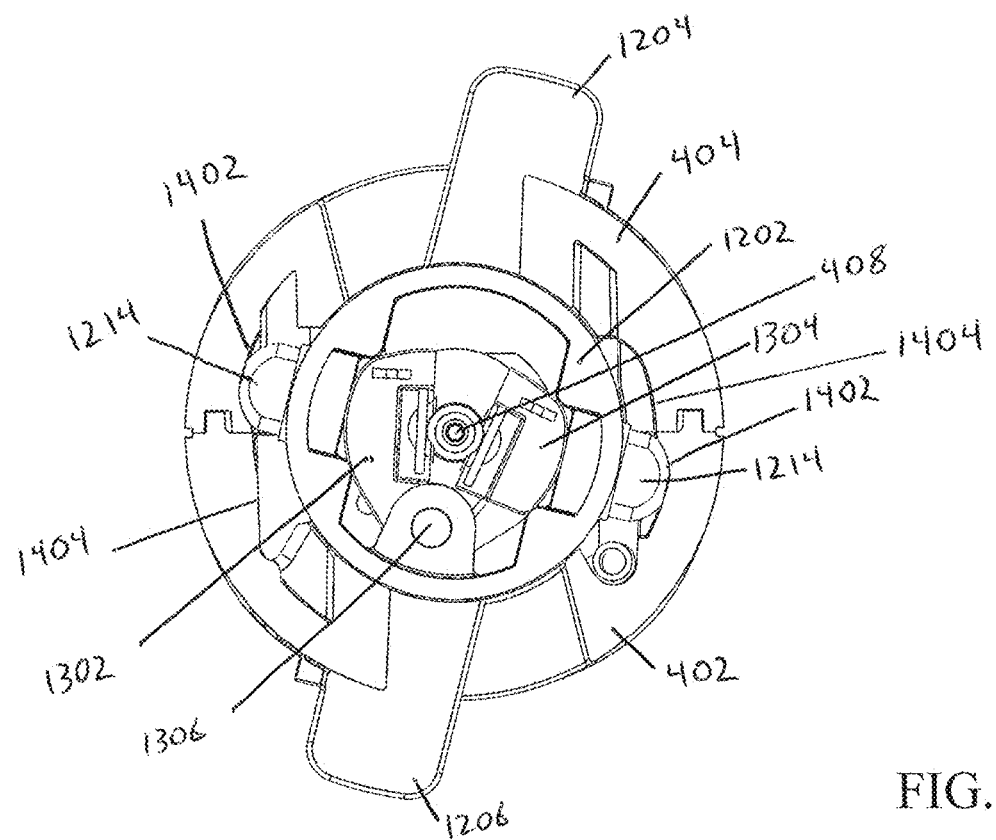
FIG. 14A is a front view of the advancing mechanism of FIG. 12 in a disengaged configuration within the device of FIG. 2.
Figure 14B:
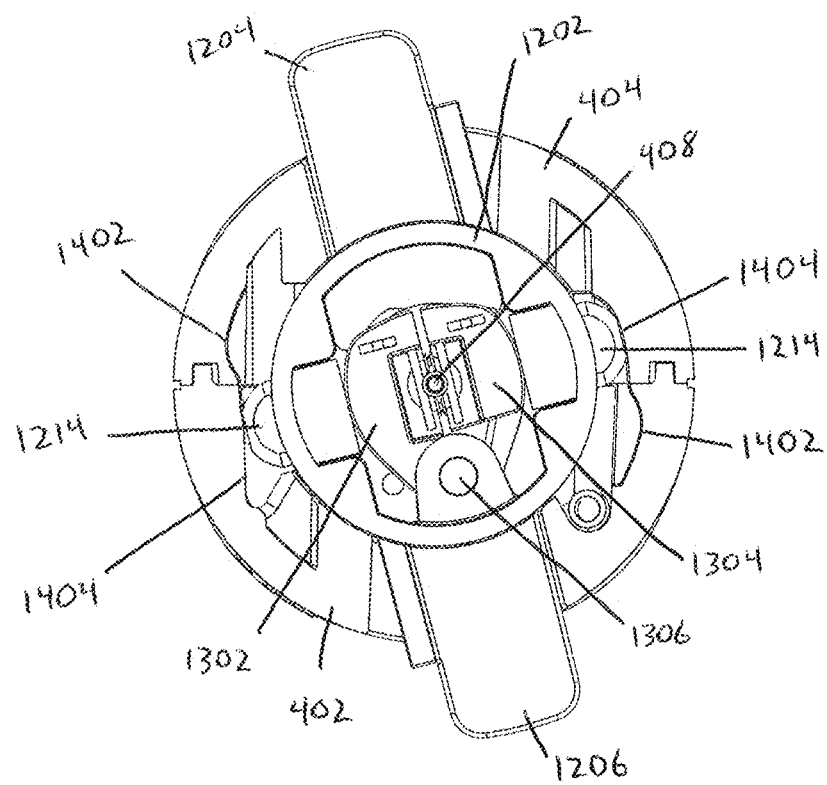
FIG. 14B is a front view of the advancing mechanism of FIG. 12 in an engaged configuration within the device of FIG. 2.

FIGS. 14A and 14B illustrate the advancing mechanism 212 in the disengaged and engaged configurations of FIGS. 13A and 13B, respectively, but also show the advancing mechanism in relation to the lower and upper housings 402, 404 of the device 200. In particular, FIGS. 14A and 14B illustrate that portions of the lower and upper housings 402, 404 are used to move the advancing mechanism 212 between the disengaged and engaged configurations as the advancing mechanism is rotated relative to the housings.

In FIG. 14A, for example, the advancing mechanism 212 is positioned within the lower and upper housings 402, 404 of the device 200 such that the bearing assemblies 1214 extending from opposite sides of the clutch housing 1202 reside within recesses 1402 formed in the lower and upper housings. The recesses 1402 allow the bearing assemblies 1214 to extend radially outward, thereby allowing the first and second clutch members 1302, 1304 to pivot away from one another about the clutch shaft 1306 (e.g., due to biasing force exerted by springs 1602 shown in FIG. 16). As mentioned above, in such a configuration the clutch members 1302, 1304 do not contact the connecting member 408 or exert any force thereon. The connecting member 408 can freely translate proximally or distally relative to the advancing mechanism 212.

To move the advancing mechanism 212 to the engaged configuration of FIG. 14B, a user can rotate the advancing mechanism by applying a force to the actuating protrusions 1204, 1206 (e.g., in the illustrated embodiment, by rotating the advancing mechanism counter-clockwise in the view of the figures). As the advancing mechanism 212 rotates counterclockwise, the bearing assemblies 1214 extending from opposite sides of the clutch housing 1202 move out of the recesses 1402 into flat portions 1404 of the lower and upper housings 402, 404. This movement presses the bearing assemblies 1214 radially inward, causing the first and second clutch members 1302, 1304 to pivot toward one another about the clutch shaft 1306. In this engaged configuration, the first and second clutch members 1302, 1304 can be coupled to the connecting member 408 such that the connecting member cannot translate relative to the advancing mechanism 212. In other words, the advancing mechanism 212 can control the proximal/distal position of the connecting member relative to the device when in the engaged configuration of FIG. 14B.

Figure 15:
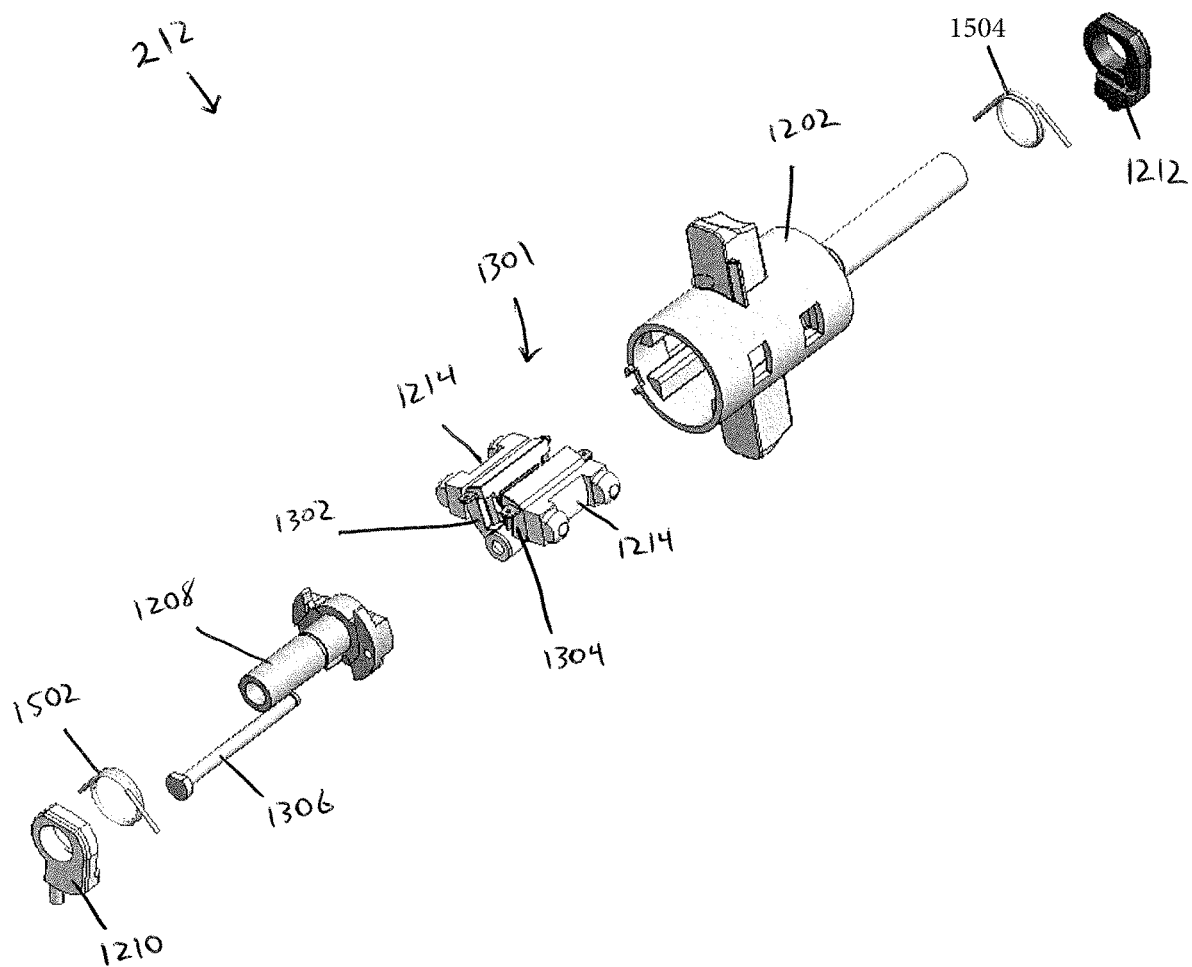
FIG. 15 is an exploded view of the advancing mechanism of FIG. 12.

FIG. 15 illustrates an exploded view of the advancing mechanism 212 to show the various components with greater clarity. In particular, the figure shows first and second biasing springs 1502, 1504 that bias the advancing mechanism toward the disengaged configuration of FIGS. 13A and 14A. The first biasing spring 1502 can be positioned between and abut against the distal anti-rotation stop 1210 and the clutch cap 1208. Similarly, the second biasing spring 1504 can be positioned between and abut against the clutch housing 1202 and the proximal anti-rotation stop 1212. The posts 1211, 1213 that extend from the anti-rotation stops 1210, 1212 and ride within a track (not shown) formed in the lower housing 402 prevent the anti-rotation stops from rotating relative to the lower housing 402 (though they can still translate longitudinally). As a result, the first and second biasing springs 1502, 1504 can provide a rotational biasing force to the advancing mechanism 212.

Figure 16:
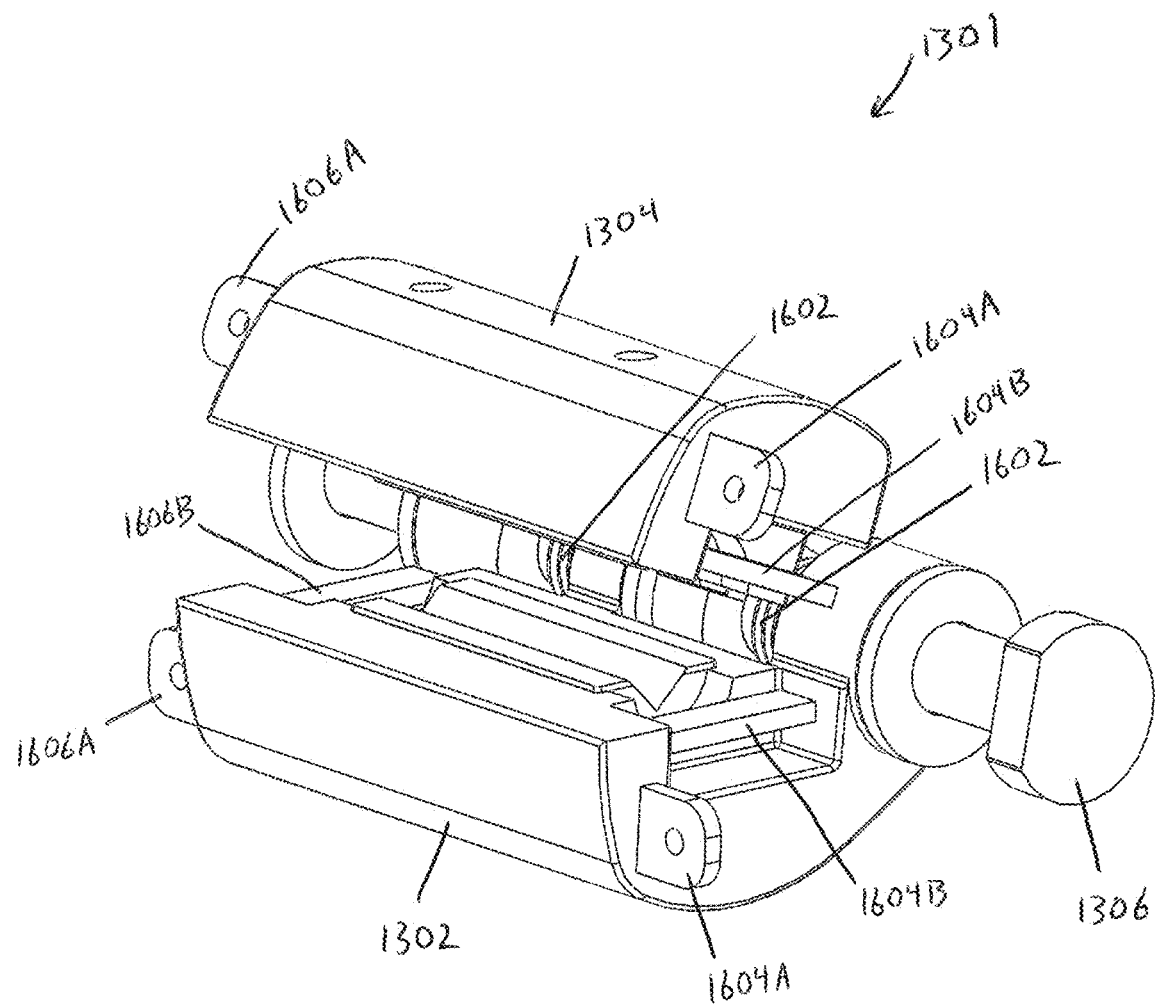
FIG. 16 is a perspective view of one embodiment of a clutch mechanism that can be utilized in an advancing mechanism.

FIG. 16 illustrates the clutch mechanism 1301 in greater detail. As noted above, the first and second clutch members 1302, 1304 are pivotally coupled to one another by the clutch shaft 1306. In addition, the first and second clutch members 1302, 1304 are biased toward an open configuration by one or more biasing springs 1602 disposed around the clutch shaft 1306. The first and second clutch members 1302, 1304 can have a variety of different shapes and sizes, depending on the size of other components in the device, how large the connecting member 408 is, etc. In addition, the first and second clutch members 1302, 1304 can be formed from a variety of materials, including, for example, stainless steel, acrylonitrile butadiene styrene (ABS) plastic or other suitable polymers, and even softer, more compliant materials, such as rubber (e.g., 65A durometer rubber), silicone or silicone blends, etc. Further, the first and second clutch members 1302, 1304 can include mechanical teeth or other features to aid in grasping a connecting member 408. For example, mechanical teeth in the form of a coil (i.e., thread-like) can be formed on each member to aid in grasping a connecting member.

The first and second clutch members 1302, 1304 are also configured to form part of an electrical circuit that activates the one or more indicator lights 1104 when the advancing mechanism 212 is in the engaged configuration. In particular, each clutch member includes a first distal electrical connector 1604A and a second distal electrical connector 1604B, as well as a first proximal electrical connector 1606A and a second proximal electrical connector 1606B. In each clutch member, the first and second distal electrical connectors 1604A, 1604B are electrically coupled to one another, and the first and second proximal electrical connectors 1606A, 1606B are electrically coupled to one another, but the sets of distal and proximal electrical connectors (i.e., 1604A, 1604B and 1606A, 1606B) are electrically isolated from one another. In addition, the second distal electrical connector 1604B and the second proximal electrical connector 1606B are configured to contact the connecting member 408 when the clutch members are in contact with the connecting member.

To create an electrical circuit that activates the one or more indicator lights 1104 only when the advancing mechanism 212 is in an engaged configuration, the one or more indicator lights 1104 can be electrically coupled to the first distal electrical connector 1604A and a power source (not shown) can be electrically coupled to the first proximal electrical connector 1606A. When the clutch members 1302, 1304 are in a disengaged configuration (i.e., not contacting the connecting member 408), the one or more indicator lights 1104 will not be connected to the power source. When the clutch members 1302, 1304 are engaged and contact the connecting member 408, however, the connecting member can contact both the second distal electrical connector 1604B and the second proximal electrical connector 1606B to complete the circuit and conduct electricity to the one or more indicator lights 1104. In order for such a circuit to operate, the connecting element 408 must be capable of conducting electricity between the two electrical connectors 1604B, 1606B, but in some embodiments non-conductive materials (e.g., polymers) are used to form the connecting member. In such embodiments, the sleeve 1004 disposed around the connecting member 408 and formed from stainless steel or another conductive material can extend along any portion of the connecting member that might contact the clutch members 1302, 1304.

The completion of an electrical circuit upon actuation of the advancing mechanism 212 can be utilized to provide feedback to a user in a number of different ways. Activating the one or more indicator lights 1104 to visually remind a user that the advancing mechanism is engaged is only one possible option. In other embodiments, the circuit could be coupled to a controller or other component of the system located within the device 200 or incorporated into an external controller, e.g., a fluid enhanced ablation therapy controller, as described in the patents and patent publications incorporated by reference above. Such a controller, or other external interface device, can provide similar feedback to a user visually, audibly, haptically, or otherwise. In addition, feedback from the electrical circuit can be utilized to control delivery of therapy (e.g., delivery of RF electrical energy from the needle 512). In the illustrated embodiment, however, the indicator lights 1104 can at least serve as a reminder to a user that the advancing mechanism is engaged and catheter steering operations should be conducted cautiously, as the needle 512 or other instrument may be extended from the distal end of the device.

Figure 17A:
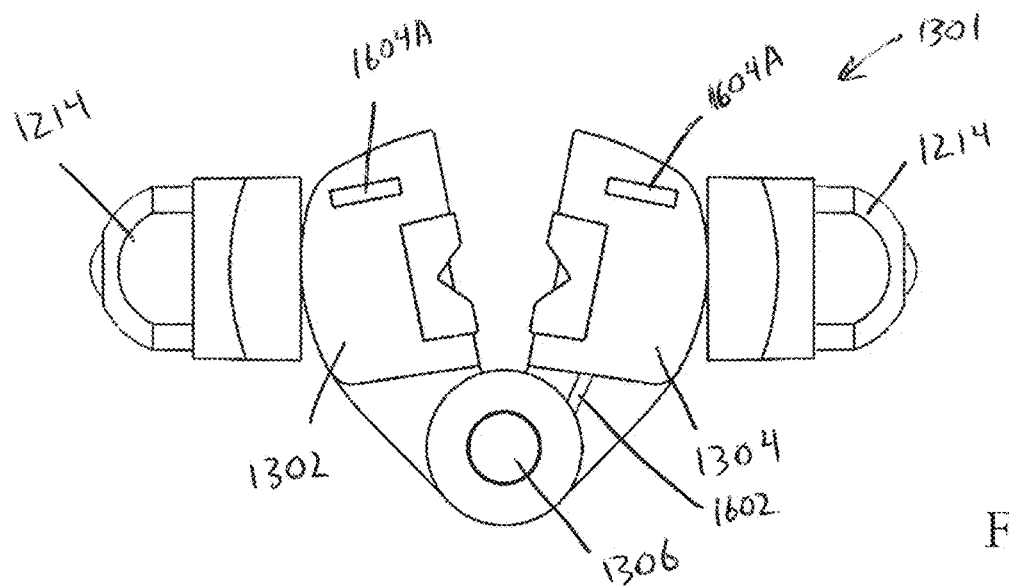
FIG. 17A is a front view of the clutch mechanism of FIG. 16 in a disengaged configuration.
Figure 17B:
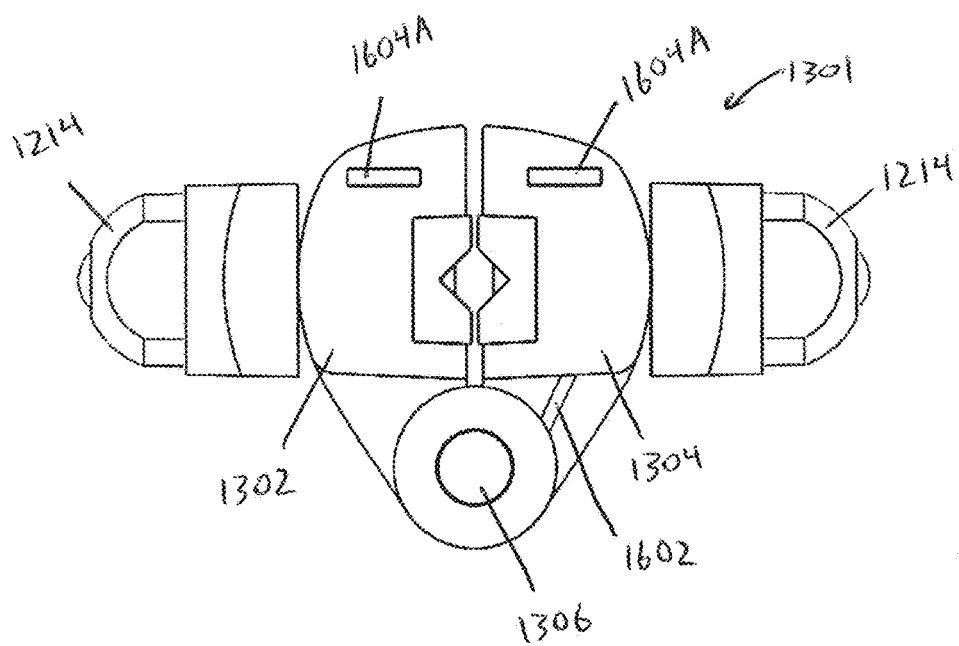
FIG. 17B is a front view of the clutch mechanism of FIG. 16 in an engaged configuration.
Figure 18:
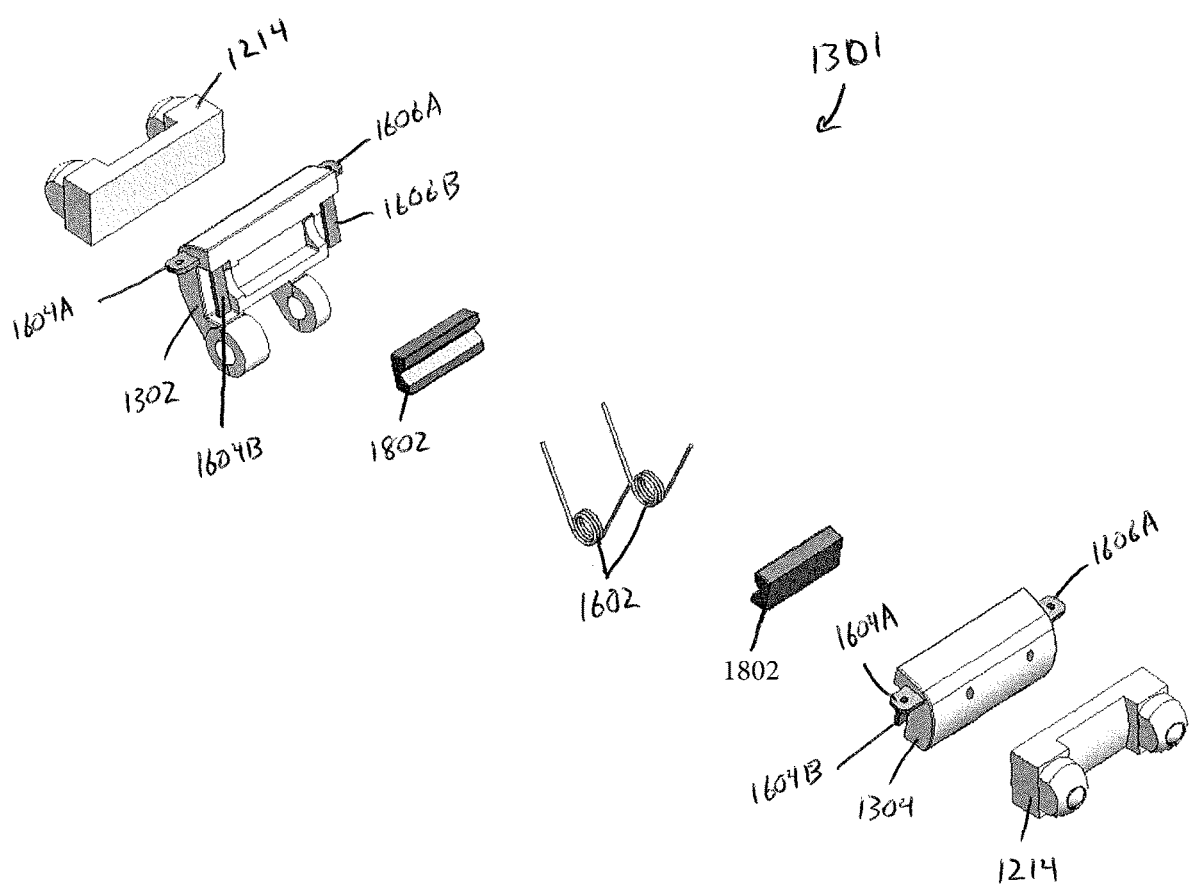
FIG. 18 is an exploded view of the clutch mechanism of FIG. 16.

FIGS. 17A and 17B illustrate the disengaged and engaged configurations of the clutch mechanism 1301 and bearing assemblies 1214 in isolation. Also shown is the first distal electrical connector 1604A of each of the clutch members, the second distal electrical connector 1604B is not shown in this view. FIG. 18 illustrates the components shown in FIGS. 17A and 17B in an exploded view. FIG. 18 shows that the clutch members 1302, 1304 can, in some embodiments, each include an insert 1802 having a shape configured to securely grasp the connecting member 408 (or sleeve 1004 disposed there-around). The inserts 1802 can be formed of the same, or a different, material than the clutch members 1302, 1304 and can have a variety of shapes and sizes. In some embodiments, for example, the inserts 1802 can be formed from stainless steel, acrylonitrile butadiene styrene (ABS) plastic or other suitable polymers, and even softer, more compliant materials, such as rubber (e.g., 65A durometer rubber), silicone or silicone blends, etc. Further, if inserts are utilized, these can include the mechanical teeth or other features mentioned above that can aid in grasping a connecting member 408. For example, mechanical teeth in the form of a coil (i.e., thread-like) can be formed on each member to aid in grasping a connecting member.

Figure 19A:
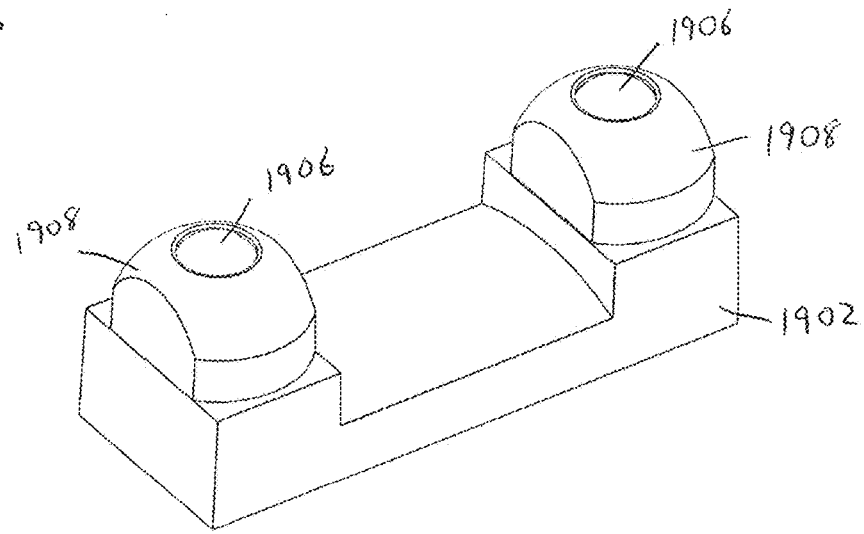
FIG. 19A is a perspective view of one embodiment of a bearing assembly.
Figure 19B:
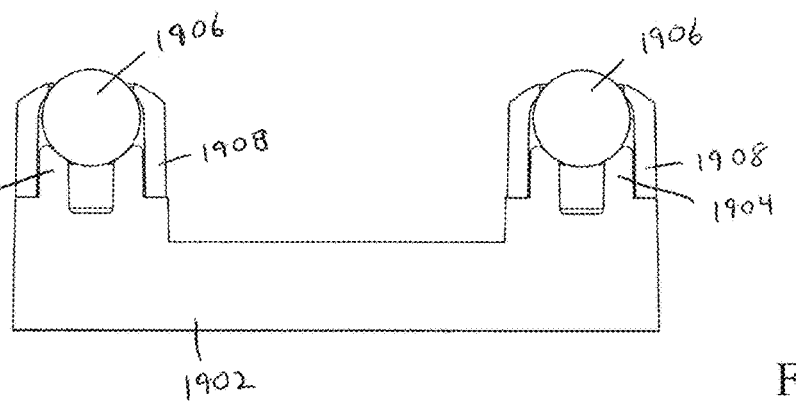
FIG. 19B is a cross sectional view of the bearing assembly of FIG. 19A.

FIGS. 19A and 19B illustrate the bearing assemblies 1214 in more detail. Each bearing assembly 1214 includes a base 1902 configured to abut against an outer surface of one of the clutch members 1302, 1304. The base also includes one or more raised portions 1904 that can seat a ball bearing 1906, as well as one or more caps 1908 that extend around each ball bearing 1906 and raised portion 1904. The caps 1908 can include an opening that allows the ball bearing 1906 to partially extend above the cap 1908. As a result, the ball bearing 1906 can abut against, e.g., the recess 1402 or flat portion 1404 of the upper or lower housing 402, 404 and can facilitate smooth movement along these portions of the housing as the advancing mechanism 212 is rotated about or translated along a longitudinal axis of the device.

FIGS. 20-22 illustrate various views of the proximal portion 206 of the device 200 as the advancing mechanism 212 is moved from the disengaged to engaged configurations described above and utilized to advance the needle 512 from the configuration shown in FIG. 5 to the configuration shown in FIG. 7. These illustrations accompany the description of a method for using the device 200 provided below.

Figure 20A:
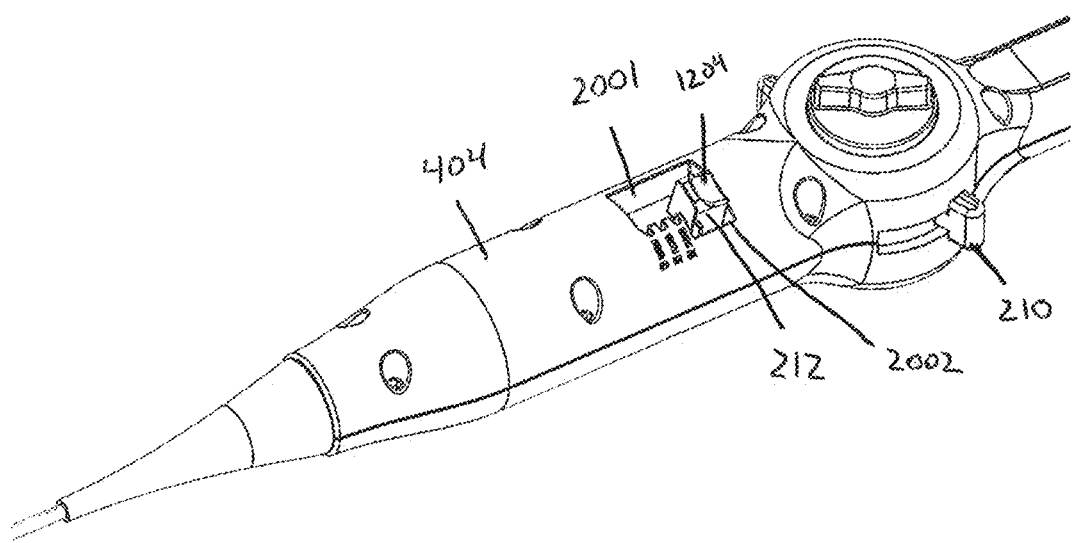
FIG. 20A is a perspective view of a proximal portion of the catheter device of FIG. 2 in a disengaged configuration.
Figure 20B:
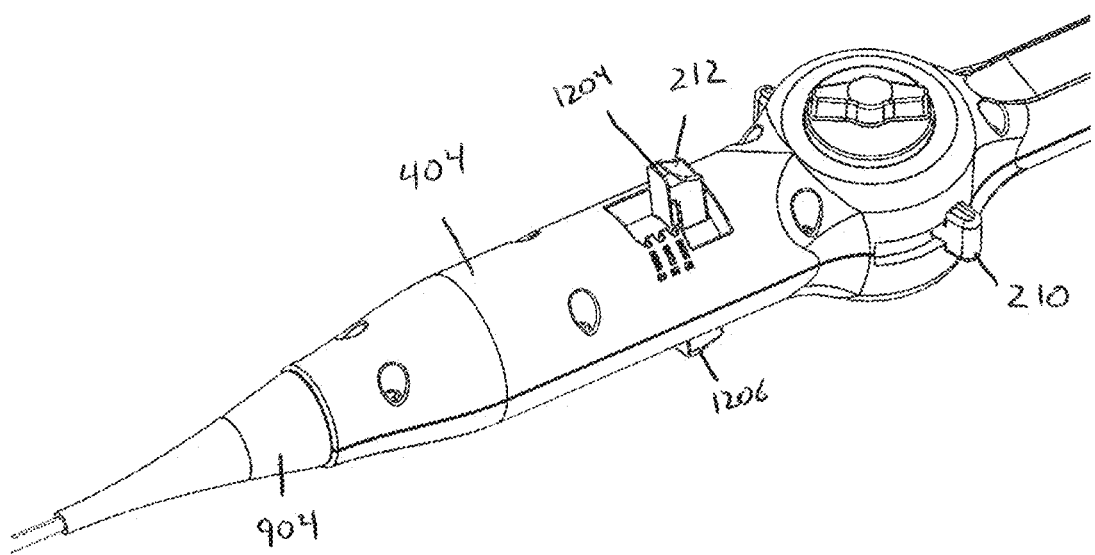
FIG. 20B is a perspective view of the catheter device of FIG. 20A in an engaged configuration.
Figure 21A:
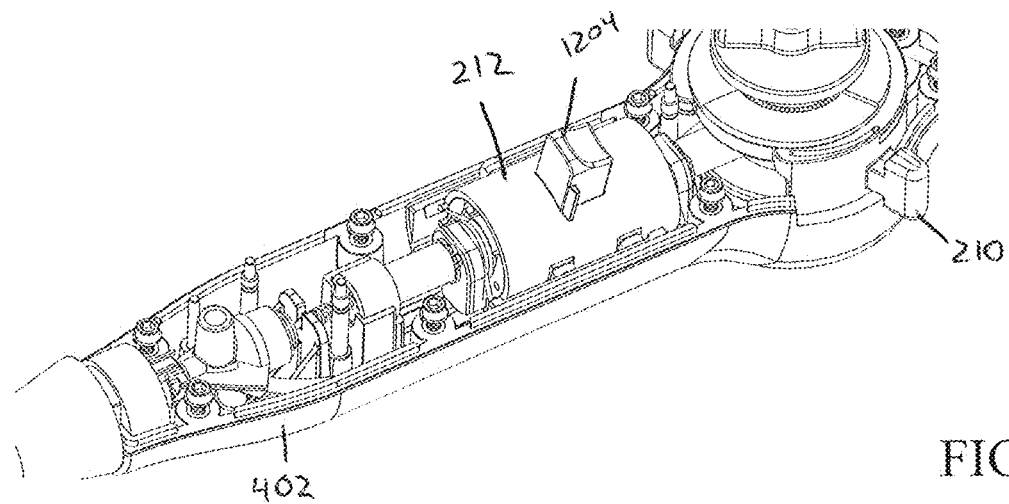
FIG. 21A is a cutaway view of the catheter device of FIG. 20A.
Figure 21B:
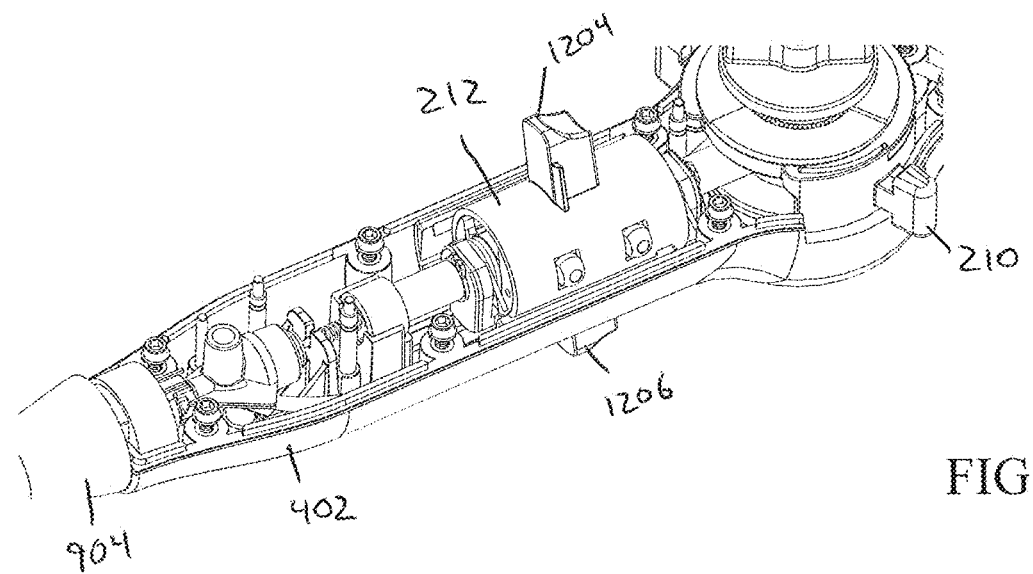
FIG. 21B is a cutaway view of the catheter device of FIG. 20B.
Figure 22A:
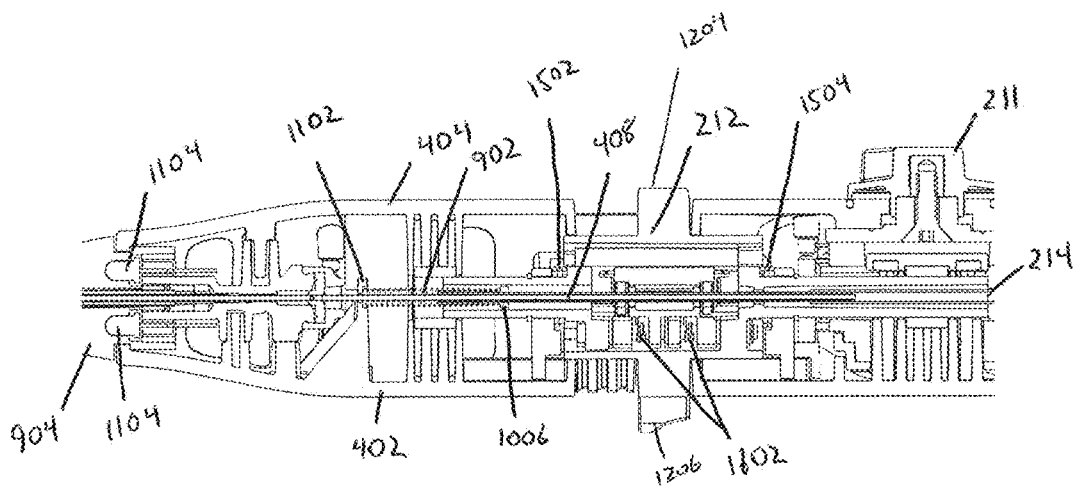
FIG. 22A is a cross sectional view of the catheter device of FIG. 20A.
Figure 22B:
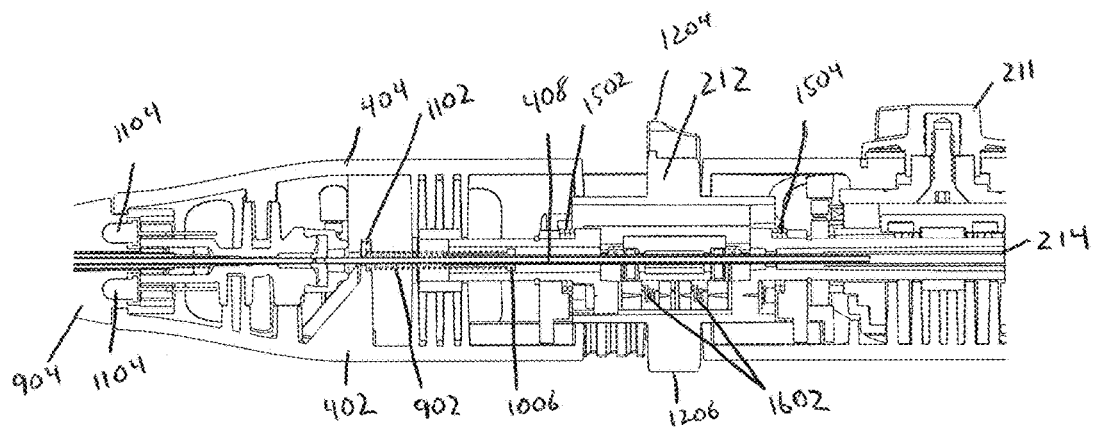
FIG. 22B is a cross sectional view of the catheter device of FIG. 20B.

At the beginning of a surgical procedure in which the device 200 is to be used, e.g., a fluid enhanced ablation therapy procedure to treat ventricular tachycardia, the advancing mechanism 212 can be positioned as shown in FIGS. 20A, 21A, and 22A. That is, the advancing mechanism 212 can be positioned at a proximal-most location such that the actuating protrusion 1204 abuts against a proximal end of an opening 2001 in the upper housing 404 (as can be appreciated from the views of FIGS. 3, 4, and 14, the actuating protrusion 1206 can similarly extend from an opening in the lower housing 402). The opening 2001 can include a notch 2002 at its proximal end that prevents the advancing mechanism 212 from translating proximally or distally relative to the device. The notch 2002 can be positioned such that the first and second biasing springs 1502, 1504 urge the advancing mechanism into the notch and into the disengaged configuration where the clutch members 1302, 1304 are not in contact with the connecting member 408.

In the configuration of FIGS. 20A, 21A, and 22A, the biasing element 902 can urge the connecting member 408 proximally until the flange 516 abuts against the retraction stop 518, as shown in FIGS. 5A-5C. As described above, the positions of the flange 516 along the needle 512 and the retraction stop 518 within the inner lumen 511 of the catheter 201 are selected such that the distal tip 513 of the needle is even with, or proximal to, the distal tip 515 of the catheter 201 when the flange abuts against the retraction stop (i.e., when at the datum position). In certain embodiments, the location of these components can be selected to maintain a desired gap Di between the distal tip 513 of the needle 512 and the distal tip 515 of the catheter 201 when in this configuration. Any desired gap distance can be utilized and, in some embodiments, it can be about 2 mm.

The catheter 201 can be steered into position within the patient's body in this configuration. In particular, the catheter can be introduced into, e.g., the patient's circulatory system, and the steering controls 210 can be utilized to steer the catheter through the patient's body to a surgical site, e.g., in the patient's heart. Due to the proximal biasing of the needle 512 and the positioning of the flange/retraction stop interface distal to the termination point of the steering cable 806, the needle remains securely within the catheter inner lumen 511. Accordingly, the user can be sure that the needle 512 will not inadvertently extend from the distal tip of the catheter, no matter how severely the flexible portion 204 of the catheter 201 bends as it is steered into position.

Once the catheter 201 has been navigated into position at a surgical site, a user can move the advancing mechanism 212 from the disengaged configuration shown in FIGS. 13A, 14A, 20A, 21A, and 22A to the engaged configuration shown in FIGS. 13B, 14B, 20B, 21B, and 22B. This is accomplished by rotating the advancing mechanism 212 to move the actuating protrusion 1204 (and, similarly, the actuating protrusion 1206 on the opposite side of the device) out of the notch 2002. The rotation of the advancing mechanism 212 causes the bearing assemblies to move from the recesses 1402 of the housing to the flat portions 1404, thereby pressing the clutch members 1302, 1304 together and securely grasping the connecting member 408. Further, the sleeve 1004 contacts the electrical connectors 1604B, 1606B on the clutch members and activates the one or more indicator lights 1104 that shine through the indicator lens 904 to inform the user that the advancing mechanism 212 has coupled to the needle 512.

Figure 20C:
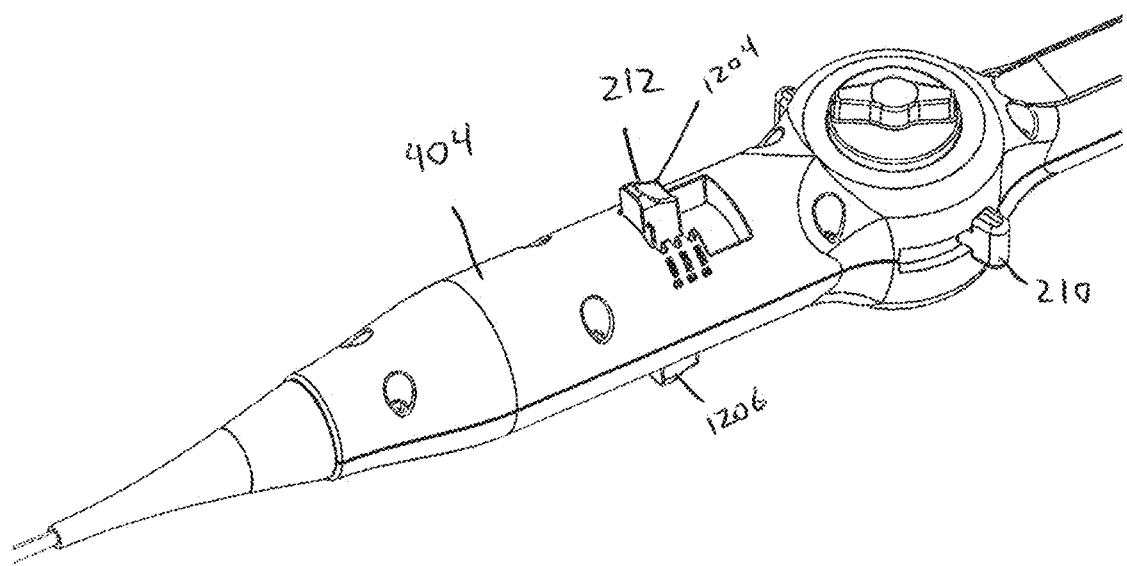
FIG. 20C is a perspective view of the catheter device of FIG. 20A in a deployed configuration.
Figure 21C:
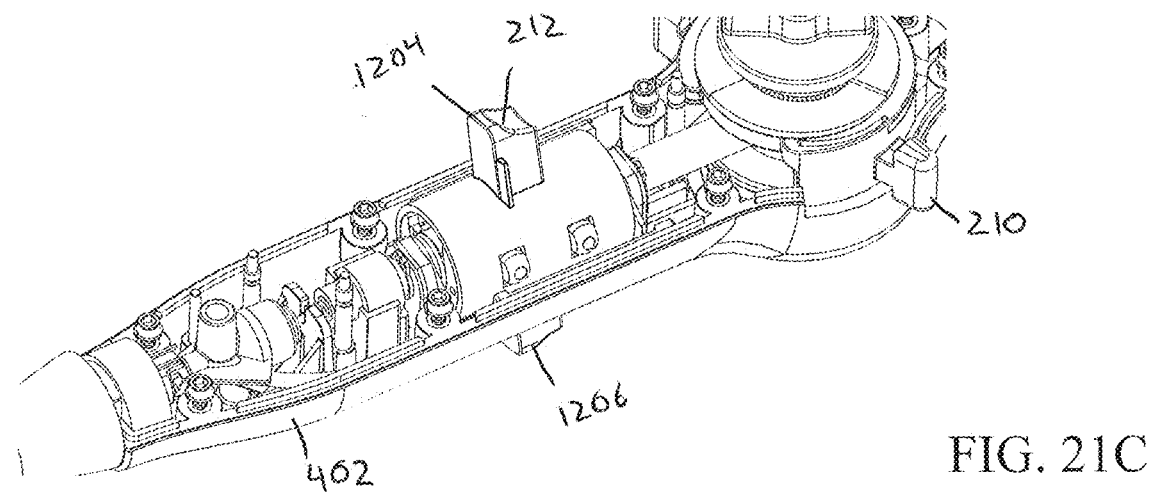
FIG. 21C is a cutaway view of the catheter device of FIG. 20C.
Figure 22C:
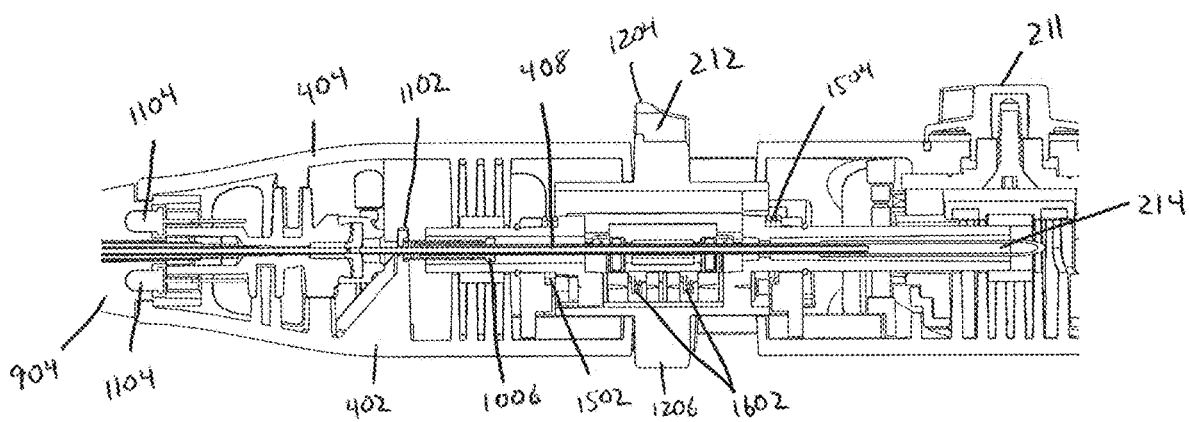
FIG. 22C is a cross sectional view of the catheter device of FIG. 20C.
Figure 23:
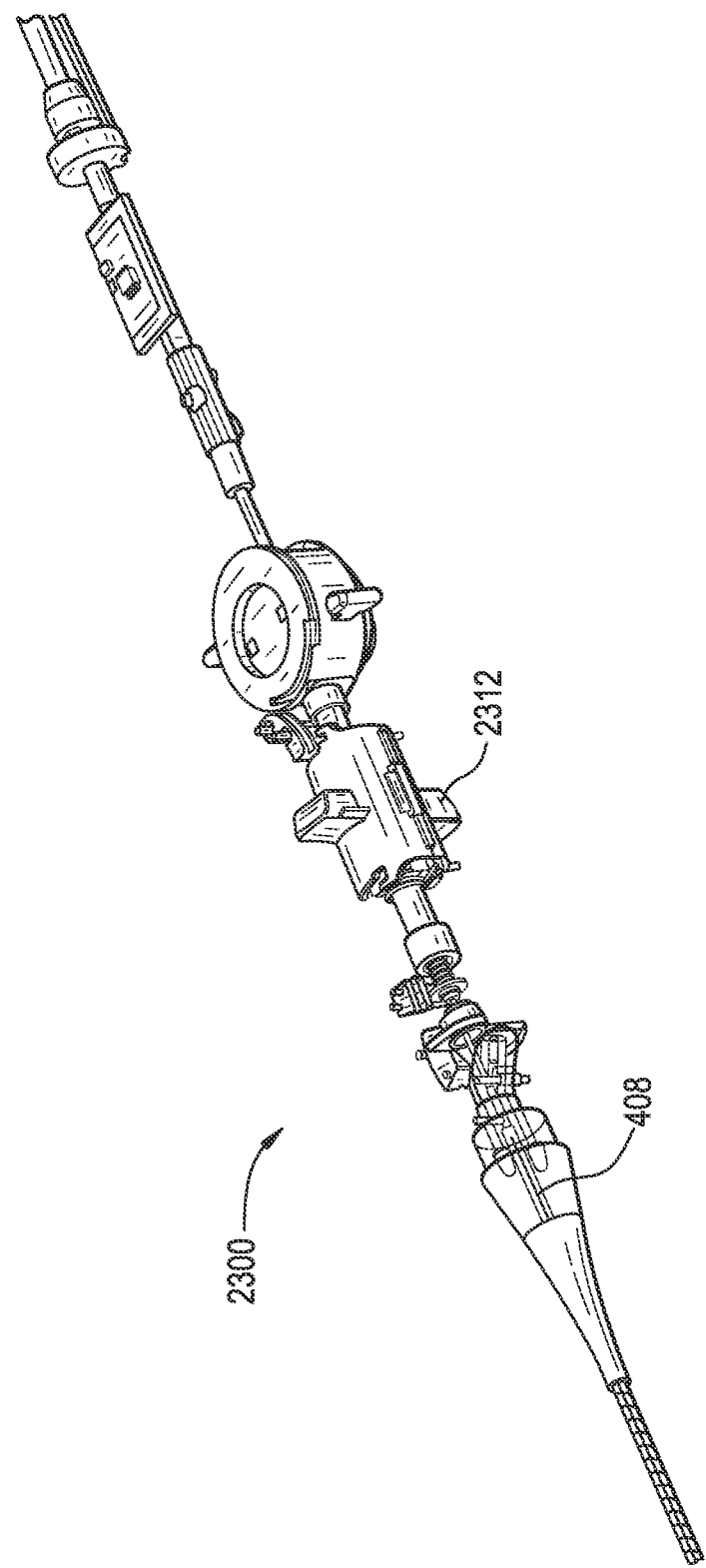
FIG. 23 is a partial view of a proximal end of another embodiment of a catheter device having a selectively deployable instrument.
Figure 24:
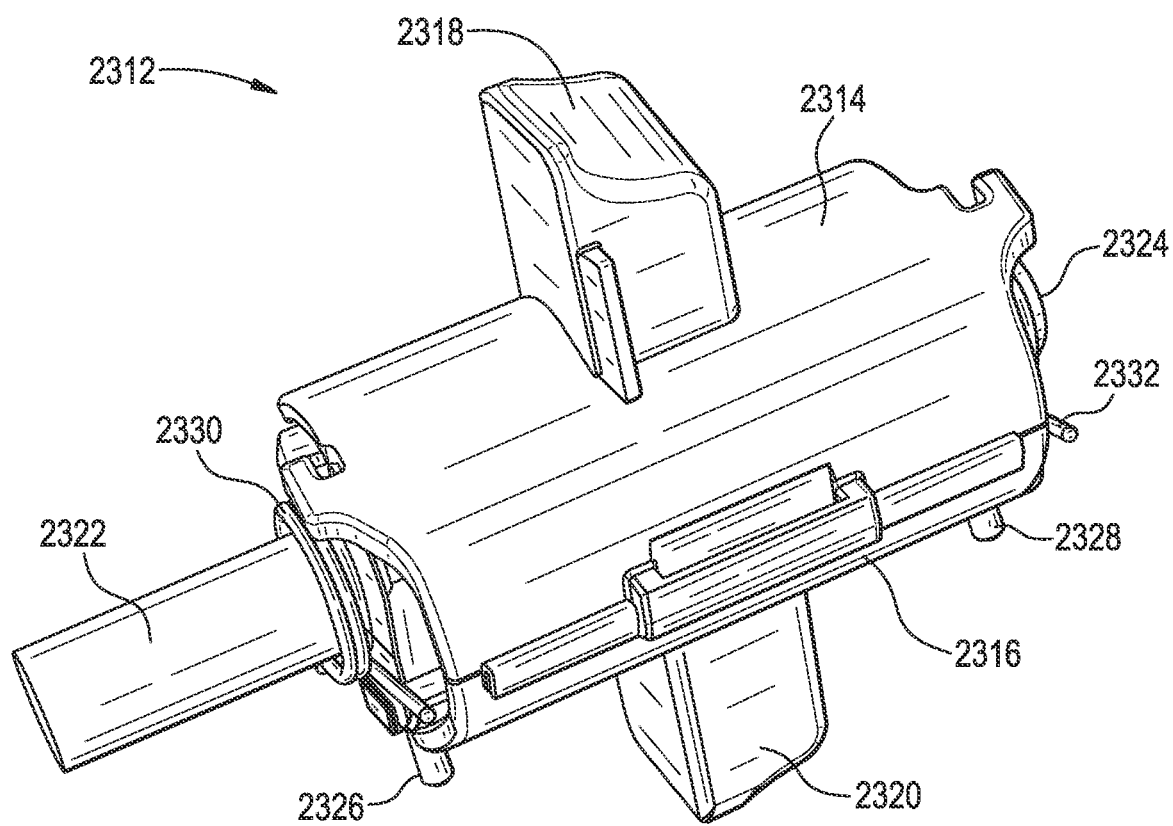
FIG. 24 is a perspective view of the advancing mechanism of the catheter device of FIG. 23.

To deploy the needle 512 from the distal tip of the catheter 201, the user can translate the advancing mechanism 212 distally as shown in FIGS. 20C, 21C, and 22C. Translating the advancing mechanism 212 in this manner similarly advances the needle 512 distally through the position shown in FIGS. 6A and 6B and ultimately into the position shown in FIGS. 7A-7C. In such a configuration, the biasing element 902 is compressed, as shown in FIG. 22C, and the advancing mechanism 212 is positioned near a distal end of the opening 2001.

Because the needle 512 always starts advancing distally from the datum position where the flange 516 is abutting against the retraction stop 518, it can be precisely controlled. The use of a biasing element can impart some compressive strain on the catheter body and some tension on the connecting member 408 that must be relieved before the needle will begin to move relative to the retraction stop 518, but this can be characterized and compensated for, e.g., when setting the position of notches 2004 described below. The end result is that distally moving the advancing mechanism 212 by, for example, 5 mm (plus whatever distance is required to compensate for the above-described biasing element strain) moves the needle 512 distally by 5 mm from the datum position. Such precision is not possible with prior devices that do not assure the beginning position of the needle or other instrument relative to the catheter distal tip.

Figure 20D:
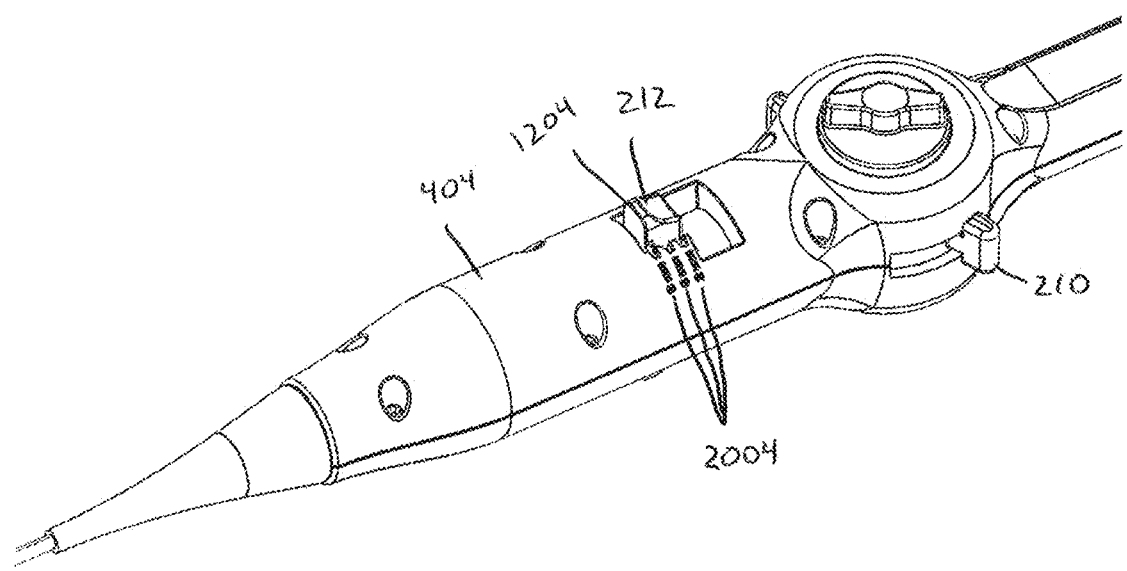
FIG. 20D is an alternative view of the catheter device of FIG. 20A in a deployed configuration.

In order to allow the user to free their hands once the needle is deployed, the opening 2001 can include one or more additional notches 2004 formed at particular deployment distances. For example, in some embodiments, notches 2004 can be provided at needle deployment distances of 2 mm, 5 mm, and 8 mm, as shown in FIG. 20D. The notches can be positioned such that the advancing mechanism 212 is urged into position within the notches by the first and second biasing springs 1502, 1504. Unlike the notch 2002, however, the notches 2004 can be positioned such that the advancing mechanism remains in the engaged configuration when seated therein, such that the connecting member 408 is securely grasped and held in place against the force of the biasing element 902. In addition, any distance represented by the notches 2004 can represent the distance that the needle 512 extends from the distal tip of the catheter 201 and can take into account any gap distance Di maintained between the needle distal tip and catheter distal tip when in the fully retracted configuration, as well as any additional advancement distance required to relieve the above-described tension in the connecting member 408 and compression in the catheter body imparted by the biasing element. Any number of notches can be provided at any variety of distances and, in some embodiments, the notches 2004 can be forgone in place of a number of other known mechanisms for maintaining the translational and rotational position of the advancing mechanism 212, such as a set screw, locking pin, etc.

Once the needle 512 is deployed from the end of the catheter 201 and inserted into tissue, a user can begin delivering fluid enhanced ablation therapy. This can include delivering fluid into the tissue from a reservoir or other source by pumping it through the therapy fluid delivery line 214 and the inner lumens of the connecting member 408 and needle 512. The fluid can be delivered into the tissue through the one or more outlet ports 514 of the needle 512. Further, the fluid can be heated prior to being delivered into surrounding tissue using a heating element 520 (see FIG. 5C) disposed within the inner lumen of the needle 512. As noted above, the heating element 520 can be, e.g., a length of exposed wire that passes RF electrical energy through the fluid and into the sidewall of the needle 512, thereby heating the fluid flowing through the inner lumen of the needle due its inherent resistivity. Further details on heating elements suitable for use with a deployable needle 512 are available in the patents and published applications incorporated by reference above.

Fluid enhanced ablation therapy can also include the delivery of RF electrical or other energy to the tissue using an ablation element disposed on an outer surface of the needle 512. In the illustrated embodiment, for example, the needle 512 can be formed from a conductive material, such as stainless steel, and its entire surface can be utilized as an electrode. In other embodiments, however, only a portion of the needle 512 can be employed as an ablation element (e.g., by covering the remainder of the needle in an insulating material) or a discrete ablation element can be coupled to the needle. Further details on ablation elements are available in the patents and published applications incorporated by reference above.

If repositioning of the catheter 201 is necessary during the operation, a user can retract the needle 512 by reversing the deployment steps detailed above. That is, the advancing mechanism 212 can be rotated out of the notch 2004, translated proximally, and rotated into a new notch, e.g., notch 2002. The needle can be moved proximally or distally by any amount desired and steering of the catheter is possible at any time. However, the indicator lights 1104 can remain activated until the clutch members 1302, 1304 of the advancing mechanism 212 separate from the connecting member 408 in order to remind the user that the needle 512 is in a deployed state. As mentioned above, in certain embodiments the signal that activates the indicator lights 1104 can be used to control other aspects of the device, including the possibility that steering controls could be locked until the needle is retracted, therapy initiation could be prevented until the needle is deployed, etc.

The foregoing description provides details of particular embodiments of the present disclosure. The particular features described with respect to these embodiments do not limit the scope of the present disclosure. For example, the device 200 described above includes a hollow needle 512 configured to deliver fluid and ablative energy to tissue. The present disclosure, however, can be applicable to any surgical instrument—needle or otherwise—that can be delivered to a surgical site in a catheter and selectively deployed for use. In addition, the particular biasing elements disclosed herein are not meant to be limiting. By way of example, the compression coil spring 902 can be positioned at various locations within the device 200, including in the distal portion 202 of the catheter 201, rather than in the proximal portion 206 of the device. Furthermore, different types of biasing elements can be employed, such as tension springs, electromagnetic biasing assemblies, etc.

Still further, the advancing mechanism 212 can have a variety of different configurations. The clutch mechanism 1301, for instance, can be replaced with a number of different possible mechanical, electromechanical, or electromagnetic clutch mechanisms. The pivoting clutch members 1302, 1304 can be replaced in some embodiments by a silicone or other compliant member that extends around the connecting member 408 and is pressed into contact with the connecting member by rotation of the advancing mechanism 212. Upon contact with the connecting member, friction can prevent movement between the compliant member and the connecting member 408 such that the advancing mechanism can be utilized to translate the needle 512 distally against the force of the biasing element 902.

FIGS. 23-28 illustrate a proximal portion of another embodiment of a catheter device 2300 that includes an alternative advancing mechanism 2312. The device 2300 is similar to the device 200 shown in FIG. 9 and the advancing mechanism 2312 functions similarly to selectively grasp the connecting member 408 and effect distal advancement of a needle or other surgical instrument. The advancing mechanism 2312, however, includes an alternative mechanical design that is shown in detail in FIGS. 24 and 25.

The advancing mechanism 2312 includes an upper clutch housing 2314 and a lower clutch housing 2316 that cooperatively enclose the other components of the mechanism. The upper and lower clutch housings 2314, 2316 each include an actuating protrusion 2318, 2320 (respectively) that can be manipulated by a user to actuate the mechanism and effect distal movement of the connecting member 408.

Distal and proximal anti-rotation stops 2322, 2324 are coupled to the upper and lower clutch housings 2314, 2316 and posts 2326, 2328 that are configured to ride within a track formed in the lower housing 402 (not shown) of the device. The track formed in the lower housing 402 can extend along a longitudinal axis of the device such that the anti-rotation stops 2322, 2324 can translate proximally and distally relative to the lower housing 402, but cannot move transverse thereto. Distal and proximal biasing springs 2330, 2332 are coupled to one of the anti-rotation stops 2322, 2324 (via posts 2329, 2331, respectively) and one of the upper and lower clutch housings 2314, 2316 to rotationally bias the clutch housings toward a disengaged configuration, similar to the advancing mechanism 212 described above.

Figure 25:
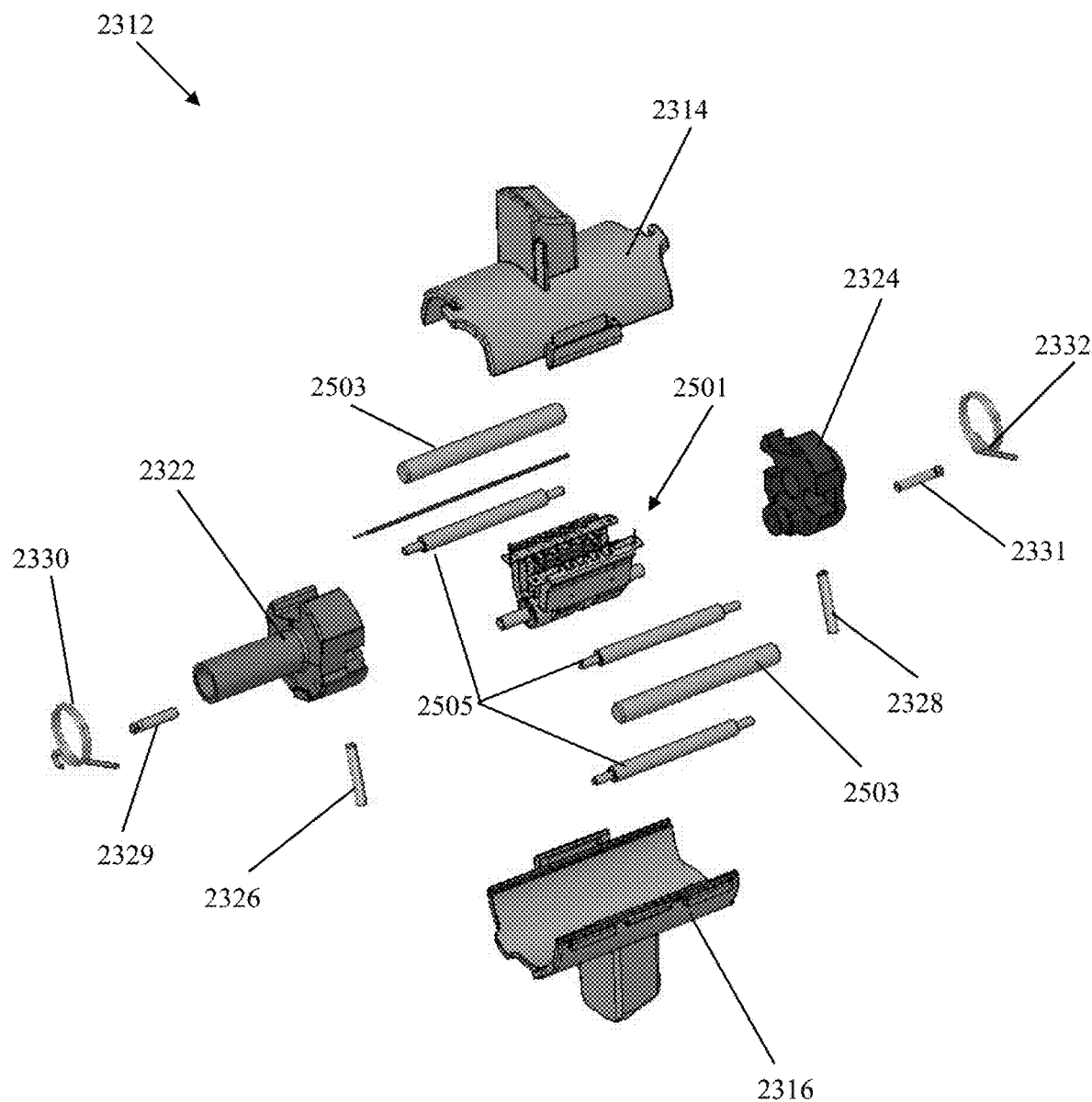
FIG. 25 is an exploded view of the advancing mechanism of FIG. 24.

The exploded view of FIG. 25 illustrates the various components housed between the clutch housings 2314, 2316. In particular, a clutch mechanism 2501 is disposed between the upper and lower clutch housings 2314, 2316 and distal and proximal anti-rotation stops 2322, 2324. The clutch mechanism 2501, discussed in more detail below, includes first and second clutch members that are pivotally coupled to one another by a clutch shaft that extends between the distal and proximal anti-rotation stops 2322, 2324. In addition, a pair of bearing shafts 2503 ride in slots formed in the distal and proximal anti-rotation stops 2322, 2324 and are positioned radially outward from the first and second clutch members of the clutch mechanism 2501. The bearing shafts 2503 can rotate and move radially within the slots of the anti-rotation stops 2322, 2324. One or more stabilization shafts 2505 also extend between the distal and proximal anti-rotation stops 2322, 2324 to improve rigidity of the advancing mechanism 2312.

Figure 26:
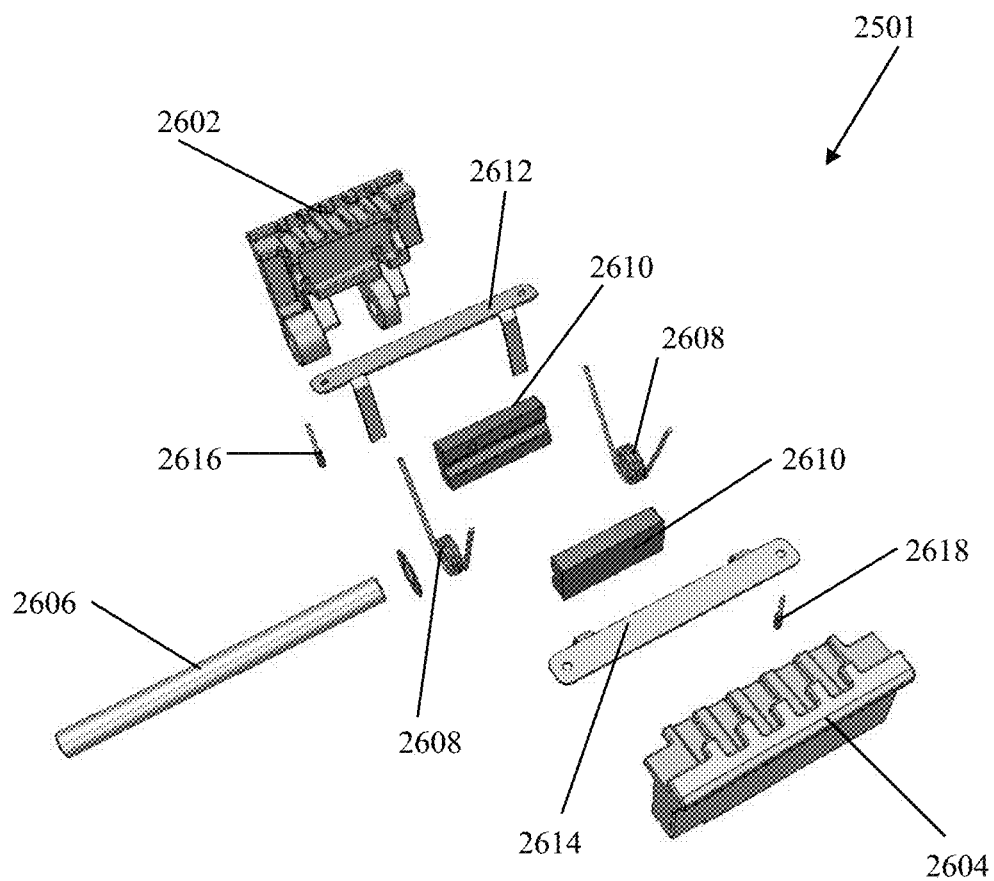
FIG. 26 is an exploded view of the clutch mechanism of FIG. 25.

FIG. 26 illustrates the clutch mechanism 2501 in greater detail. Similar to the clutch mechanism 1301 shown in FIG. 18, the clutch mechanism 2501 includes first and second clutch members 2602, 2604 that are pivotally coupled to one another by a clutch shaft 2606. In addition, the first and second clutch members 2602, 2604 are biased toward an open configuration by one or more biasing springs 2608 disposed around the clutch shaft 2606. As with the clutch mechanism 1301 described above, the first and second clutch members 2602, 2604 can have a variety of different shapes and sizes, and can include alternate arrangements of biasing components. Further, first and second clutch members 2602, 2604 can each include an insert 2610 that is configured to contact a connecting member 408 upon actuation of the clutch mechanism 2501. The insert 2610 can have a variety of shapes and sizes, and can be formed from a material that is the same as, or different from, a material used to form the first and second clutch members 2602, 2604. The insert 2610 can be selectively separable from its corresponding clutch member in order to facilitate replacement if the insert should become worn or if a different size connecting member 408 is utilized, etc.

Also similar to the clutch mechanism 1301 discussed above, the clutch mechanism 2501 can be configured to form part of an electrical circuit that activates one or more user feedback mechanisms (e.g., indicator lights 1104) when the advancing mechanism 2312 is in an engaged configuration. In particular, the first clutch member 2602 can include a first electrical connector 2612 and the second clutch member 2604 can include a second electrical connector 2614. Wire leads (not shown) can be electrically coupled to the first and second electrical connectors via posts 2616, 2618 (respectively) and extend to the one or more indicator lights 1104 and a power source (not shown). The first and second electrical connectors 2612, 2614 can thereby form a switch in a circuit connecting the power source to the one of more indicator lights 1104. When the clutch mechanism 2501 is actuated and the first and second clutch members 2602, 2604 contact the connecting member 408, the first and second electrical connectors 2612, 2614 can also contact the connecting member 408 to close the switch via, for example, the conductive material of the connecting member 408, as described above. As a result, the one or more indicator lights 1104 can be powered on only when the clutch mechanism 2501 is contacting the connecting member 408. As noted above, powering on the one or more indicator lights 1104 is just one example of feedback that can be provided by such a switch. In other embodiments, the open or closed position of the switch can be communicated to a controller or other component of the system. Such a controller could provide feedback to a user visually, audibly, haptically, or otherwise, or could control delivery of therapy (e.g., delivery of RF electrical energy from the needle 512 or other instrument).

Figure 27A:
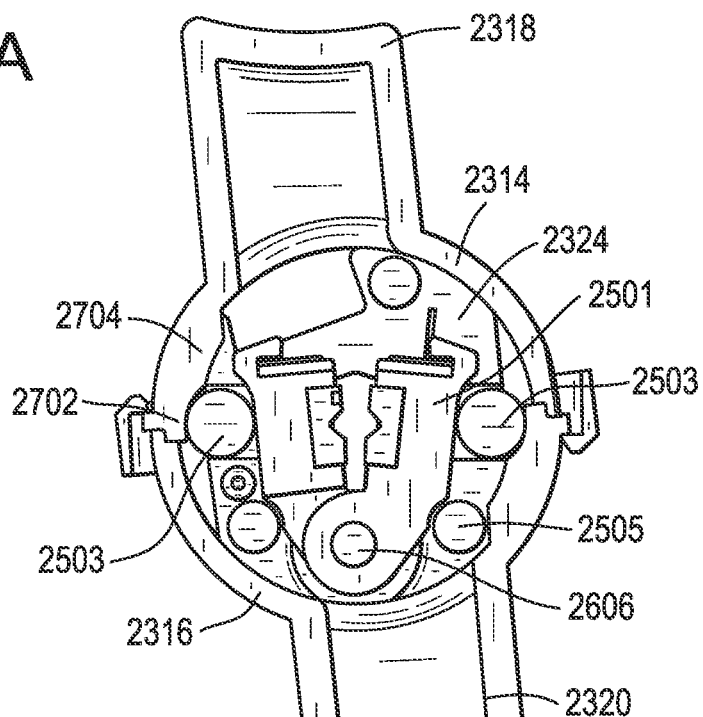
FIG. 27A is a front view of the advancing mechanism of FIG. 24 in a disengaged configuration.
Figure 27B:
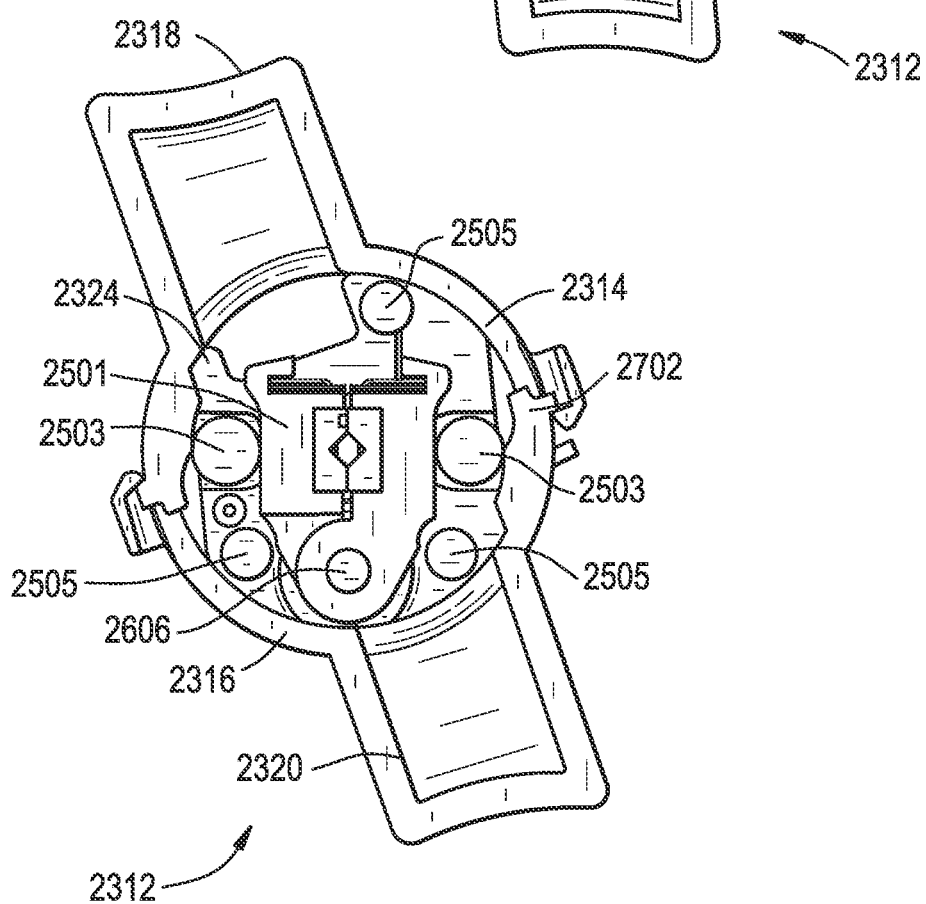
FIG. 27B is a front view of the advancing mechanism of FIG. 24 in an engaged configuration.

FIGS. 27A and 27B illustrate the disengaged and engaged configurations of the clutch mechanism 2501, along with the interaction between the clutch mechanism and other components of the advancing mechanism 2312. Because the proximal anti-rotation stop 2324 is prevented from rotating by the post 2328 (see FIGS. 24 and 25) that extends into a track formed on the lower housing 402 (not shown), the motion illustrated in FIGS. 27A and 27B is the rotation of clutch housings 2314, 2316 around the anti-rotation stop 2324. The stabilization shafts 2505 and clutch shaft 2606 do not move in the plane of the figure for the same reason, as they extend between recesses formed in the distal and proximal anti-rotation stops 2322, 2324. The bearing shafts 2503 can move radially inward or outward, however, because they are received within slots formed in the anti-rotation stops 2322, 2324 that allow for such movement.

In the disengaged configuration of FIG. 27A, the clutch housings 2314, 2316 are positioned such that a recess 2702 is aligned with each bearing shaft 2503, allowing the bearing shaft to move radially outward. In this configuration, the force of the clutch mechanism 2501 biasing springs 2608 (see FIG. 26) separates the first and second clutch members 2602, 2604 and urges the bearing shafts 2503 to their outer-most position. In addition, the clutch members 2602, 2604 remain out of contact with a connecting member 408 (not shown) of the device.

To engage the advancing mechanism 2312, a user can rotate the clutch housings 2314, 2316 to the configuration shown in FIG. 27B, e.g., via manipulation of the actuating protrusions 2318, 2320. As the clutch housings 2314, 2316 are rotated, the recesses 2702 move out of alignment with the bearing shafts 2503 and a flat (or even protruding) portion 2704 of the clutch housings can come into alignment with the bearing shafts. This rotational movement of the clutch housings 2314, 2316 results in a radial inward movement of the bearing shafts 2503, which overcomes the force of the biasing springs 2608 and moves the first and second clutch members 2602, 2604 toward one another. In the configuration shown in FIG. 27B, a connecting member (not shown) disposed between the first and second clutch members 2602, 2604 would be securely grasped. A user could then translate the advancing mechanism 2312 proximally or distally to effect similar movement of a needle or other surgical instrument coupled to the connecting member, as described above.

Figure 28:
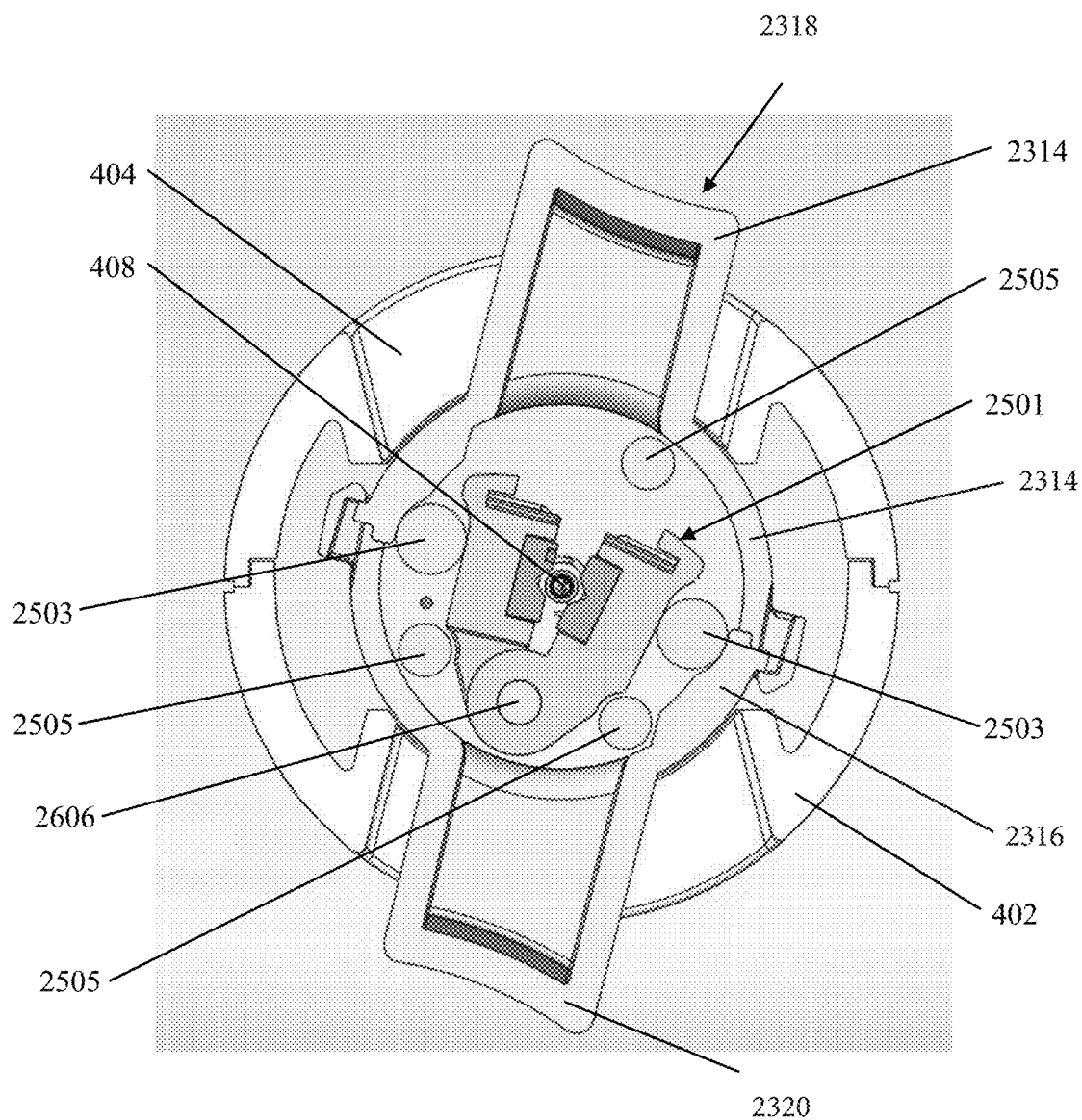
FIG. 28 is a front view of the advancing mechanism of FIG. 24 in a disengaged configuration within a catheter device housing.

FIG. 28 illustrates the advancing mechanism 2312 relative to the lower housing 402, upper housing 404, and connecting member 408. The advancing mechanism is shown in the disengaged configuration of FIG. 27A, where is it not in contact with the connecting member 408. As can be seen by comparing FIG. 28 with FIGS. 14A and 14B, the advancing mechanism 2312 is entirely contained within the clutch housings 2314, 2316, and does not rely on interaction between the lower and upper housings 402, 404 and bearing assemblies 1214 to effect movement of the clutch members 2602, 2604.

The advancing mechanisms 212 and 2312 described above are just two possible embodiments. Moreover, both embodiments utilize clutch members that move toward or away from one another via a pivoting connection. In other embodiments, the clutch members 1302, 1304 (or 2602, 2604) can be linearly separated from one another. For example, tapered surfaces on the clutch members 1302, 1304 and clutch housing 1202 can cause the clutch members to be pressed toward one another as the advancing mechanism 212 is rotated or translated. In still other embodiments, the advancing mechanism 212 can include separate mechanisms to control the engagement of the mechanism to the connecting member 408 and the translation of the mechanism relative to the device, or the mechanism could be configured such that a single motion (e.g., distal translation) causes both engagement with, and distal advancement of, the connecting member 408. Still further, devices according to the teachings of the present disclosure can utilize any manner of gearing systems (e.g., worm gears, etc.) and actuators (e.g., solenoids, etc.) to assist or completely power movement of the advancing mechanism.

FIGS. 29-34 illustrate additional embodiments of advancing mechanisms that can employ known datum positions to limit distal advancement of a needle or other surgical instrument disposed within a distal portion of a catheter. Accordingly, a position of a needle or other instrument within a catheter can be known with certainty not only when retracted proximally against the above-described retraction stop, but also when deployed distally against a deployment stop, as described below. Known positioning of deployment stops relative to a distal end of the catheter can ensure a certain length of needle or instrument deployment beyond the distal end of the catheter when a protrusion or other locating feature formed on the instrument is in contact with the deployment stop. Moreover, a series of deployment stops can be utilized to provide various lengths of instrument deployment, e.g., 2 mm, 5 mm, 8 mm, etc. Still further, such embodiments can optionally employ a biasing element. The absence of a biasing element in certain embodiments can eliminate the above-described need to compensate for tension in the connecting member and compression in the catheter that a biasing element can impart.

Figure 29:
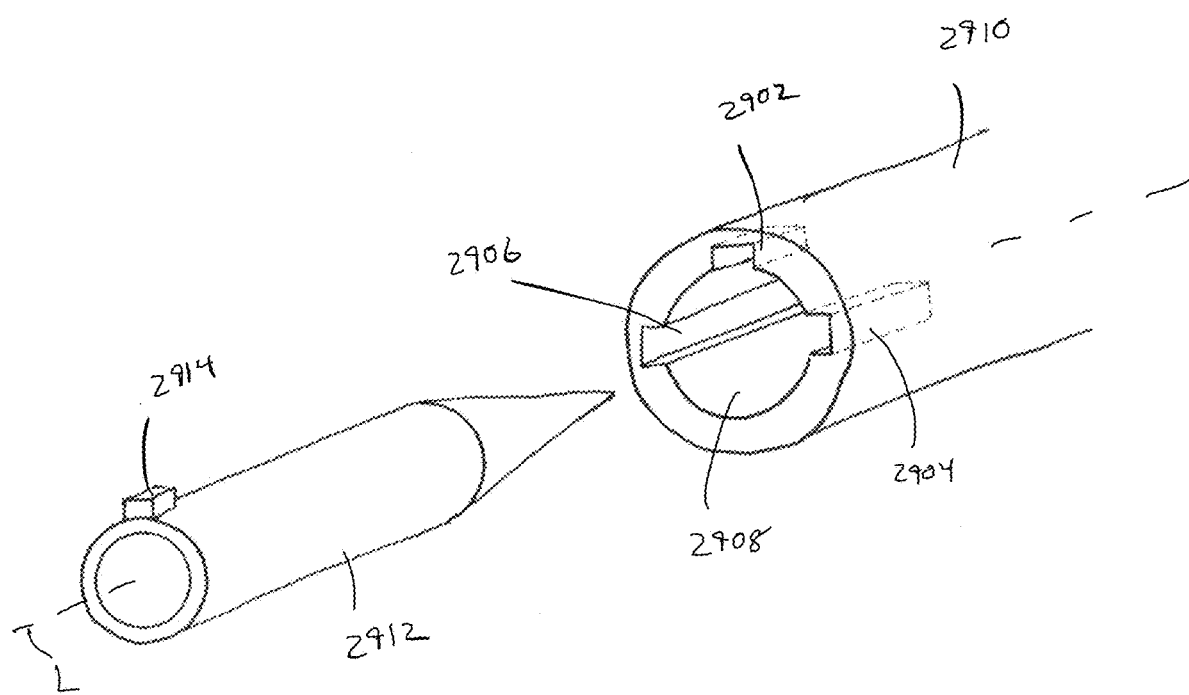
FIG. 29 is a partial perspective view of one embodiment of a catheter device having a selectively deployable instrument with a plurality of deployment stops.

In a first embodiment shown in FIG. 29, a series of tracks 2902, 2904, 2906 can be formed in a sidewall of an inner lumen 2908 of a catheter 2910. An elongate body 2912, e.g., a needle, or another surgical instrument can be positioned within the inner lumen 2908 and configured to any of translate and rotate relative thereto. The elongate body 2912 can include a protrusion 2914 formed on an outer surface thereof. The protrusion 2914 can have a shape that is complementary to the tracks 2902, 2904, 2906 such that the tracks can receive the protrusion and guide movement of the elongate body 2912 relative to the catheter 2910. For example, at a proximal position the elongate body 2912 can be rotated about a longitudinal axis L to align the protrusion 2914 with one of the tracks 2902, 2904, 2906. The elongate body 2912 can then be advanced relative to the catheter such that the protrusion 2914 enters one of the tracks 2902, 2904, 2906. The elongate body 2912 can be advanced until the protrusion reaches a deployment stop formed by the distal end of the track within which it is disposed. At that point, interference between the protrusion 2914 and the distal end of the track can prevent further advancement of the elongate body 2912 relative to the catheter 2910. By terminating the tracks 2902, 2904, 2906 at particular distances from a distal end of the catheter 2910, the elongate body can be limited to deployment at particular distances from a distal end of the catheter 2910.

By way of example, and as shown in FIG. 29, a first track 2902 can be shorter than a second track 2904, which can be shorter than a third track 2906. By rotating the elongate body 2912 in a proximal position such that the protrusion 2914 aligns with the first track 2902 and then advancing the elongate body distally, the length of the first track can limit the distance that the elongate body can be advanced relative to the catheter. If a greater distance is desired, the elongate body 2912 can be retracted to a proximal position, rotated to align with one of the longer tracks 2904, 2906, and advanced distally to the end of the selected track.

Such a configuration can provide certainty to a user of the relative positioning of an elongate body disposed within a catheter both when the elongate body is retracted proximally against a retraction stop, as described above, as well as at various deployment positions wherein the elongate body is advanced against a distal end of one of the tracks 2902, 2904, 2906. And because the tracks 2902, 2904, 2906 are formed in a sidewall of the catheter 2910 along a portion thereof that is distal to any steering mechanism, a user can be assured that any proximal deformation of the catheter due to steering, etc. will not impact the distance by which the elongate body extends from a distal end of the catheter.

FIG. 29 illustrates three tracks 2902, 2904, 2906 of different lengths. In other embodiments, however, any number of tracks can be employed to provide various distances of elongate body advancement or deployment. Any of the various tracks can be selected at a proximal end of the device by controlling rotation of the elongate body 2912 relative to the catheter 2910. For example, in some embodiments a knob or other actuating feature can be coupled to the elongate body along a proximal portion thereof and can be used to rotate the elongate body 2912. Markings, detents, or other identifying features on, for example, a housing disposed about the elongate body 2912 can indicate to a user which track the protrusion 2914 is aligned with, e.g., by denoting the distal advancement permitted by that track (e.g., 2 mm, 5 mm, 8 mm, etc.).

Figure 30:
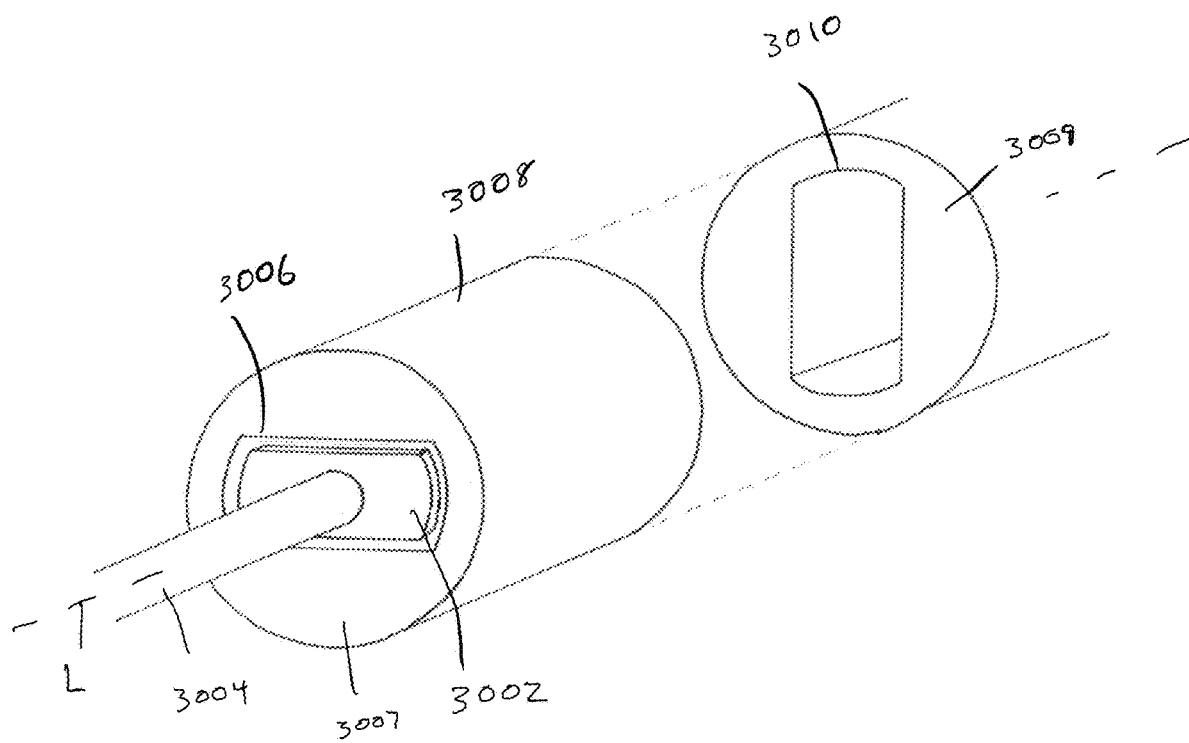
FIG. 30 is a partial perspective view of another embodiment of a catheter device having a selectively deployable instrument with a plurality of deployment stops.

FIG. 30 illustrates a second embodiment in which a flange 3002 or other feature formed on an elongate body 3004 is utilized in combination with complementary through-hole 3006 formed in the catheter 3008 to selectively permit advancement of the elongate body 3004 when rotated into a correctly keyed orientation. For example, in FIG. 30 the elongate body 3004 is shown rotated into a position in which the flange 3002 is aligned or keyed to advance through the hole 3006. In this rotational position, however, the elongate body would be blocked from advancing beyond the more distal through-hole 3010. To achieve such further distal advancement, the elongate body 3004 would need to rotate 90° after passing through the through-hole 3006.

Such a system of keyed flanges and through-holes at different rotational orientations about a longitudinal axis L can provide for known and selectively limited advancement of the elongate body 3004 relative to the catheter 3008 in the same manner as the various tracks described above. For example, if the position of the through-hole 3006 is known relative to the distal end of the catheter 3008 and the position of the flange 3002 is known relative to the distal end of the elongate body 3004, a known relative position of the distal ends of the elongate body 3004 and catheter 3008 can be determined whenever the elongate body is advanced to abut against, but not pass through, the through hole 3006 (e.g., in a case where the elongate body is rotated about the axis L such that it cannot pass through the hole 3006). Further, the position of the hole 3006 can be distal of any steering mechanism of the catheter 3008, e.g., along a distal portion thereof, such that any deformation or movement of the catheter 3008 and/or elongate body 3004 proximally due to catheter steering will not influence the relative positioning of the catheter and elongate body distal ends, as described above.

Moreover, by disposing a series of through-holes (e.g., holes 3006, 3010, etc.) along a length of the catheter at various distances relative to a distal end thereof, the elongate body 3004 can be selectively advanced various distances by rotating it to selectively align the flange 3002 with the various through-holes. When misaligned with a particular through-hole, distal advancement of the elongate body can press the flange 3002 against a bulkhead surrounding the through-hole (e.g., bulkhead 3007 surrounding through-hole 3006 or bulkhead 3009 surrounding through-hole 3010), thereby forming a deployment stop and preventing any additional unintended advancement.

Note that, in some embodiments, the above-described configuration can be used in combination with proximal biasing of the elongate body 3004 to maintain the elongate body at a desired position relative to the catheter. For example, after passing the flange of the elongate body through a hole, the elongate body can be rotated to prevent withdrawal through the hole and then urged proximally to press the flange against the bulkhead it just advanced through. For example, the elongate body 3004 can be advanced distally from the position shown in FIG. 30 such that the flange passes through the hole 3006, then the elongate body can be rotated 90° to align it for passage through the hole 3010, but can be withdrawn proximally, e.g., by a biasing mechanism. Such proximal withdrawal could maintain the flange 3002 in contact with the bulkhead 3007 and maintain the position of the elongate body relative to the catheter. Such a configuration provides for, in effect, a series of retraction stops (like the stop 518 described above) along a length of a distal portion of the catheter.

While one embodiment of the flange 3002 and through-holes 3006, 3010 are shown in FIG. 30, any of a variety of different configurations are possible. For example, the flange 3002 can be in the form of one or more radially extending protrusions of various shapes and sizes, and the through-holes 3006, 3010 can be complementary and disposed at any of a variety of rotational positions. Actuators as described above can be utilized to control rotation and distal advancement or proximal retraction of the elongate body from a proximal portion thereof.

Figure 31:
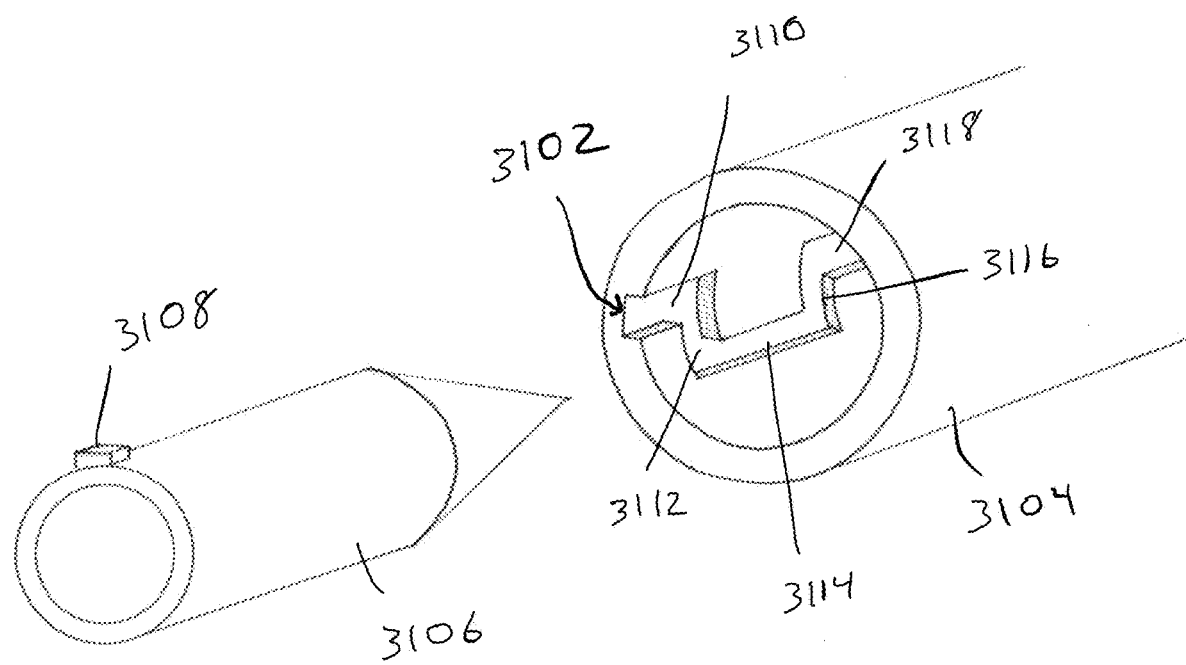
FIG. 31 is a partial perspective view of another embodiment of a catheter device having a selectively deployable instrument with a plurality of deployment stops.

FIG. 31 illustrates still another embodiment of an advancing mechanism in which a single tortuous or labyrinthine track 3102 is formed in a sidewall of a catheter 3104 to guide movement of an elongate body 3106 relative to the catheter. As described above, a protrusion 3108 formed on the elongate body 3106 can be configured to be received within the track 3102. Once the protrusion 3108 is received within a first portion 3110 of the track 3102, the elongate body 3106 can be prevented from rotating relative to the catheter 3104 and can be limited to advancing distally only until the protrusion 3108 abuts against a distal end of the first portion of the track, thereby reaching a first deployment stop. As described above, the distal end of the first portion 3110 of the track 3102 can be positioned at a known distance from a distal end of the catheter. This fixed distance that can be used in combination with the fixed distance between the protrusion 3108 and the distal end of the elongate body 3106 to determine a relative position between the distal ends of the catheter and the elongate body.

To continue advancing the elongate body 3106 further relative to the catheter 3104, the elongate body can be rotated such that the protrusion 3108 passes through a first transition 3112 of the track 3102. Once the protrusion 3108 is aligned with a second portion 3114 of the track 3102, the elongate body 3106 can be advanced distally until the protrusion abuts against a distal end of the second portion of the track, thereby reaching a second deployment stop. If still further distal advancement is desired, the elongate body 3106 can be rotated to move the protrusion 3108 through a second transition 3116 into alignment with a third portion 3118 of the track 3102. In various embodiments, any number of track portions and transitions can be utilized to provide various stepped advancement of the elongate body relative to the catheter.

In addition, the elongate body 3106 can be either advanced against distal ends of each portion of the track 3102 or proximally withdrawn against proximal ends of each portion to control positioning of the elongate body relative to the catheter 3104. This is similar in concept to the distal advancement or proximal withdrawal of the flange 3002 into a bulkhead in the embodiment shown in FIG. 31. Regardless, the end result can be a series of effective retraction or deployment stops against either proximal retraction or distal advancement that can be used to verifiably achieve and maintain a position of the elongate body relative to the catheter regardless of relative movement between these components along a more proximal portion thereof due to, e.g., deformation from catheter steering, etc.

Figure 32:
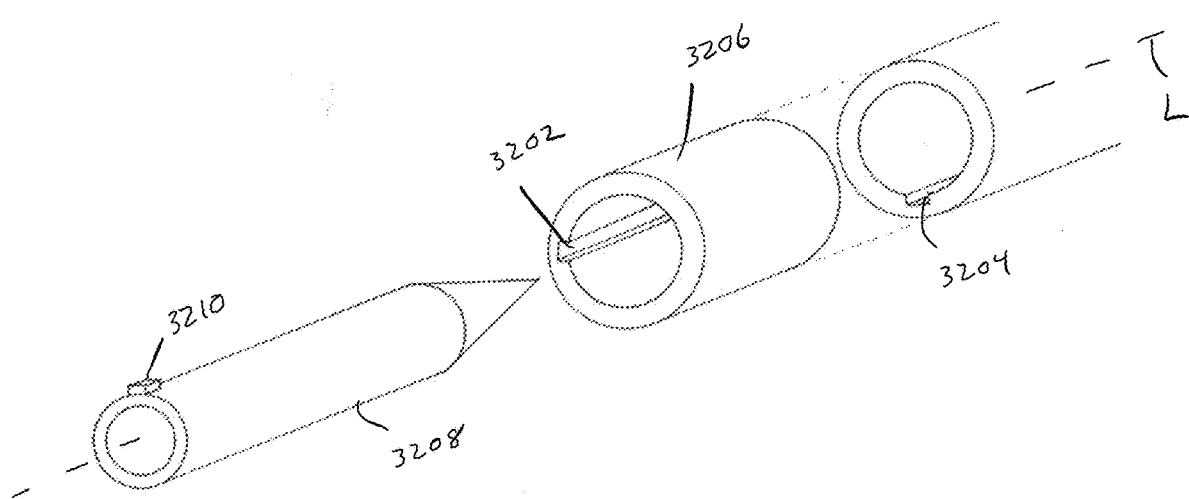
FIG. 32 is a partial perspective view of another embodiment of a catheter device having a selectively deployable instrument with a plurality of deployment stops.

FIG. 32 illustrates still another embodiment in which a series of tracks 3202, 3204 are formed in a sidewall of a catheter 3206 at different angular positions about a longitudinal axis L of the catheter. An elongate body 3208 disposed within an inner lumen of the catheter 3206 can include a protrusion, key, or other feature 3210 formed on an outer surface of the elongate body that can be received within the tracks 3202, 3204 to guide movement of the elongate body relative to the catheter. By positioning the tracks 3202, 3204 at different angular positions about the longitudinal axis L, the elongate body 3208 can be required to rotate by some amount in order to move the key 3210 from alignment with, e.g., the first track 3202 and into alignment with, e.g., the second track 3204. This means that, prior to such rotation, distal advancement of the elongate body 3208 relative to the catheter 3206 can reach a positive deployment stop when the key 3210 abuts against a distal end of the track in which it is disposed. As noted above, the tracks 3202, 3204 can be formed in a distal portion of the catheter 3206 located distal to any steering portion, etc. Accordingly, a distance between a distal-most end of any track and a distal end of the catheter can be known and unchanging. The key 3210 or other feature can similarly be fixed relative to a distal end of the elongate body 3208 such that a relative position between a distal end of the elongate body 3208 and a distal end of the catheter 3206 (e.g., how far the distal end of the elongate body extends beyond the distal end of the catheter) can be known when the key 3210 abuts against the distal end of a track.

Transitioning the key 3210 between tracks 3202, 3204 can be accomplished in a variety of manners. For example, transition track portions (e.g., such as transition portions 3112, 3116 described above) can be employed to bridge between different tracks. Alternatively, annular transition portions can be provided that allow 360° rotation of the elongate body and intersect with each track 3202, 3204. While only two tracks are shown in the figure, any number can be employed along the length of a catheter. Further, in some embodiments, it may be possible to enter more than one track from a given transition area. For example, a configuration similar to that shown in FIG. 29 could be employed wherein a plurality of tracks (e.g., having different lengths, etc.) can be selected based on rotation of the elongate body to align the key 3210 with the desired track.

Figure 33:
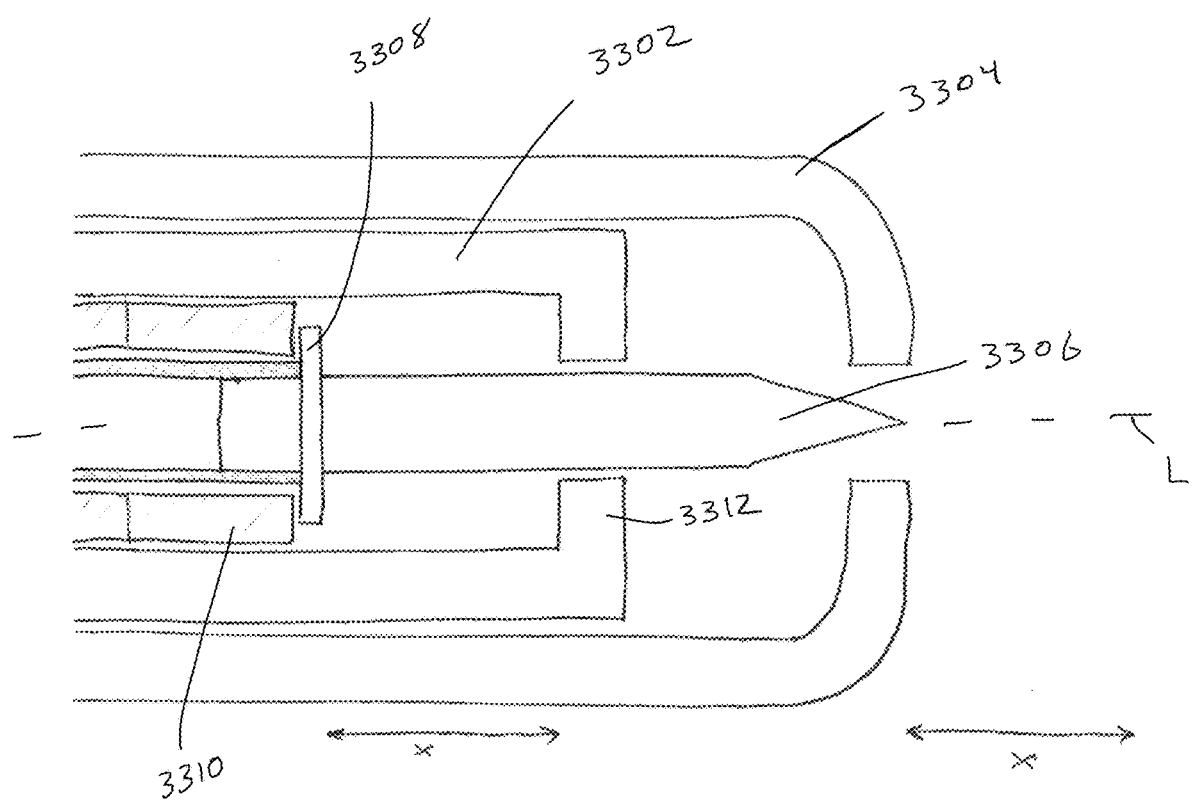
FIG. 33 is a cross sectional view of another embodiment of a catheter device having a selectively deployable instrument with an adjustable deployment stop.

FIG. 33 illustrates an embodiment in which an intermediate shaft 3302 is disposed within a catheter 3304 over an elongate body 3306 to provide a positive stop for distal advancement of the elongate body 3306 relative to the catheter. Similar to the configurations described above, the elongate body 3306 can include a flange 3308 or other feature formed thereon that can be used in combination with a fixed retraction stop 3310 to reliably maintain the elongate body at a known location within the catheter 3304 and avoid inadvertent extension of the elongate body beyond a distal end of the catheter during, e.g., catheter placement, etc. The intermediate shaft 3302 can be disposed about the elongate body 3306 and retraction stop 3310, and can be movable relative thereto to adjust its position along a longitudinal axis L of the catheter. The intermediate shaft 3302 can include a distal end 3312 having a reduced diameter lumen such that the elongate body 3306 can pass through a distal end of the shaft 3302 but the flange 3308 cannot.

As a result of this configuration, the elongate body will be positively stopped from advancing distally relative to the catheter 3304 when the flange 3308 abuts against the distal end 3312 of the intermediate shaft 3302. Moreover, by setting a distance X between the distal end 3312 of the intermediate shaft 3302 and the retraction stop 3310 at a time when the flange 3308 of the elongate body 3306 is retracted against the stop and a distal end of the elongate body is aligned with a distal end of the catheter 3304 (e.g., as shown in FIG. 33), a user can be assured that the elongate body will extend from a distal end of the catheter by the same distance X when the elongate body is advanced distally to abut the flange 3308 into the distal end 3312 of the shaft 3302. Of course, in other embodiments it can be possible to adjust the configuration shown in FIG. 33 to accommodate for any appreciable thickness of the flange 3308 and, e.g., a desired safety setback of the elongate body 3306 within the catheter 3304 when in a retracted state.

The position of the intermediate shaft 3302 relative to the catheter 3304 and retraction stop 3310 can be adjusted in a number of manners. For example, in some embodiments the intermediate shaft 3302 can be in threaded engagement with the catheter 3304 such that rotation of the shaft 3302 can adjust its position along the longitudinal axis L of the catheter. In other embodiments, the shaft 3302 can be indexed relative to the catheter 3304 using a series of detents with a spring-loaded or fixed pawl-like feature, or using any other known configuration. In some embodiments, the shaft 3302 can be indexed to the catheter 3304 at a position distal to any steering portion of the catheter to avoid any inadvertent movement between the shaft 3302 and the catheter 3304 that might introduce variation into the distance X between the distal end 3312 of the shaft and the fixed retraction stop 3310.

Figure 34:
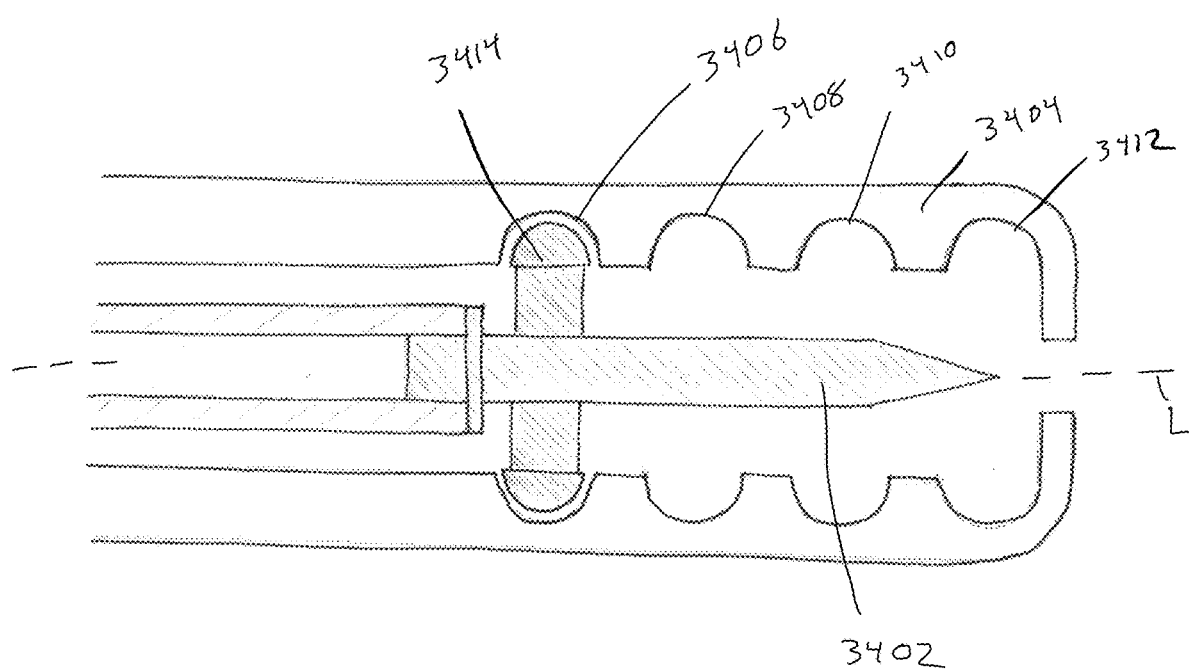
FIG. 34 is a cross-sectional view of another embodiment of a catheter device having a selectively deployable instrument with a plurality of deployment stops.

A further configuration is shown in FIG. 34, in which a position of an elongate body 3402 relative to a catheter 3404 is controlled using a series of detents 3406, 3408, 3410, 3412 formed on a sidewall of an inner lumen of the catheter. The elongate body 3402 can include a protrusion 3414 formed on an outer surface thereof that can interface with the detents 3406, 3408, 3410, 3412 to maintain a position of the elongate body relative to the catheter. Because the positions of the detents 3406, 3408, 3410, 3412 are known relative to the distal end of the catheter 3404 and the position of the protrusion 3414 is known relative to the distal end of the elongate body 3402, the relative positions of the distal ends of the elongate body and the catheter can be known for each of the detents. Further, the protrusion 3414 can interface with each detent in a manner that prevents both proximal and distal movement of the elongate body 3402 relative to the catheter 3404 until a sufficient force is applied to push the protrusion into an adjacent detent.

The protrusion 3414 can have a variety of configurations to enable transition between adjacent detents after sufficient force is applied thereto. For example, the protrusion 3414 can be formed from a unitary deformable material (e.g., any of a number of polymers, etc.) with sufficient rigidity to resist deformation until sufficient force is applied thereto. In other embodiments, the protrusion 3414 can be a spring-ball mechanism. In still other embodiments, the protrusion 3414 can be formed from a rigid material and the detents 3406, 3408, 3410, 3412 can be formed from a sufficiently deformable material to allow selective movement of the elongate body.

The protrusion 3414 can be formed on one side of the elongate body 3402 or, as shown in FIG. 34, can be formed on opposing sides of the elongate body 3402. In still other embodiments, a plurality of protrusions and detents can be spaced around a circumference of the elongate body 3402, or a single feature can extend annularly around a circumference thereof and interface with annular-shaped detents formed in the catheter 3404. Still further, in some embodiments the illustrated arrangement can be reversed such that a protrusion formed on the catheter 3404 can interface with detents formed on the elongate body 3402, or a single detent formed on any of the elongate body and catheter can be configured to interface with one of a series of protrusions formed along a length of the other component.

The devices disclosed herein can be designed to be disposed after a single use, or they can be designed for multiple uses. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present disclosure.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

All papers and publications cited herein are hereby incorporated by reference in their entirety. One skilled in the art will appreciate further features and advantages of the present disclosure based on the above-described embodiments. Accordingly, the present disclosure is not to be limited by what has been particularly shown and described, except as indicated by the appended claims.

What is claimed is:

1. An ablation device, comprising:
    a catheter having an inner lumen extending there-through, the inner lumen including a retraction stop formed on a distal portion thereof, the retraction stop having a fixed longitudinal position relative to the catheter;
    a needle slidably disposed within the inner lumen of the catheter, the needle including an inner lumen, at least one outlet port formed on a distal portion thereof, and at least one protrusion formed on an outer surface thereof proximal to the at least one outlet port and distal to the retraction stop on the catheter inner lumen, a distal portion of the needle being configured to ablate tissue;
    a biasing element coupled to the needle and configured to urge the needle proximally such that the at least one protrusion on the needle abuts against the retraction stop on the catheter inner lumen; and
    an advancing mechanism configured to selectively urge the needle distally relative to the catheter.

2. The ablation device of claim 1, wherein the catheter is steerable using one or more control cables extending through the catheter.

3. The ablation device of claim 1, wherein the advancing mechanism includes a clutch to selectively couple to the needle.

4. The ablation device of claim 3, wherein the clutch is positioned in a proximal portion of the catheter within a handle assembly.

5. The ablation device of claim 1, wherein the biasing element is positioned in a proximal portion of the catheter within a handle assembly.

6. The ablation device of claim 1, wherein the retraction stop is positioned such that a distal tip of the needle is proximal to a distal tip of the catheter when the at least one protrusion is abutting against the retraction stop.

7. The ablation device of claim 6, wherein the advancing mechanism is configured to advance the needle distally such that the distal tip of the needle is distal to the distal tip of the catheter.

8. The ablation device of claim 1, wherein the at least one protrusion on the needle includes one or more fluid channels formed therein to allow fluid flow there-through.

9. The ablation device of claim 1, further comprising at least one heating element disposed within the inner lumen of the needle and positioned within the distal portion thereof proximal to the at least one outlet port, the at least one heating element being configured to heat fluid flowing through the inner lumen of the needle.

10. An ablation device, comprising:
    a catheter having an inner lumen extending there-through, the inner lumen including a retraction stop formed on a distal portion thereof;
    a needle slidably disposed within the inner lumen of the catheter, the needle including an inner lumen, at least one outlet port formed on a distal portion thereof, and at least one protrusion formed on an outer surface thereof proximal to the at least one outlet port and distal to the retraction stop on the catheter inner lumen, a distal portion of the needle being configured to ablate tissue;
    a biasing element coupled to the needle and configured to urge the needle proximally such that the at least one protrusion on the needle abuts against the retraction stop on the catheter inner lumen; and
    an advancing mechanism configured to selectively urge the needle distally relative to the catheter,
    wherein the advancing mechanism includes a clutch to selectively couple to the needle.

11. The ablation device of claim 10, wherein the clutch is positioned in a proximal portion of the catheter within a handle assembly.

12. An ablation device, comprising:
    a catheter having an inner lumen extending there-through, the inner lumen including a retraction stop formed on a distal portion thereof;
    a needle slidably disposed within the inner lumen of the catheter, the needle including an inner lumen, at least one outlet port formed on a distal portion thereof, and at least one protrusion formed on an outer surface thereof proximal to the at least one outlet port and distal to the retraction stop on the catheter inner lumen, a distal portion of the needle being configured to ablate tissue;
    a biasing element coupled to the needle and configured to urge the needle proximally such that the at least one protrusion on the needle abuts against the retraction stop on the catheter inner lumen; and
    an advancing mechanism configured to selectively urge the needle distally relative to the catheter,
    wherein the at least one protrusion on the needle includes one or more fluid channels formed therein to allow fluid flow there-through.

\* \* \* \* \*